(12) United States Patent
Al-Ali et al.

(10) Patent No.: US 8,050,728 B2
(45) Date of Patent: Nov. 1, 2011

(54) MULTIPLE WAVELENGTH SENSOR DRIVERS

(75) Inventors: Ammar Al-Ali, Tustin, CA (US); Robert Smith, Lake Forest, CA (US); David Dalke, Irvine, CA (US); Mohamed Diab, Mission Viejo, CA (US); Marcelo Lamego, Rancho Santa Margarita, CA (US)

(73) Assignee: Masimo Laboratories, Inc., Irvine, CA (US)

( * ) Notice: Subject to any disclaimer, the term of this patent is extended or adjusted under 35 U.S.C. 154(b) by 1577 days.

(21) Appl. No.: 11/366,997

(22) Filed: Mar. 1, 2006

(65) Prior Publication Data

US 2006/0241363 A1    Oct. 26, 2006

Related U.S. Application Data

(60) Provisional application No. 60/657,596, filed on Mar. 1, 2005, provisional application No. 60/657,281, filed on Mar. 1, 2005, provisional application No. 60/657,268, filed on Mar. 1, 2005, provisional application No. 60/657,759, filed on Mar. 1, 2005.

(51) Int. Cl.
*A61B 5/1455* (2006.01)

(52) U.S. Cl. .................................... 600/310; 600/323

(58) Field of Classification Search ........... 600/309–344
See application file for complete search history.

(56) References Cited

U.S. PATENT DOCUMENTS

| | | |
|---|---|---|
| 3,910,701 A | 10/1975 | Henderson et al. |
| 3,998,550 A | 12/1976 | Konishi et al. |
| 4,014,321 A | 3/1977 | March |
| 4,157,708 A | 6/1979 | Imura |
| 4,167,331 A | 9/1979 | Nielsen |
| 4,266,554 A | 5/1981 | Hamaguri |
| 4,267,844 A | 5/1981 | Yamanishi |
| 4,446,871 A | 5/1984 | Imura |
| 4,531,527 A | 7/1985 | Reinhold, Jr. et al. |

(Continued)

FOREIGN PATENT DOCUMENTS

EP    41 92 23    3/1991

(Continued)

OTHER PUBLICATIONS

International Search Report for PCT/US2006/007516, mailed on Jan. 11, 2007, in 4 pages.

(Continued)

*Primary Examiner* — Eric Winakur
*Assistant Examiner* — Marjan Fardanesh
(74) *Attorney, Agent, or Firm* — Knobbe, Martens, Olson & Bear LLP

(57) ABSTRACT

A cable is capable of communicating signals between a monitor and a physiological sensor. The monitor is capable of activating individual light emitters of an emitter array arranged in an electrical grid by driving at least one of row drive lines and at least one of column drive lines of the electrical grid. The cable has a first row input, a first column input, a second row input and a second column input. The cable also has a first output which combines the first row input and the first column input and a second output which combines the second row input and the second column input. The inputs are adapted to connect to electrical grid drive lines of a monitor. Further, the outputs are adapted to connect to contacts of a physiological sensor having back-to-back configured LEDs in electrical communication with the contacts.

11 Claims, 48 Drawing Sheets

U.S. PATENT DOCUMENTS

| | | |
|---|---|---|
| 4,586,513 A | 5/1986 | Hamaguri |
| 4,621,643 A | 11/1986 | New et al. |
| 4,653,498 A | 3/1987 | New et al. |
| 4,655,225 A | 4/1987 | Dahne et al. |
| 4,685,464 A | 8/1987 | Goldberger |
| 4,694,833 A | 9/1987 | Hamaguri |
| 4,700,708 A | 10/1987 | New et al. |
| 4,714,341 A | 12/1987 | Hamaguri et al. |
| 4,770,179 A | 9/1988 | New et al. |
| 4,773,422 A | 9/1988 | Isaacson et al. |
| 4,781,195 A | 11/1988 | Martin |
| 4,800,885 A | 1/1989 | Johnson |
| 4,805,623 A | 2/1989 | Jobsis |
| 4,832,484 A | 5/1989 | Aoyagi et al. |
| 4,846,183 A | 7/1989 | Martin |
| 4,854,328 A | 8/1989 | Pollack |
| 4,863,265 A | 9/1989 | Flower et al. |
| 4,867,571 A | 9/1989 | Frick et al. |
| 4,869,254 A | 9/1989 | Stone et al. |
| 4,907,876 A | 3/1990 | Suzuki et al. |
| 4,911,167 A | 3/1990 | Corenman et al. |
| 4,934,372 A | 6/1990 | Corenman et al. |
| 4,938,218 A | 7/1990 | Goodman et al. |
| 4,942,877 A | 7/1990 | Sakai et al. |
| 4,955,379 A | 9/1990 | Hall |
| 4,960,126 A | 10/1990 | Conlon et al. |
| 4,960,128 A | 10/1990 | Gordon et al. |
| 4,964,010 A | 10/1990 | Miyasaka et al. |
| 4,964,408 A | 10/1990 | Hink et al. |
| 4,967,571 A | 11/1990 | Sporri |
| 4,975,581 A | 12/1990 | Robinson et al. |
| 4,986,665 A | 1/1991 | Yamanishi et al. |
| 4,997,769 A | 3/1991 | Lundsgaard |
| 5,025,791 A | 6/1991 | Niwa |
| RE33,643 E | 7/1991 | Isaacson et al. |
| 5,028,787 A | 7/1991 | Rosenthal et al. |
| 5,033,472 A | 7/1991 | Sato et al. |
| 5,041,187 A | 8/1991 | Hink et al. |
| 5,054,495 A | 10/1991 | Uemura et al. |
| 5,058,588 A | 10/1991 | Kaestle et al. |
| 5,069,213 A | 12/1991 | Polczynski |
| 5,077,476 A | 12/1991 | Rosenthal |
| 5,078,136 A | 1/1992 | Stone et al. |
| 5,137,023 A | 8/1992 | Mendelson et al. |
| 5,163,438 A | 11/1992 | Gordon et al. |
| 5,189,609 A | 2/1993 | Tivig et al. |
| 5,190,040 A | 3/1993 | Aoyagi |
| 5,209,230 A | 5/1993 | Swedlow et al. |
| 5,226,053 A | 7/1993 | Cho et al. |
| 5,246,002 A | 9/1993 | Prosser |
| 5,247,931 A | 9/1993 | Norwood |
| 5,259,381 A | 11/1993 | Cheung et al. |
| 5,267,562 A | 12/1993 | Ukawa et al. |
| 5,267,563 A | 12/1993 | Swedlow et al. |
| 5,278,627 A | 1/1994 | Aoyagi |
| 5,297,548 A | 3/1994 | Pologe |
| 5,313,940 A | 5/1994 | Fuse et al. |
| 5,331,549 A | 7/1994 | Crawford, Jr. |
| 5,335,659 A | 8/1994 | Pologe et al. |
| 5,337,744 A | 8/1994 | Branigan |
| 5,337,745 A | 8/1994 | Benaron |
| 5,341,805 A | 8/1994 | Stavridi et al. |
| 5,348,004 A | 9/1994 | Hollub |
| 5,351,685 A | 10/1994 | Potratz |
| 5,355,880 A | 10/1994 | Thomas et al. |
| 5,355,882 A | 10/1994 | Ukawa et al. |
| 5,361,758 A | 11/1994 | Hall et al. |
| 5,368,224 A | 11/1994 | Richardson et al. |
| D353,195 S | 12/1994 | Savage et al. |
| D353,196 S | 12/1994 | Savage et al. |
| 5,377,676 A | 1/1995 | Vari et al. |
| 5,385,143 A | 1/1995 | Aoyagi |
| 5,387,122 A | 2/1995 | Goldberger et al. |
| 5,392,777 A | 2/1995 | Swedlow et al. |
| 5,413,101 A | 5/1995 | Sugiura |
| D359,546 S | 6/1995 | Savage et al. |
| 5,421,329 A | 6/1995 | Casciani et al. |
| 5,427,093 A | 6/1995 | Ogawa et al. |
| 5,429,128 A | 7/1995 | Cadell et al. |
| 5,431,170 A | 7/1995 | Mathews |
| 5,435,309 A | 7/1995 | Thomas et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| RE35,122 E | 12/1995 | Corenman et al. |
| 5,482,036 A | 1/1996 | Diab et al. |
| 5,490,505 A | 2/1996 | Diab et al. |
| 5,490,523 A | 2/1996 | Isaacson et al. |
| 5,494,032 A | 2/1996 | Robinson et al. |
| 5,494,043 A | 2/1996 | O'Sullivan et al. |
| 5,503,148 A | 4/1996 | Pologe et al. |
| 5,520,177 A | 5/1996 | Ogawa |
| 5,533,507 A | 7/1996 | Potratz |
| 5,533,511 A | 7/1996 | Kaspari et al. |
| 5,551,423 A | 9/1996 | Sugiura |
| 5,553,615 A | 9/1996 | Carim et al. |
| 5,555,882 A | 9/1996 | Richardson et al. |
| 5,561,275 A | 10/1996 | Savage et al. |
| 5,562,002 A | 10/1996 | Lalin |
| 5,575,284 A | 11/1996 | Athan et al. |
| 5,577,500 A | 11/1996 | Potratz |
| 5,584,299 A | 12/1996 | Sakai et al. |
| 5,588,427 A | 12/1996 | Tien |
| 5,590,649 A | 1/1997 | Caro et al. |
| 5,590,652 A | 1/1997 | Inai |
| 5,595,176 A | 1/1997 | Yamaura |
| 5,596,992 A | 1/1997 | Haaland et al. |
| 5,602,924 A | 2/1997 | Durand et al. |
| 5,603,623 A | 2/1997 | Nishikawa et al. |
| 5,630,413 A | 5/1997 | Thomas et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,059 A | 7/1997 | Fein et al. |
| 5,645,060 A | 7/1997 | Yorkey |
| 5,645,440 A | 7/1997 | Tobler et al. |
| 5,660,567 A | 8/1997 | Nierlich et al. |
| 5,662,106 A | 9/1997 | Swedlow et al. |
| 5,676,139 A | 10/1997 | Goldberger et al. |
| 5,676,141 A | 10/1997 | Hollub |
| 5,678,544 A | 10/1997 | Delonzor et al. |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,690,104 A | 11/1997 | Kanemoto et al. |
| 5,692,503 A | 12/1997 | Kuenstner |
| 5,697,371 A | 12/1997 | Aoyagi |
| 5,713,355 A | 2/1998 | Richardson et al. |
| 5,719,589 A * | 2/1998 | Norman et al. .................. 345/82 |
| 5,720,284 A | 2/1998 | Aoyagi et al. |
| D393,830 S | 4/1998 | Tobler et al. |
| 5,743,262 A | 4/1998 | Lepper, Jr. et al. |
| 5,743,263 A | 4/1998 | Baker, Jr. |
| 5,746,206 A | 5/1998 | Mannheimer |
| 5,746,697 A | 5/1998 | Swedlow et al. |
| 5,752,914 A | 5/1998 | Delonzor et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,772,587 A | 6/1998 | Gratton et al. |
| 5,779,630 A | 7/1998 | Fein et al. |
| 5,782,237 A | 7/1998 | Casciani et al. |
| 5,782,756 A | 7/1998 | Mannheimer |
| 5,782,757 A | 7/1998 | Diab et al. |
| 5,785,659 A | 7/1998 | Caro et al. |
| 5,790,729 A | 8/1998 | Pologe et al. |
| 5,791,347 A | 8/1998 | Flaherty et al. |
| 5,792,052 A | 8/1998 | Isaacson et al. |
| 5,793,485 A | 8/1998 | Gourley |
| 5,800,348 A | 9/1998 | Kaestle |
| 5,800,349 A | 9/1998 | Isaacson et al. |
| 5,803,910 A | 9/1998 | Potratz |
| 5,807,246 A | 9/1998 | Sakaguchi et al. |

| | | | | | | |
|---|---|---|---|---|---|---|
| 5,807,247 A | 9/1998 | Merchant et al. | 6,229,856 B1 | 5/2001 | Diab et al. | |
| 5,810,723 A | 9/1998 | Aldrich | 6,230,035 B1 | 5/2001 | Aoyagi et al. | |
| 5,810,724 A | 9/1998 | Gronvall | 6,232,609 B1 | 5/2001 | Snyder et al. | |
| 5,810,734 A | 9/1998 | Caro et al. | 6,236,872 B1 | 5/2001 | Diab et al. | |
| 5,817,010 A | 10/1998 | Hibl | 6,241,683 B1 | 6/2001 | Macklem et al. | |
| 5,818,985 A | 10/1998 | Merchant et al. | 6,253,097 B1 | 6/2001 | Aronow et al. | |
| 5,823,950 A | 10/1998 | Diab et al. | 6,256,523 B1 | 7/2001 | Diab et al. | |
| 5,823,952 A | 10/1998 | Levinson et al. | 6,262,698 B1 * | 7/2001 | Blum .............................. | 345/55 |
| 5,827,182 A | 10/1998 | Raley | 6,263,222 B1 | 7/2001 | Diab et al. | |
| 5,830,131 A | 11/1998 | Caro et al. | 6,272,363 B1 | 8/2001 | Casciani et al. | |
| 5,830,137 A | 11/1998 | Sharf | 6,278,522 B1 | 8/2001 | Lepper, Jr. et al. | |
| 5,833,618 A | 11/1998 | Caro et al. | 6,280,213 B1 | 8/2001 | Tobler et al. | |
| 5,839,439 A | 11/1998 | Nierlich et al. | 6,285,895 B1 | 9/2001 | Ristolainen et al. | |
| RE36,000 E | 12/1998 | Swedlow et al. | 6,285,896 B1 | 9/2001 | Tobler et al. | |
| 5,842,979 A | 12/1998 | Jarman | 6,298,252 B1 | 10/2001 | Kovach et al. | |
| 5,851,178 A | 12/1998 | Aronow | 6,304,675 B1 | 10/2001 | Osbourn et al. | |
| 5,851,179 A | 12/1998 | Ritson et al. | 6,304,767 B1 | 10/2001 | Soller et al. | |
| 5,853,364 A | 12/1998 | Baker, Jr. et al. | 6,321,100 B1 | 11/2001 | Parker | |
| 5,857,462 A | 1/1999 | Thomas et al. | 6,330,468 B1 | 12/2001 | Scharf | |
| 5,860,919 A | 1/1999 | Kiani-Azarbayjany et al. | 6,334,065 B1 | 12/2001 | Al-Ali et al. | |
| 5,865,736 A | 2/1999 | Baker, Jr. et al. | 6,341,257 B1 | 1/2002 | Haaland | |
| 5,876,348 A | 3/1999 | Sugo | 6,343,224 B1 | 1/2002 | Parker | |
| 5,885,213 A | 3/1999 | Richardson et al. | 6,349,228 B1 | 2/2002 | Kiani et al. | |
| 5,890,929 A | 4/1999 | Mills et al. | 6,351,658 B1 | 2/2002 | Middleman et al. | |
| 5,891,022 A | 4/1999 | Pologe | 6,356,774 B1 | 3/2002 | Bernstein et al. | |
| 5,891,024 A | 4/1999 | Jarman et al. | 6,360,113 B1 | 3/2002 | Dettling | |
| 5,904,654 A | 5/1999 | Wohltmann et al. | 6,360,114 B1 | 3/2002 | Diab et al. | |
| 5,910,108 A | 6/1999 | Solenberger | 6,363,269 B1 | 3/2002 | Hanna et al. | |
| 5,916,154 A | 6/1999 | Hobbs et al. | 6,368,283 B1 | 4/2002 | Xu et al. | |
| 5,919,133 A | 7/1999 | Taylor | 6,371,921 B1 | 4/2002 | Caro et al. | |
| 5,919,134 A | 7/1999 | Diab | 6,374,129 B1 | 4/2002 | Chin et al. | |
| 5,921,921 A | 7/1999 | Potratz et al. | 6,377,828 B1 | 4/2002 | Chaiken et al. | |
| 5,934,277 A | 8/1999 | Mortz | 6,377,829 B1 | 4/2002 | Al-Ali | |
| 5,934,925 A | 8/1999 | Tobler et al. | 6,388,240 B2 | 5/2002 | Schulz et al. | |
| 5,940,182 A | 8/1999 | Lepper, Jr. et al. | 6,393,310 B1 | 5/2002 | Kuenstner | |
| 5,954,644 A | 9/1999 | Dettling | 6,397,091 B2 | 5/2002 | Diab et al. | |
| 5,978,691 A | 11/1999 | Mills | 6,397,092 B1 | 5/2002 | Norris et al. | |
| 5,983,122 A | 11/1999 | Jarman et al. | 6,397,093 B1 | 5/2002 | Aldrich | |
| 5,995,855 A | 11/1999 | Kiani et al. | 6,408,198 B1 | 6/2002 | Hanna et al. | |
| 5,995,856 A | 11/1999 | Mannheimer et al. | 6,411,833 B1 | 6/2002 | Baker, Jr. et al. | |
| 5,995,859 A | 11/1999 | Takahashi | 6,415,166 B1 | 7/2002 | Van Hoy et al. | |
| 5,997,343 A | 12/1999 | Mills et al. | 6,415,233 B1 | 7/2002 | Haaland | |
| 5,999,841 A | 12/1999 | Aoyagi et al. | 6,415,236 B2 | 7/2002 | Kobayashi et al. | |
| 6,002,952 A | 12/1999 | Diab et al. | 6,430,525 B1 | 8/2002 | Weber et al. | |
| 6,006,119 A | 12/1999 | Soller et al. | 6,434,408 B1 | 8/2002 | Heckel | |
| 6,011,986 A | 1/2000 | Diab et al. | 6,441,388 B1 | 8/2002 | Thomas et al. | |
| 6,014,576 A | 1/2000 | Raley | 6,453,184 B1 | 9/2002 | Hyogo et al. | |
| 6,018,673 A | 1/2000 | Chin et al. | 6,455,340 B1 | 9/2002 | Chua et al. | |
| 6,018,674 A | 1/2000 | Aronow | 6,463,310 B1 | 10/2002 | Swedlow et al. | |
| 6,023,541 A | 2/2000 | Merchant et al. | 6,463,311 B1 | 10/2002 | Diab | |
| 6,027,452 A | 2/2000 | Flaherty et al. | 6,470,199 B1 | 10/2002 | Kopotic et al. | |
| 6,036,642 A | 3/2000 | Diab et al. | 6,480,729 B2 | 11/2002 | Stone | |
| 6,045,509 A | 4/2000 | Caro et al. | 6,490,466 B1 | 12/2002 | Fein et al. | |
| 6,064,898 A | 5/2000 | Aldrich | 6,497,659 B1 | 12/2002 | Rafert | |
| 6,067,462 A | 5/2000 | Diab et al. | 6,501,974 B2 | 12/2002 | Huiku | |
| 6,068,594 A | 5/2000 | Schloemer et al. | 6,501,975 B2 | 12/2002 | Diab et al. | |
| 6,073,037 A | 6/2000 | Alam et al. | 6,504,943 B1 | 1/2003 | Sweatt et al. | |
| 6,081,735 A | 6/2000 | Diab et al. | 6,505,059 B1 | 1/2003 | Kollias et al. | |
| 6,083,172 A | 7/2000 | Baker, Jr. et al. | 6,505,060 B1 | 1/2003 | Norris | |
| 6,088,607 A | 7/2000 | Diab et al. | 6,505,061 B2 | 1/2003 | Larson | |
| 6,094,592 A | 7/2000 | Yorkey et al. | 6,505,133 B1 | 1/2003 | Hanna | |
| 6,104,938 A | 8/2000 | Huiku | 6,510,329 B2 | 1/2003 | Heckel | |
| 6,110,522 A | 8/2000 | Lepper, Jr. et al. | 6,515,273 B2 | 2/2003 | Al-Ali | |
| 6,112,107 A | 8/2000 | Hannula | 6,519,486 B1 | 2/2003 | Edgar, Jr. et al. | |
| 6,122,042 A | 9/2000 | Wunderman et al. | 6,519,487 B1 | 2/2003 | Parker | |
| 6,124,597 A | 9/2000 | Shehada et al. | 6,522,398 B2 | 2/2003 | Cadell et al. | |
| 6,144,868 A | 11/2000 | Parker | 6,525,386 B1 | 2/2003 | Mills et al. | |
| 6,149,588 A | 11/2000 | Noda et al. | 6,526,300 B1 | 2/2003 | Kiani et al. | |
| 6,151,516 A | 11/2000 | Kiani-Azarbayjany et al. | 6,526,301 B2 | 2/2003 | Larsen et al. | |
| 6,151,518 A | 11/2000 | Hayashi | 6,528,809 B1 | 3/2003 | Thomas et al. | |
| 6,152,754 A | 11/2000 | Gerhardt et al. | 6,537,225 B1 | 3/2003 | Mills | |
| 6,154,667 A | 11/2000 | Miura et al. | 6,541,756 B2 | 4/2003 | Schulz et al. | |
| 6,157,041 A | 12/2000 | Thomas et al. | 6,542,763 B1 | 4/2003 | Yamashita et al. | |
| 6,157,850 A | 12/2000 | Diab et al. | 6,542,764 B1 | 4/2003 | Al-Ali et al. | |
| 6,165,005 A | 12/2000 | Mills et al. | 6,545,652 B1 | 4/2003 | Tsuji | |
| 6,184,521 B1 | 2/2001 | Coffin, IV et al. | 6,546,267 B1 | 4/2003 | Sugiura | |
| 6,192,261 B1 | 2/2001 | Gratton et al. | 6,553,241 B2 | 4/2003 | Mannheimer et al. | |
| 6,206,830 B1 | 3/2001 | Diab et al. | 6,564,077 B2 | 5/2003 | Mortara | |
| 6,226,539 B1 | 5/2001 | Potratz | 6,571,113 B1 | 5/2003 | Fein et al. | |

| Patent | Date | Inventor |
|---|---|---|
| 6,580,086 B1 | 6/2003 | Schulz et al. |
| 6,582,964 B1 | 6/2003 | Samsoondar et al. |
| 6,584,336 B1 | 6/2003 | Ali et al. |
| 6,584,413 B1 | 6/2003 | Keenan et al. |
| 6,591,123 B2 | 7/2003 | Fein et al. |
| 6,594,511 B2 | 7/2003 | Stone et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,600,940 B1 | 7/2003 | Fein et al. |
| 6,606,509 B2 | 8/2003 | Schmitt |
| 6,606,510 B2 | 8/2003 | Swedlow et al. |
| 6,606,511 B1 | 8/2003 | Ali et al. |
| 6,611,698 B1 | 8/2003 | Yamashita et al. |
| 6,614,521 B2 | 9/2003 | Samsoondar et al. |
| 6,615,064 B1 | 9/2003 | Aldrich |
| 6,615,151 B1 | 9/2003 | Scecina et al. |
| 6,618,602 B2 | 9/2003 | Levin |
| 6,622,095 B2 | 9/2003 | Kobayashi et al. |
| 6,628,975 B1 | 9/2003 | Fein et al. |
| 6,631,281 B1 | 10/2003 | Kastle |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,623 B1 | 11/2003 | Kastle |
| 6,654,624 B2 | 11/2003 | Diab et al. |
| 6,657,717 B2 | 12/2003 | Cadell et al. |
| 6,658,276 B2 | 12/2003 | Kianl et al. |
| 6,658,277 B2 | 12/2003 | Wasserman |
| 6,661,161 B1 | 12/2003 | Lanzo et al. |
| 6,662,033 B2 | 12/2003 | Casciani et al. |
| 6,665,551 B1 | 12/2003 | Suzuki |
| 6,668,183 B2 | 12/2003 | Hicks et al. |
| 6,671,526 B1 | 12/2003 | Aoyagi et al. |
| 6,671,531 B2 | 12/2003 | Al-Ali et al. |
| 6,675,031 B1 | 1/2004 | Porges et al. |
| 6,675,106 B1 | 1/2004 | Keenan et al. |
| 6,678,543 B2 | 1/2004 | Diab et al. |
| 6,681,126 B2 | 1/2004 | Solenberger |
| 6,684,090 B2 | 1/2004 | Ali et al. |
| 6,684,091 B2 | 1/2004 | Parker |
| 6,687,620 B1 | 2/2004 | Haaland et al. |
| 6,690,466 B2 | 2/2004 | Miller et al. |
| 6,694,157 B1 | 2/2004 | Stone et al. |
| 6,697,655 B2 | 2/2004 | Sueppel et al. |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,701,170 B2 | 3/2004 | Stetson |
| 6,708,049 B1 | 3/2004 | Berson et al. |
| 6,711,503 B2 | 3/2004 | Haaland |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,705 B2 | 4/2004 | Mills |
| 6,720,734 B2 | 4/2004 | Norris |
| 6,721,582 B2 | 4/2004 | Trepagnier et al. |
| 6,721,584 B2 | 4/2004 | Baker, Jr. et al. |
| 6,721,585 B1 | 4/2004 | Parker |
| 6,725,074 B1 | 4/2004 | Kastle |
| 6,725,075 B2 | 4/2004 | Al-Ali |
| 6,726,634 B2 | 4/2004 | Freeman |
| 6,728,560 B2 | 4/2004 | Kollias et al. |
| 6,735,459 B2 | 5/2004 | Parker |
| 6,741,875 B1 | 5/2004 | Pawluczyk et al. |
| 6,741,876 B1 | 5/2004 | Scecina et al. |
| 6,743,172 B1 | 6/2004 | Blike |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neil et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,788,849 B1 | 9/2004 | Pawluczyk |
| 6,792,300 B1 | 9/2004 | Diab et al. |
| 6,800,373 B2 | 10/2004 | Corczyca |
| 6,801,797 B2 | 10/2004 | Mannheimer et al. |
| 6,801,799 B2 | 10/2004 | Mendelson |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,829,501 B2 | 12/2004 | Nielsen et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,842,702 B2 | 1/2005 | Haaland et al. |
| 6,845,256 B2 | 1/2005 | Chin et al. |
| 6,847,835 B1 | 1/2005 | Yamanishi |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,861,641 B1 | 3/2005 | Adams |
| 6,869,402 B2 | 3/2005 | Arnold |
| 6,882,874 B2 | 4/2005 | Huiku |
| 6,898,452 B2 | 5/2005 | Al-Ali et al. |
| 6,912,049 B2 | 6/2005 | Pawluczyk et al. |
| 6,917,422 B2 | 7/2005 | Samsoondar et al. |
| 6,919,566 B1 | 7/2005 | Cadell |
| 6,920,345 B2 | 7/2005 | Al-Ali et al. |
| 6,921,367 B2 | 7/2005 | Mills |
| 6,922,645 B2 | 7/2005 | Haaland et al. |
| 6,928,311 B1 | 8/2005 | Pawluczyk et al. |
| 6,931,268 B1 | 8/2005 | Kiani-Azarbayjany et al. |
| 6,931,269 B2 | 8/2005 | Terry |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,944,487 B2 | 9/2005 | Maynard et al. |
| 6,950,687 B2 | 9/2005 | Al-Ali |
| 6,961,598 B2 | 11/2005 | Diab |
| 6,970,792 B1 | 11/2005 | Diab |
| 6,975,891 B2 | 12/2005 | Pawluczyk |
| 6,979,812 B2 | 12/2005 | Al-Ali |
| 6,985,764 B2 | 1/2006 | Mason et al. |
| 6,987,994 B1 | 1/2006 | Mortz |
| 6,993,371 B2 | 1/2006 | Kiani et al. |
| 6,996,427 B2 | 2/2006 | Ali et al. |
| 6,999,904 B2 | 2/2006 | Weber et al. |
| 7,001,337 B2 | 2/2006 | Dekker |
| 7,003,338 B2 | 2/2006 | Weber et al. |
| 7,003,339 B2 | 2/2006 | Diab et al. |
| 7,006,856 B2 | 2/2006 | Baker, Jr. et al. |
| 7,015,451 B2 | 3/2006 | Dalke et al. |
| 7,024,233 B2 | 4/2006 | Al et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab et al. |

| | | |
|---|---|---|
| 7,215,986 B2 | 5/2007 | Diab et al. |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,299,080 B2 | 11/2007 | Acosta et al. |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,957,780 B2 | 6/2011 | Lamego et al. |
| 2001/0044700 A1 | 11/2001 | Kobayashi et al. |
| 2001/0045532 A1 | 11/2001 | Schulz et al. |
| 2002/0021269 A1* | 2/2002 | Rast .................. 345/82 |
| 2002/0026107 A1* | 2/2002 | Kiani et al. ............ 600/310 |
| 2002/0035318 A1 | 3/2002 | Mannheimer et al. |
| 2002/0038078 A1 | 3/2002 | Ito |
| 2002/0038081 A1 | 3/2002 | Fein et al. |
| 2002/0059047 A1 | 5/2002 | Haaland |
| 2002/0082488 A1 | 6/2002 | Al-Ali et al. |
| 2002/0095078 A1 | 7/2002 | Mannheimer et al. |
| 2002/0111748 A1 | 8/2002 | Kobayashi et al. |
| 2002/0115919 A1 | 8/2002 | Al-Ali |
| 2002/0154665 A1 | 10/2002 | Funabashi et al. |
| 2002/0156353 A1 | 10/2002 | Larson |
| 2002/0159002 A1 | 10/2002 | Chang |
| 2002/0161291 A1 | 10/2002 | Kianl et al. |
| 2002/0165440 A1 | 11/2002 | Mason et al. |
| 2002/0183819 A1* | 12/2002 | Struble .................. 607/122 |
| 2003/0045784 A1 | 3/2003 | Palatnik et al. |
| 2003/0045785 A1 | 3/2003 | Diab et al. |
| 2003/0049232 A1 | 3/2003 | Page et al. |
| 2003/0109775 A1 | 6/2003 | O'Neil et al. |
| 2003/0116769 A1 | 6/2003 | Song et al. |
| 2003/0117296 A1 | 6/2003 | Seely |
| 2003/0120160 A1 | 6/2003 | Yarita |
| 2003/0120164 A1 | 6/2003 | Nielsen et al. |
| 2003/0135099 A1 | 7/2003 | Al-Ali |
| 2003/0139657 A1 | 7/2003 | Solenberger |
| 2003/0160257 A1 | 8/2003 | Bader et al. |
| 2003/0195402 A1 | 10/2003 | Fein et al. |
| 2004/0006261 A1 | 1/2004 | Swedlow et al. |
| 2004/0033618 A1 | 2/2004 | Haass et al. |
| 2004/0059209 A1 | 3/2004 | Ali et al. |
| 2004/0064259 A1 | 4/2004 | Haaland et al. |
| 2004/0081621 A1 | 4/2004 | Arndt et al. |
| 2004/0092805 A1 | 5/2004 | Yarita |
| 2004/0133087 A1 | 7/2004 | Ali et al. |
| 2004/0138538 A1 | 7/2004 | Stetson |
| 2004/0138540 A1 | 7/2004 | Baker, Jr. et al. |
| 2004/0147822 A1 | 7/2004 | Al-Ali et al. |
| 2004/0147823 A1* | 7/2004 | Kiani et al. ............ 600/323 |
| 2004/0158132 A1 | 8/2004 | Zaleski |
| 2004/0158134 A1 | 8/2004 | Diab et al. |
| 2004/0158135 A1 | 8/2004 | Baker, Jr. et al. |
| 2004/0162472 A1 | 8/2004 | Berson et al. |
| 2004/0167382 A1 | 8/2004 | Gardner et al. |
| 2004/0176670 A1 | 9/2004 | Takamura et al. |
| 2004/0181134 A1 | 9/2004 | Baker, Jr. et al. |
| 2004/0199063 A1 | 10/2004 | O'Neil et al. |
| 2004/0204639 A1 | 10/2004 | Casciani et al. |
| 2004/0204868 A1 | 10/2004 | Maynard et al. |
| 2004/0229391 A1 | 11/2004 | Ohya et al. |
| 2004/0262046 A1 | 12/2004 | Simon et al. |
| 2004/0267103 A1 | 12/2004 | Li et al. |
| 2004/0267140 A1 | 12/2004 | Ito et al. |
| 2005/0031340 A1 | 2/2005 | Ali et al. |
| 2005/0033128 A1 | 2/2005 | Ali et al. |
| 2005/0043902 A1 | 2/2005 | Haaland et al. |
| 2005/0049469 A1 | 3/2005 | Aoyagi et al. |
| 2005/0054908 A1 | 3/2005 | Blank et al. |
| 2005/0070773 A1 | 3/2005 | Chin et al. |
| 2005/0070775 A1 | 3/2005 | Chin et al. |
| 2005/0075546 A1 | 4/2005 | Samsoondar et al. |
| 2005/0085735 A1 | 4/2005 | Baker, Jr. et al. |
| 2005/0124871 A1 | 6/2005 | Baker, Jr. et al. |
| 2005/0143634 A1 | 6/2005 | Baker, Jr. et al. |
| 2005/0143943 A1 | 6/2005 | Brown |
| 2005/0148834 A1 | 7/2005 | Hull et al. |
| 2005/0184895 A1 | 8/2005 | Petersen et al. |
| 2005/0187447 A1 | 8/2005 | Chew et al. |
| 2005/0187448 A1 | 8/2005 | Petersen et al. |
| 2005/0187449 A1 | 8/2005 | Chew et al. |
| 2005/0187450 A1 | 8/2005 | Chew et al. |
| 2005/0187452 A1 | 8/2005 | Petersen et al. |
| 2005/0187453 A1 | 8/2005 | Petersen et al. |
| 2005/0197549 A1 | 9/2005 | Baker, Jr. |
| 2005/0197579 A1 | 9/2005 | Baker, Jr. |
| 2005/0197793 A1 | 9/2005 | Baker, Jr. |
| 2005/0203357 A1 | 9/2005 | Debreczeny et al. |
| 2005/0209515 A1 | 9/2005 | Hockersmith et al. |
| 2005/0228253 A1 | 10/2005 | Debreczeny |
| 2005/0250997 A1 | 11/2005 | Takedo et al. |
| 2006/0030764 A1 | 2/2006 | Porges et al. |
| 2006/0210120 A1 | 9/2006 | Rowe et al. |
| 2006/0211922 A1 | 9/2006 | Al-Ali et al. |
| 2006/0211923 A1 | 9/2006 | Al-Ali et al. |
| 2006/0211924 A1 | 9/2006 | Smith et al. |
| 2006/0211925 A1 | 9/2006 | Lamego et al. |
| 2006/0211932 A1 | 9/2006 | Al-Ali et al. |
| 2006/0226992 A1 | 10/2006 | Al-Ali et al. |
| 2006/0229509 A1 | 10/2006 | Al-Ali et al. |
| 2006/0238358 A1 | 10/2006 | Al-Ali et al. |
| 2006/0241358 A1 | 10/2006 | Al-Ali et al. |
| 2006/0241363 A1 | 10/2006 | Al-Ali et al. |

FOREIGN PATENT DOCUMENTS

| | | |
|---|---|---|
| EP | 0 569 670 | 2/1993 |
| EP | 0 675 541 | 10/1995 |
| EP | 1 895 892 | 5/2010 |
| EP | 2 305 104 | 4/2011 |
| JP | 61-28172 | 2/1986 |
| JP | 64-500495 | 2/1989 |
| JP | 2-145457 | 12/1990 |
| JP | 6-237013 | 8/1994 |
| JP | 7-281618 | 10/1995 |
| JP | 9-192120 | 7/1997 |
| JP | 10-509352 | 9/1998 |
| JP | 10-269344 A | 10/1998 |
| JP | 11-163412 | 6/1999 |
| JP | 11-183377 | 7/1999 |
| JP | 2002-525151 | 8/2002 |
| JP | 2003-507718 | 2/2003 |
| JP | 2003-084108 | 3/2003 |
| JP | 2003-521985 | 7/2003 |
| JP | 2004-070179 | 3/2004 |
| JP | 2004-226277 | 8/2004 |
| JP | 2004-296736 | 10/2004 |
| JP | 2004-327760 | 11/2004 |
| JP | 2005-501589 | 1/2005 |
| JP | 2005-253478 | 9/2005 |

| | | |
|---|---|---|
| WO | WO 88/01150 | 2/1988 |
| WO | WO 88/02020 | 2/1988 |
| WO | WO 92/16142 | 10/1992 |
| WO | WO 96/13208 | 5/1996 |
| WO | WO 97/01985 | 1/1997 |
| WO | WO 98/43071 | 10/1998 |
| WO | WO 00/18290 | 4/2000 |
| WO | WO 00/42911 A1 | 7/2000 |
| WO | WO 00/59374 | 10/2000 |
| WO | WO 01/13790 | 3/2001 |
| WO | WO 01/58347 | 8/2001 |
| WO | WO 02/26123 | 4/2002 |
| WO | WO 02/089664 | 11/2002 |
| WO | WO 03/020129 | 3/2003 |
| WO | WO 03/068060 | 8/2003 |
| WO | WO 2004/034898 | 4/2004 |
| WO | WO 2005/011488 | 2/2005 |

OTHER PUBLICATIONS

Schmitt, Joseph M.; Zhou, Guan-Xiong; Miller, Justin, *Measurement of Blood Hematocrit by Dual-Wavelength Near-IR Photoplethysmography*, published May 1992, Proc. SPIE vol. 1641, p. 150-161, Physiological Monitoring and Early Detection Diagnostice Methods, Thomas S. Mang; Ed. (SPIE homepage), in 12 pages.
Patent Cooperation Treaty (PCT) International Search Report; PCT/US 2006/007389; Date of Mailing Jul. 17, 2006; pp. 1-9.
PCT International Search Report; PCT/US2006/007537; Date of Mailing Jul. 17, 2006; pp. 1-10.
PCT International Search Report; PCT/US2006/007388; Date of Mailing Jul. 17, 2006; pp. 1-9.
PCT International Search Report; PCT/US2006/007538; Date of Mailing Jul. 17, 2006; pp. 1-9.
PCT International Search Report; PCT/US2006/007958; Date of Mailing Jul. 17, 2006; pp. 1-8.
PCT International Search Report; PCT/US2006/007506; Date of Mailing Jul. 17, 2006; pp. 1-10.
PCT International Search Report; PCT/US2006/007536; Date of Mailing Jul. 17, 2006; pp. 1-9.
PCT International Search Report; PCT/US2006/007540; Date of Mailing Jul. 17, 2006; pp. 1-9.
PCT International Search Report; PCT/US2006/007539; Date of Mailing Jul. 17, 2006; pp. 1-9.
PCT International Search Report; PCT/US2006/007387; Date of Mailing Jul. 17, 2006; pp. 1-9.
Burritt, Mary F.; Current Analytical Approaches to Measuring Blood Analytes; vol. 36; No. 8(B); 1990.
European Examination Report dated Mar. 18, 2011, re EP App. No. 08 744 412.1 - 2319.
European Examination Report dated Sep. 2, 2010, re EP App. No. 08 744 412.1 - 2319.
European Extended Search Report re EPO App. No. 10162402.1, SR dated Aug. 9, 2010.
Hall, et al., Jeffrey W.; Near-Infrared Spectrophotometry: A New Dimension in Clinical Chemistry; vol. 38; No. 9; 1992.
Japanese First Office Action (Notice of Reasons for Rejection), re JP App. No. 2007-558207, dated Jun. 28, 2011.
Japanese First Office Action (Notice of Reasons for Rejection), re JP App. No. 2007-558247, dated Jun. 28, 2011.
Japanese Office Action (Notice of Reasons for Rejection) re JP App. No. 2007-558246, dated Jun. 28, 2011.
Japanese Office Action (Notice of Reasons for Rejection), re JP App. No. 2007-558238, dated Jun. 28, 2011.
Japanese Office Action re JP Application No. 2007-558249, dated Jul. 13, 2011.
Kuenstner, et al., J. Todd; Measurement of Hemoglobin in Unlysed Blood by Near-Infrared Spectroscopy; vol. 48; No. 4, 1994.
Manzke, et al., B., Multi Wavelength Pulse OXimetry in the Measurement of Hemoglobin Fractions; vol. 2676, date unknown.
Naumenko, E. K.; Choice of Wavelengths for Stable Determination of Concentrations of Hemoglobin Derivatives from Absorption Spectra of Erythrocytes; vol. 63; No. 1; pp. 60-66 Jan.-Feb. 1996; Original article submitted Nov. 3, 1994.
PCT Search Report of International Application No. PCT/US2008/058327, Mailing Date of Jun. 30, 2009, in 12 pages.
PCT Search Report of International Application No. PCT/US2008/058327, Mailing Date of Aug. 12, 2008, in 6 pages.
Schmitt, Joseph M.; Simple Photon Diffusion Anaylsis of the Effects of Multiple Scattering on Pulse Oximetry; Mar. 14, 1991; revised Aug. 30, 1991.
Schnapp, et al., L.M.; Pulse Oximetry. Uses and Abuses.; Chest 1990; 98; 1244-125000110.1378/Chest.98.5.1244.

* cited by examiner

DETAIL A-A

SECTION A-A

SECTION B-B

SECTION A-A

SECTION B-B

SECTION A-A

SECTION B-B

SECTION A-A

SECTION B-B

SECTION A-A

SECTION B-B

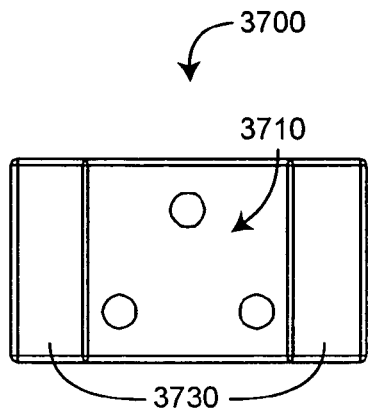
FIG. 37A
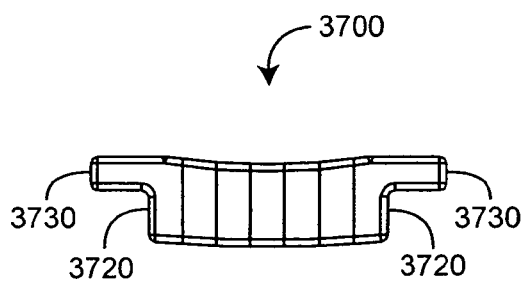 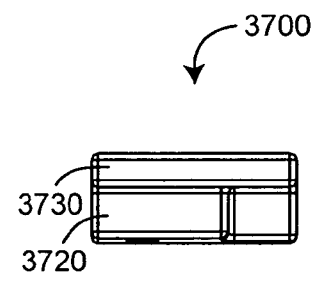
FIG. 37B          FIG. 37D
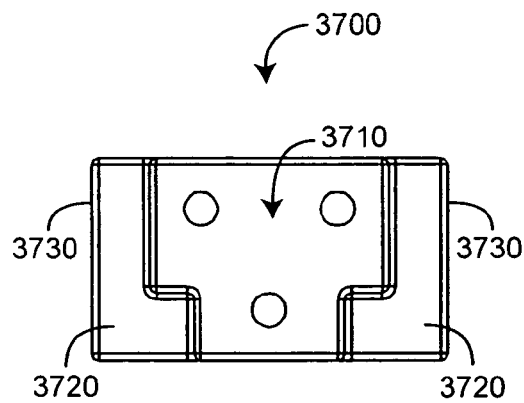
FIG. 37C

SECTION B-B

SECTION A-A

SECTION A-A

MULTIPLE WAVELENGTH SENSOR DRIVERS

PRIORITY CLAIM TO RELATED PROVISIONAL APPLICATIONS

The present application claims priority benefit under 35 U.S.C. §119(e) to U.S. Provisional Patent Application Ser. No. 60/657,596, filed Mar. 1, 2005, entitled "Multiple Wavelength Sensor," No. 60/657,281, filed Mar. 1, 2005, entitled "Physiological Parameter Confidence Measure," No. 60/657,268, filed Mar. 1, 2005, entitled "Configurable Physiological Measurement System," and No. 60/657,759, filed Mar. 1, 2005, entitled "Noninvasive Multi-Parameter Patient Monitor." The present application incorporates the foregoing disclosures herein by reference.

INCORPORATION BY REFERENCE OF COPENDING RELATED APPLICATIONS

The present application is related to the following copending U.S. utility applications:

| | application Ser. No. | Filing Date | Title |
|---|---|---|---|
| 1 | 11/367,013 | Mar. 1, 2006 | Multiple Wavelength Sensor Emitters |
| 2 | 11/366,995 | Mar. 1, 2006 | Multiple Wavelength Sensor Equalization |
| 3 | 11/366,209 | Mar. 1, 2006 | Multiple Wavelength Sensor Substrate |
| 4 | 11/366,210 | Mar. 1, 2006 | Multiple Wavelength Sensor Interconnect |
| 5 | 11/366,833 | Mar. 1, 2006 | Multiple Wavelength Sensor Attachment |
| 6 | 11/367,034 | Mar. 1, 2006 | Physiological Parameter Confidence Measure |
| 7 | 11/367,036 | Mar. 1, 2006 | Configurable Physiological Measurement System |
| 8 | 11/367,033 | Mar. 1, 2006 | Noninvasive Multi-Parameter Patient Monitor |
| 9 | 11/367,014 | Mar. 1, 2006 | Noninvasive Multi-Parameter Patient Monitor |
| 10 | 11/366,208 | Mar. 1, 2006 | Noninvasive Multi-Parameter Patient Monitor |

The present application incorporates the foregoing disclosures herein by reference.

BACKGROUND OF THE INVENTION

Spectroscopy is a common technique for measuring the concentration of organic and some inorganic constituents of a solution. The theoretical basis of this technique is the Beer-Lambert law, which states that the concentration $c_i$ of an absorbent in solution can be determined by the intensity of light transmitted through the solution, knowing the pathlength $d_\lambda$, the intensity of the incident light $I_{0,\lambda}$, and the extinction coefficient $\epsilon_{i,\lambda}$ at a particular wavelength $\lambda$. In generalized form, the Beer-Lambert law is expressed as:

$$I_\lambda = I_{0,\lambda} e^{-d_\lambda \cdot \mu_{a,\lambda}} \tag{1}$$

$$\mu_{a,\lambda} = \sum_{i=1}^{n} \epsilon_{i,\lambda} \cdot c_i \tag{2}$$

where $\mu_{a,\lambda}$ is the bulk absorption coefficient and represents the probability of absorption per unit length. The minimum number of discrete wavelengths that are required to solve EQS. 1-2 are the number of significant absorbers that are present in the solution.

A practical application of this technique is pulse oximetry, which utilizes a noninvasive sensor to measure oxygen saturation ($SpO_2$) and pulse rate. In general, the sensor has light emitting diodes (LEDs) that transmit optical radiation of red and infrared wavelengths into a tissue site and a detector that responds to the intensity of the optical radiation after absorption (e.g., by transmission or transreflectance) by pulsatile arterial blood flowing within the tissue site. Based on this response, a processor determines measurements for $SpO_2$, pulse rate, and can output representative plethysmographic waveforms. Thus, "pulse oximetry" as used herein encompasses its broad ordinary meaning known to one of skill in the art, which includes at least those noninvasive procedures for measuring parameters of circulating blood through spectroscopy. Moreover, "plethysmograph" as used herein (commonly referred to as "photoplethysmograph"), encompasses its broad ordinary meaning known to one of skill in the art, which includes at least data representative of a change in the absorption of particular wavelengths of light as a function of the changes in body tissue resulting from pulsing blood. Pulse oximeters capable of reading through motion induced noise are available from Masimo Corporation ("Masimo") of Irvine, Calif. Moreover, portable and other oximeters capable of reading through motion induced noise are disclosed in at least U.S. Pat. Nos. 6,770,028, 6,658,276, 6,157,850, 6,002,952 5,769,785, and 5,758,644, which are owned by Masimo and are incorporated by reference herein. Such reading through motion oximeters have gained rapid acceptance in a wide variety of medical applications, including surgical wards, intensive care and neonatal units, general wards, home care, physical training, and virtually all types of monitoring scenarios.

SUMMARY OF THE INVENTION

There is a need to noninvasively measure multiple physiological parameters, other than, or in addition to, oxygen saturation and pulse rate. For example, hemoglobin species that are also significant under certain circumstances are carboxyhemoglobin and methemoglobin. Other blood parameters that may be measured to provide important clinical information are fractional oxygen saturation, total hemoglobin (Hbt), bilirubin and blood glucose, to name a few.

One aspect of a sensor driver is a cable capable of communicating signals between a physiological sensor and a monitor is a first row input, a first column input, a second row input and a second column input. The cable is capable of activating individual light emitters of an emitter array arranged in an electrical grid by driving at least one row drive line and at least one column drive line of the electrical grid. A first output combines the first row input and the first column input. A second output combines the second row input and the second column input. The inputs are adapted to connect to electrical grid drive lines of a monitor. Further, the outputs are adapted to connect to contacts of a physiological sensor having back-to-back configured LEDs in electrical communication with the contacts.

Another aspect of a sensor driver is an electrical grid configured to activate light emitting sources by addressing at least one row conductor and at least one column conductor. A first LED and a second LED are configured in a back-to-back arrangement so that a first contact is connected to a first LED cathode and a second LED anode and a second contact is connected to a first LED anode and a second LED cathode. The first contact is in communications with a first row conductor and a first column conductor. The second contact is in communications with a second row conductor and a second column conductor. Further, the first LED is activated by addressing the first row conductor and the second column conductor and the second LED is activated by addressing the second row conductor and the first column conductor.

A further aspect of a sensor driver is an electrical grid drive having at least a portion of the electrical grid drive communicated to a physiological sensor. The electrical grid drive is adapted to activate back-to-back configured LEDs.

BRIEF DESCRIPTION OF THE DRAWINGS

FIGS. 37A-D are top, back, bottom, and side views of a spring plate;

DETAILED DESCRIPTION OF THE PREFERRED EMBODIMENTS

Overview

In this application, reference is made to many blood parameters. Some references that have common shorthand designations are referenced through such shorthand designations. For example, as used herein, HbCO designates carboxyhemoglobin, HbMet designates methemoglobin, and Hbt designates total hemoglobin. Other shorthand designations such as COHb, MetHb, and tHb are also common in the art for these same constituents. These constituents are generally reported in terms of a percentage, often referred to as saturation, relative concentration or fractional saturation. Total hemoglobin is generally reported as a concentration in g/dL. The use of the particular shorthand designators presented in this application does not restrict the term to any particular manner in which the designated constituent is reported.

Figure 1:
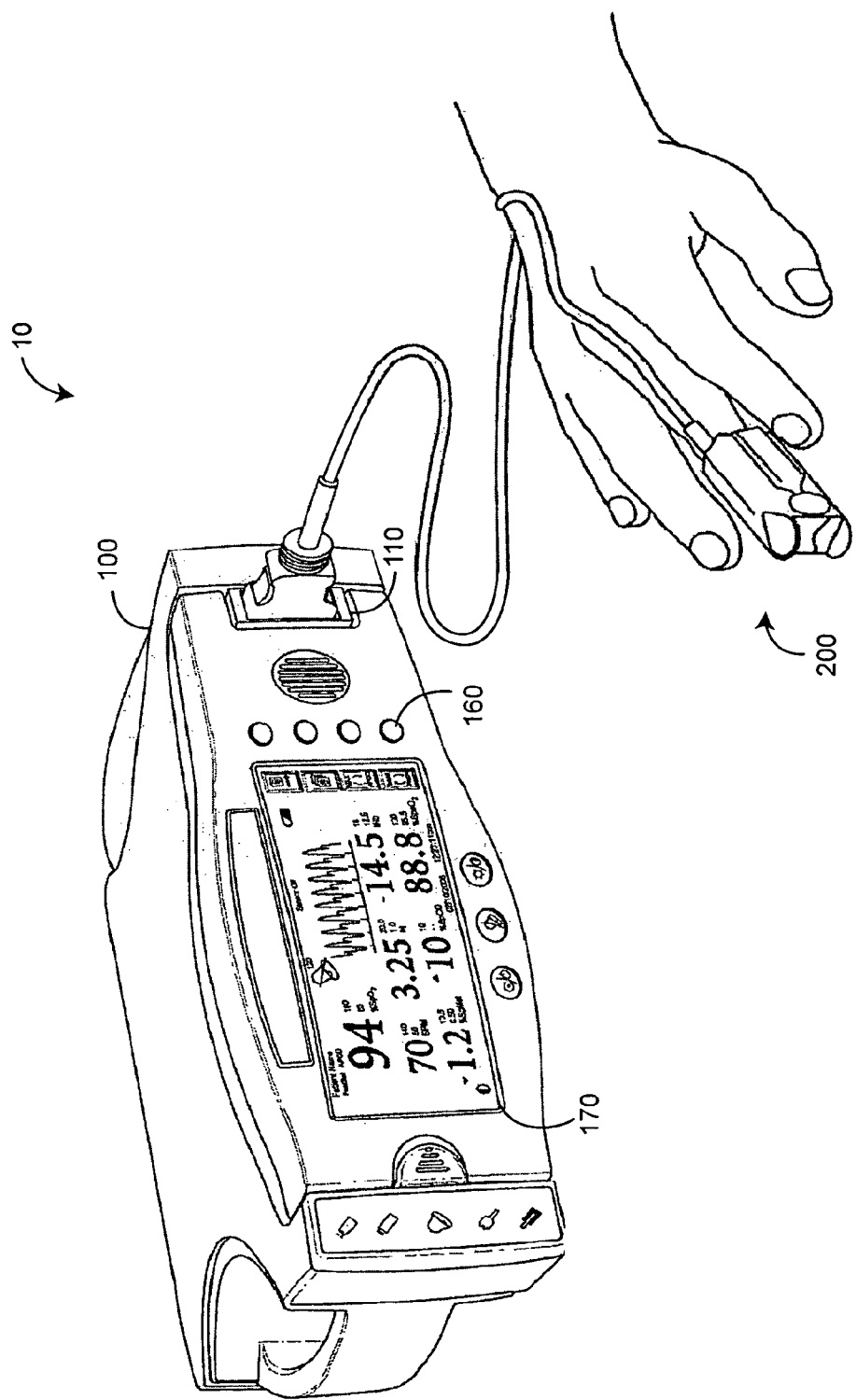
FIG. 1 is a perspective view of a physiological measurement system utilizing a multiple wavelength sensor.

FIG. 1 illustrates a physiological measurement system 10 having a monitor 100 and a multiple wavelength sensor assembly 200 with enhanced measurement capabilities as compared with conventional pulse oximetry. The physiological measurement system 10 allows the monitoring of a person, including a patient. In particular, the multiple wavelength sensor assembly 200 allows the measurement of blood constituent and related parameters in addition to oxygen saturation and pulse rate. Alternatively, the multiple wavelength sensor assembly 200 allows the measurement of oxygen saturation and pulse rate with increased accuracy or robustness as compared with conventional pulse oximetry.

In one embodiment, the sensor assembly 200 is configured to plug into a monitor sensor port 110. Monitor keys 160 provide control over operating modes and alarms, to name a few. A display 170 provides readouts of measured parameters, such as oxygen saturation, pulse rate, HbCO and HbMet to name a few.

Figure 2A:
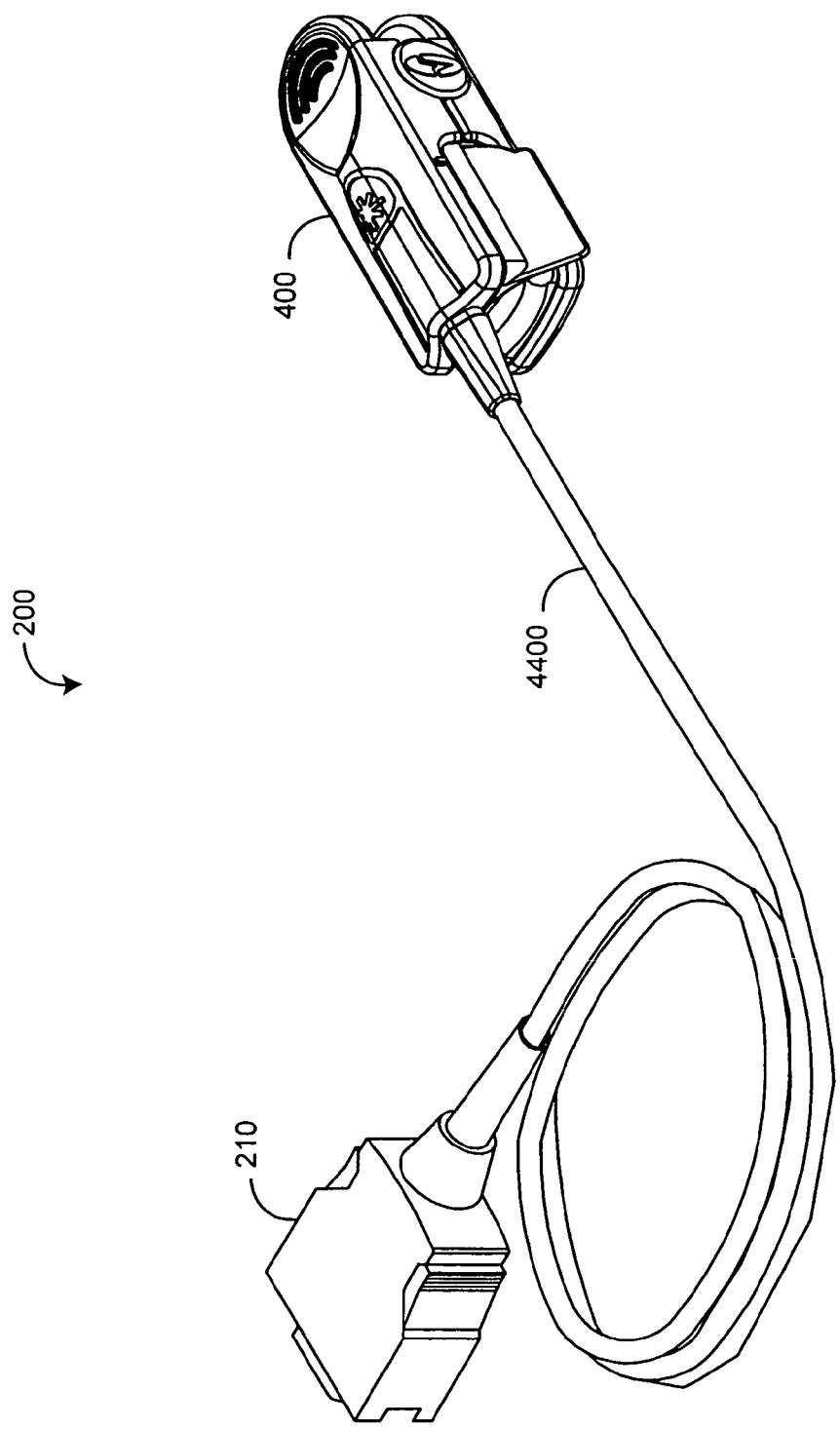
FIGS. 2A-C are perspective views of multiple wavelength sensor embodiments.

FIG. 2A illustrates a multiple wavelength sensor assembly 200 having a sensor 400 adapted to attach to a tissue site, a sensor cable 4400 and a monitor connector 210. In one embodiment, the sensor 400 is incorporated into a reusable finger clip adapted to removably attach to, and transmit light through, a fingertip. The sensor cable 4400 and monitor connector 210 are integral to the sensor 400, as shown. In alternative embodiments, the sensor 400 may be configured separately from the cable 4400 and connector 210.

Figure 2B:
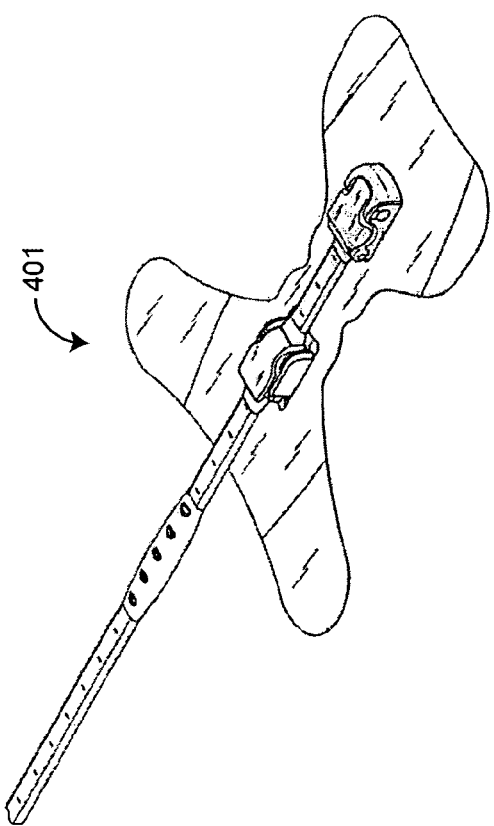
Figure 2C:
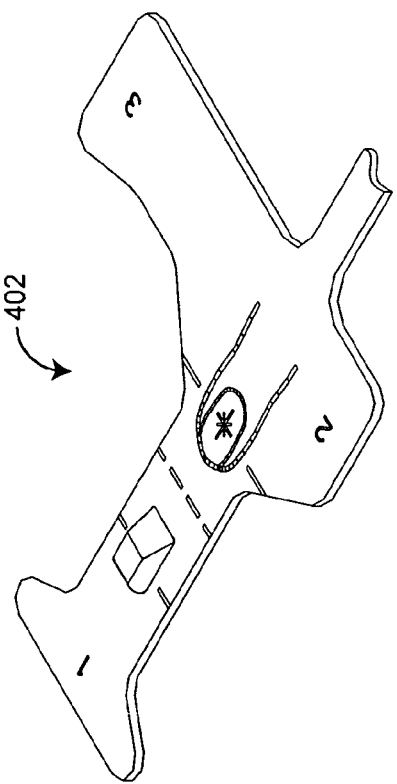

FIGS. 2B-C illustrate alternative sensor embodiments, including a sensor 401 (FIG. 2B) partially disposable and partially reusable (resposable) and utilizing an adhesive attachment mechanism. Also shown is a sensor 402 (FIG. 2C) being disposable and utilizing an adhesive attachment mechanism. In other embodiments, a sensor may be configured to attach to various tissue sites other than a finger, such as a foot or an ear. Also a sensor may be configured as a reflectance or transflectance device that attaches to a forehead or other tissue surface.

Figure 3:
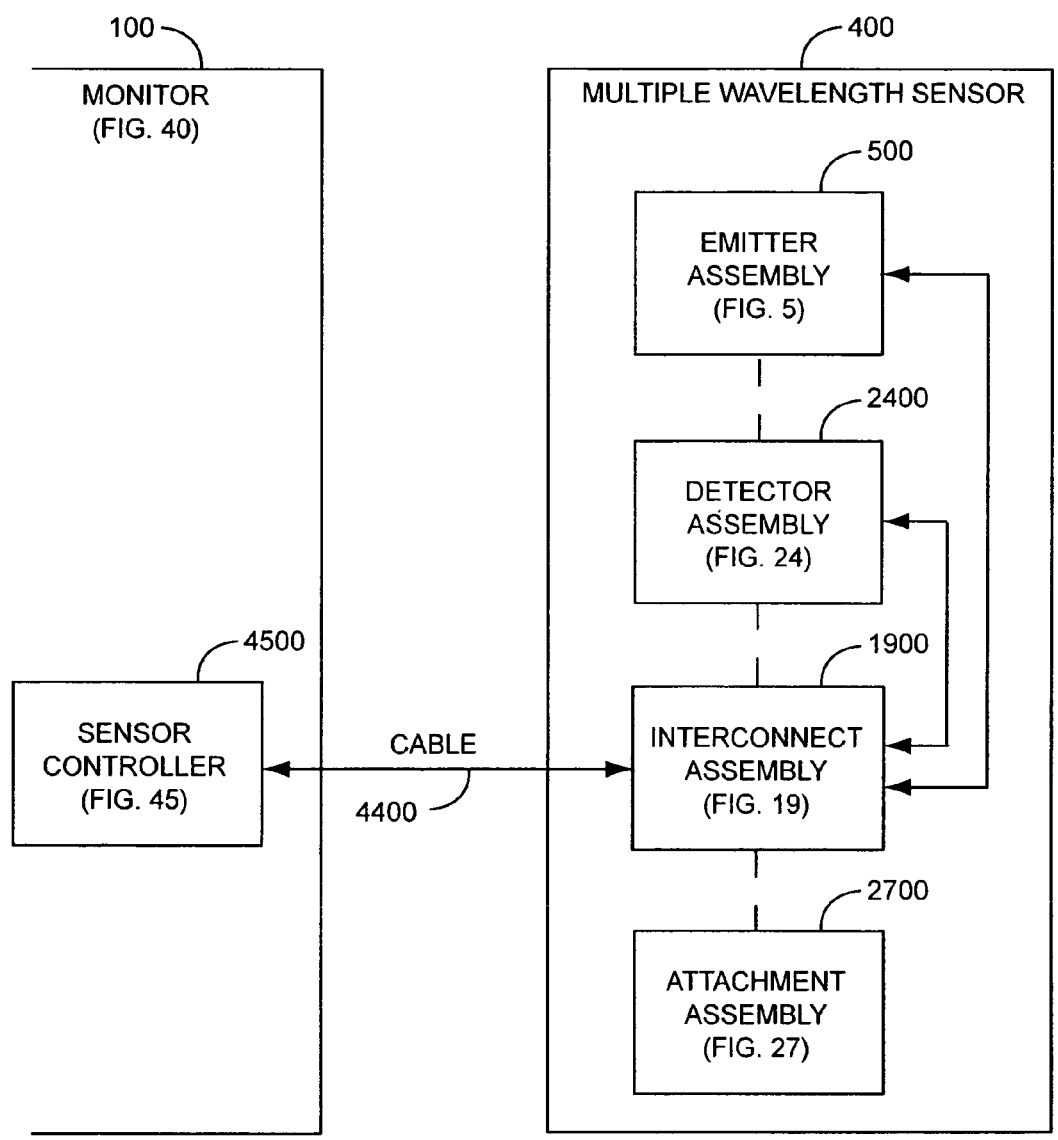
FIG. 3 is a general block diagram of a multiple wavelength sensor and sensor controller.

FIG. 3 illustrates a sensor assembly 400 having an emitter assembly 500, a detector assembly 2400, an interconnect assembly 1900 and an attachment assembly 2700. The emitter assembly 500 responds to drive signals received from a sensor controller 4500 in the monitor 100 via the cable 4400 so as to transmit optical radiation having a plurality of wavelengths into a tissue site. The detector assembly 2400 provides a sensor signal to the monitor 100 via the cable 4400 in response to optical radiation received after attenuation by the tissue site. The interconnect assembly 1900 provides electrical communication between the cable 4400 and both the emitter assembly 500 and the detector assembly 2400. The attachment assembly 2700 attaches the emitter assembly 500 and detector assembly 2400 to a tissue site, as described above. The emitter assembly 500 is described in further detail with respect to FIG. 5, below. The interconnect assembly 1900 is described in further detail with respect to FIG. 19, below. The detector assembly 2400 is described in further detail with respect to FIG. 24, below. The attachment assembly 2700 is described in further detail with respect to FIG. 27, below.

Figure 4:
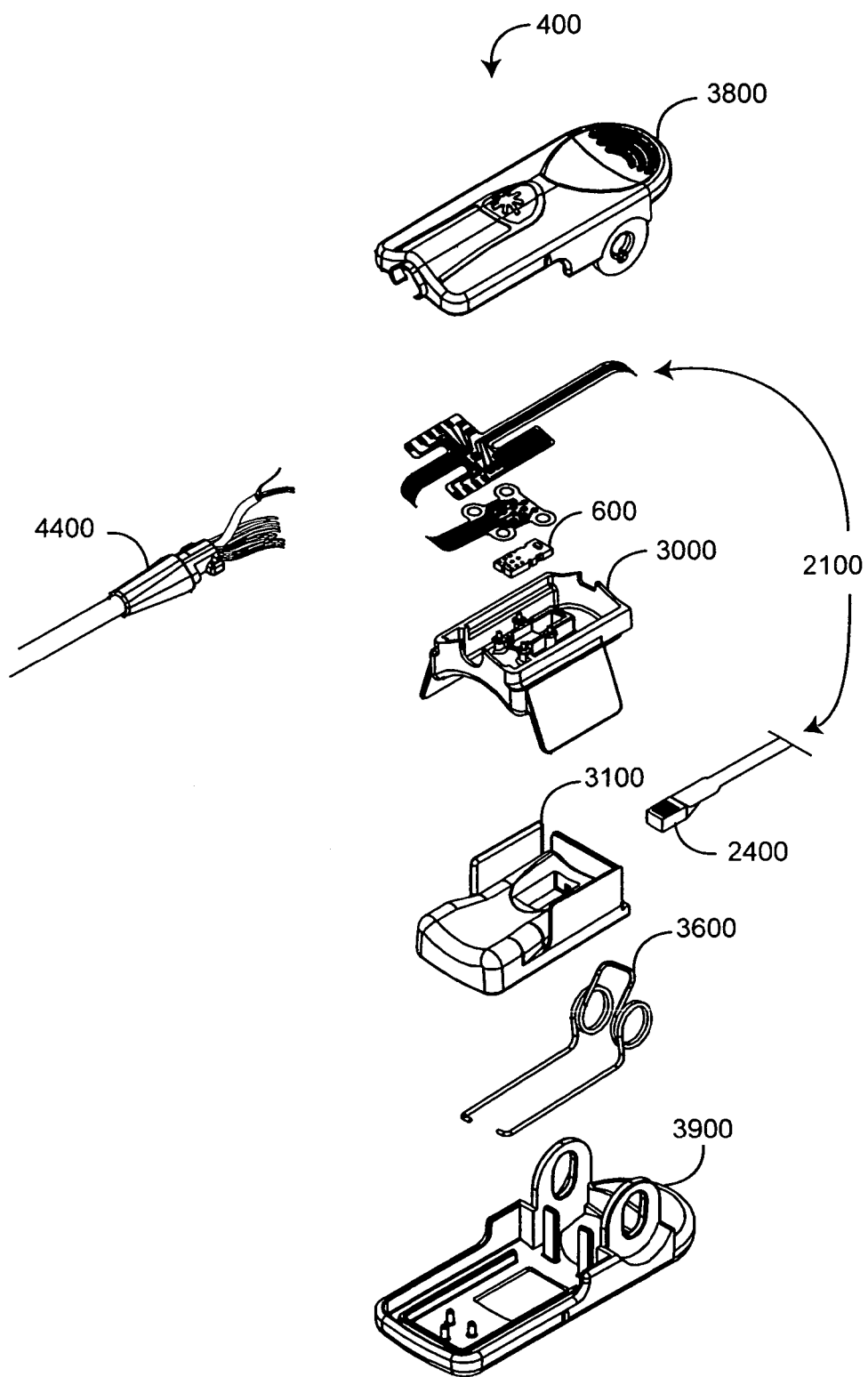
FIG. 4 is an exploded perspective view of a multiple wavelength sensor embodiment.

FIG. 4 illustrates a sensor 400 embodiment that removably attaches to a fingertip. The sensor 400 houses a multiple wavelength emitter assembly 500 and corresponding detector assembly 2400. A flex circuit assembly 1900 mounts the emitter and detector assemblies 500, 2400 and interconnects them to a multi-wire sensor cable 4400. Advantageously, the sensor 400 is configured in several respects for both wearer comfort and parameter measurement performance. The flex circuit assembly 1900 is configured to mechanically decouple the cable 4400 wires from the emitter and detector assemblies 500, 2400 to reduce pad stiffness and wearer discomfort. The pads 3000, 3100 are mechanically decoupled from shells 3800, 3900 to increase flexibility and wearer comfort. A spring 3600 is configured in hinged shells 3800, 3900 so that the pivot point of the finger clip is well behind the fingertip, improving finger attachment and more evenly distributing the clip pressure along the finger.

As shown in FIG. 4, the detector pad 3100 is structured to properly position a fingertip in relationship to the detector assembly 2400. The pads have flaps that block ambient light. The detector assembly 2400 is housed in an enclosure so as to reduce light piping from the emitter assembly to the detector assembly without passing through fingertip tissue. These and other features are described in detail below. Specifically, emitter assembly embodiments are described with respect to FIGS. 5-18. Interconnect assembly embodiments, including the flexible circuit assembly 1900, are described with respect to FIGS. 19-23. Detector assembly embodiments are described with respect to FIGS. 24-26. Attachment assembly embodiments are described with respect to FIGS. 27-39.

Emitter Assembly

Figure 5:
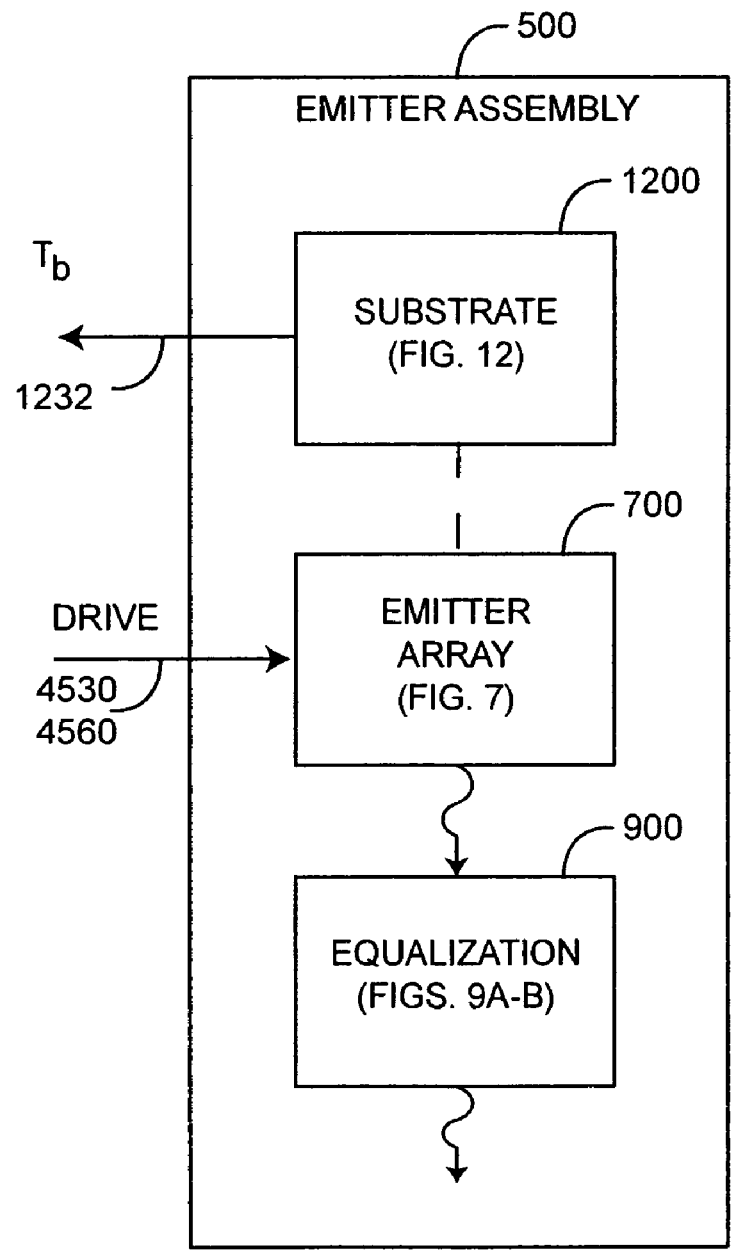
FIG. 5 is a general block diagram of an emitter assembly.

FIG. 5 illustrates an emitter assembly 500 having an emitter array 700, a substrate 1200 and equalization 900. The emitter array 700 has multiple light emitting sources, each activated by addressing at least one row and at least one column of an electrical grid. The light emitting sources are capable of transmitting optical radiation having multiple wavelengths. The equalization 900 accounts for differences in tissue attenuation of the optical radiation across the multiple wavelengths so as to at least reduce wavelength-dependent variations in detected intensity. The substrate 1200 provides a physical mount for the emitter array and emitter-related equalization and a connection between the emitter array and the interconnection assembly. Advantageously, the substrate 1200 also provides a bulk temperature measurement so as to calculate the operating wavelengths for the light emitting sources. The emitter array 700 is described in further detail with respect to FIG. 7, below. Equalization is described in further detail with respect to FIG. 9, below. The substrate 1200 is described in further detail with respect to FIG. 12, below.

Figure 6:
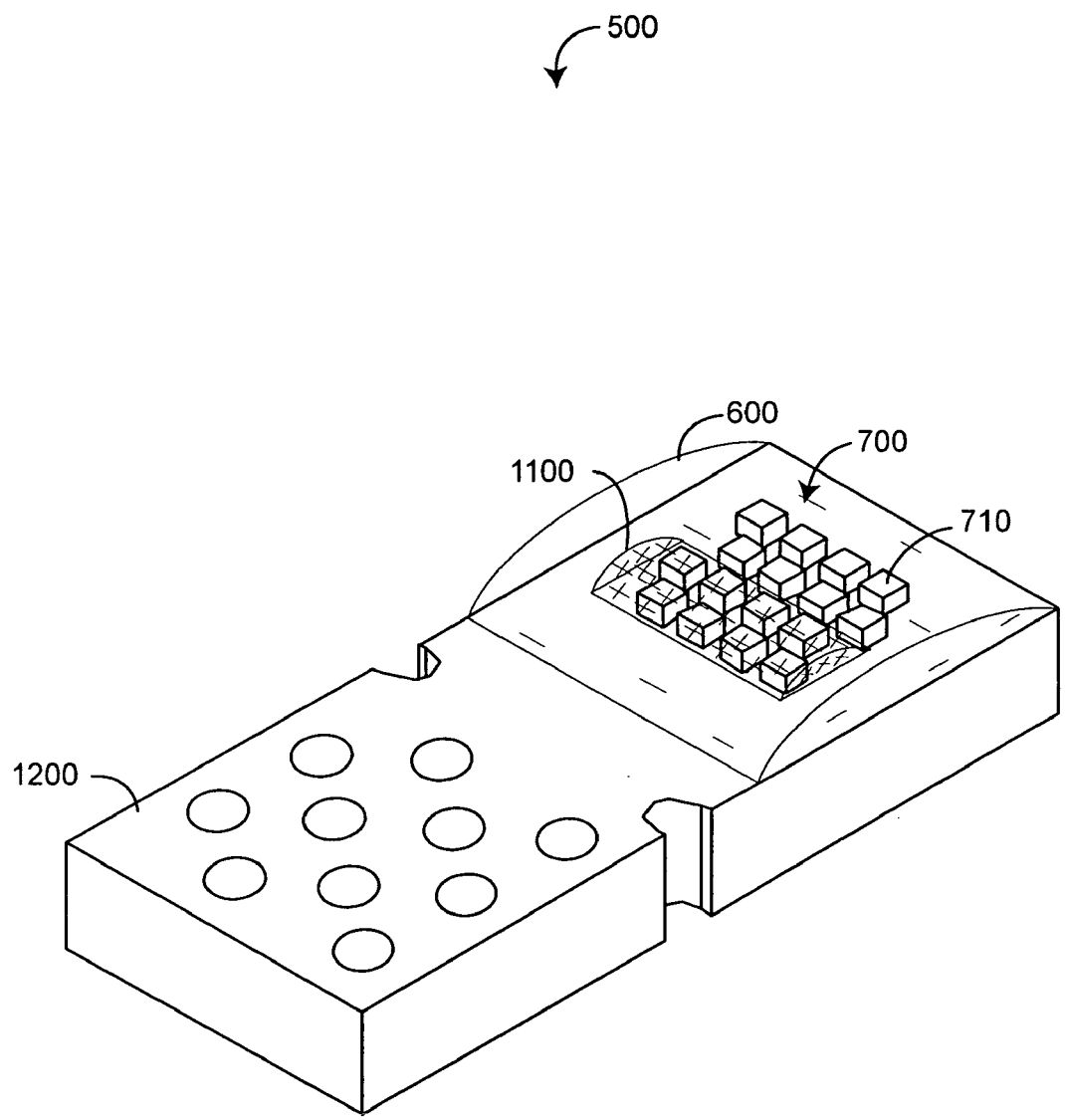
FIG. 6 is a perspective view of an emitter assembly embodiment.

FIG. 6 illustrates an emitter assembly 500 embodiment having an emitter array 700, an encapsulant 600, an optical filter 1100 and a substrate 1200. Various aspects of the emitter assembly 500 are described with respect to FIGS. 7-18, below. The emitter array 700 emits optical radiation having multiple wavelengths of predetermined nominal values, advantageously allowing multiple parameter measurements. In particular, the emitter array 700 has multiple light emitting diodes (LEDs) 710 that are physically arranged and electrically connected in an electrical grid to facilitate drive control, equalization, and minimization of optical pathlength differences at particular wavelengths. The optical filter 1100 is advantageously configured to provide intensity equalization across a specific LED subset. The substrate 1200 is configured to provide a bulk temperature of the emitter array 700 so as to better determine LED operating wavelengths.

Emitter Array

Figure 7:
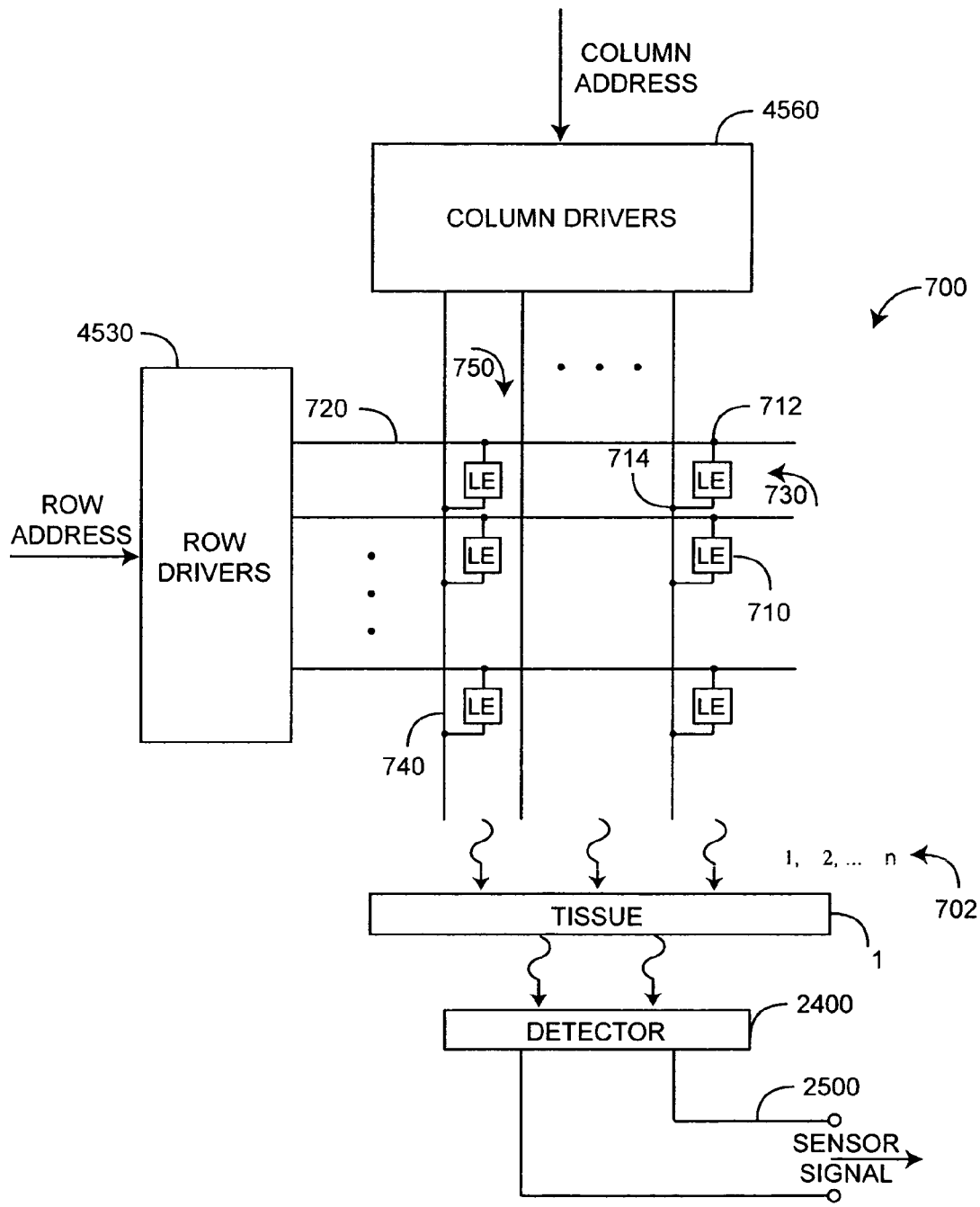
FIG. 7 is a general block diagram of an emitter array.

FIG. 7 illustrates an emitter array 700 having multiple light emitters (LE) 710 capable of emitting light 702 having multiple wavelengths into a tissue site 1. Row drivers 4530 and column drivers 4560 are electrically connected to the light emitters 710 and activate one or more light emitters 710 by addressing at least one row 720 and at least one column 740 of an electrical grid. In one embodiment, the light emitters 710 each include a first contact 712 and a second contact 714. The first contact 712 of a first subset 730 of light emitters is in communication with a first conductor 720 of the electrical grid. The second contact 714 of a second subset 750 of light emitters is in communication with a second conductor 740. Each subset comprises at least two light emitters, and at least one of the light emitters of the first and second subsets 730, 750 are not in common. A detector 2400 is capable of detecting the emitted light 702 and outputting a sensor signal 2500 responsive to the emitted light 702 after attenuation by the tissue site 1. As such, the sensor signal 2500 is indicative of at least one physiological parameter corresponding to the tissue site 1, as described above.

Figure 8:
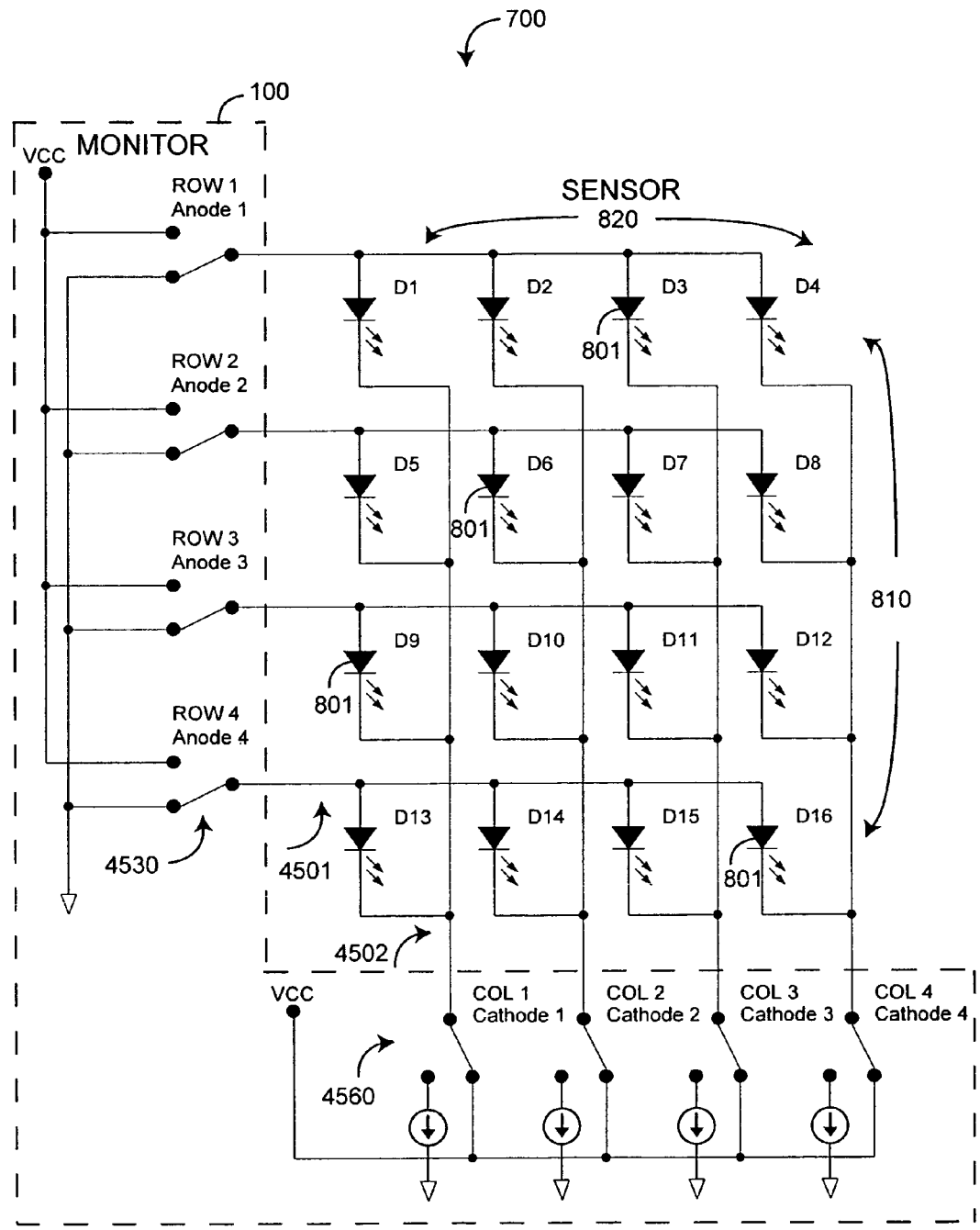
FIG. 8 is a schematic diagram of an emitter array embodiment.

FIG. 8 illustrates an emitter array 700 having LEDs 801 connected within an electrical grid of n rows and m columns totaling n+m drive lines 4501, 4502, where n and m integers greater than one. The electrical grid advantageously minimizes the number of drive lines required to activate the LEDs 801 while preserving flexibility to selectively activate individual LEDs 801 in any sequence and multiple LEDs 801 simultaneously. The electrical grid also facilitates setting LED currents so as to control intensity at each wavelength, determining operating wavelengths and monitoring total grid current so as to limit power dissipation. The emitter array 700 is also physically configured in rows 810. This physical organization facilitates clustering LEDs 801 according to wavelength so as to minimize pathlength variations and facilitates equalization of LED intensities.

As shown in FIG. 8, one embodiment of an emitter array 700 comprises up to sixteen LEDs 801 configured in an electrical grid of four rows 810 and four columns 820. Each of the four row drive lines 4501 provide a common anode connection to four LEDs 801, and each of the four column drive lines 4502 provide a common cathode connection to four LEDs 801. Thus, the sixteen LEDs 801 are advantageously driven with only eight wires, including four anode drive lines 812 and four cathode drive lines 822. This compares favorably to conventional common anode or cathode LED configurations, which require more drive lines. In a particular embodiment, the emitter array 700 is partially populated with eight LEDs having nominal wavelengths as shown in TABLE 1. Further, LEDs having wavelengths in the range of 610-630 nm are grouped together in the same row. The emitter array 700 is adapted to a physiological measurement system 10 (FIG. 1) for measuring $H_bCO$ and/or METHb in addition to $S_pO_2$ and pulse rate.

TABLE 1

Nominal LED Wavelengths

| LED | λ | Row | Col |
|-----|-----|-----|-----|
| D1 | 630 | 1 | 1 |
| D2 | 620 | 1 | 2 |
| D3 | 610 | 1 | 3 |
| D4 |  | 1 | 4 |
| D5 | 700 | 2 | 1 |
| D6 | 730 | 2 | 2 |
| D7 | 660 | 2 | 3 |
| D8 | 805 | 2 | 4 |
| D9 |  | 3 | 1 |
| D10 |  | 3 | 2 |
| D11 |  | 3 | 3 |
| D12 | 905 | 3 | 4 |
| D13 |  | 4 | 1 |
| D14 |  | 4 | 2 |
| D15 |  | 4 | 3 |
| D16 |  | 4 | 4 |

Also shown in FIG. 8, row drivers 4530 and column drivers 4560 located in the monitor 100 selectively activate the LEDs 801. In particular, row and column drivers 4530, 4560 function together as switches to Vcc and current sinks, respectively, to activate LEDs and as switches to ground and Vcc, respectively, to deactivate LEDs. This push-pull drive configuration advantageously prevents parasitic current flow in deactivated LEDs. In a particular embodiment, only one row drive line 4501 is switched to Vcc at a time. One to four column drive lines 4502, however, can be simultaneously switched to a current sink so as to simultaneously activate multiple LEDs within a particular row. Activation of two or more LEDs of the same wavelength facilitates intensity equalization, as described with respect to FIGS. 9-11, below. LED drivers are described in further detail with respect to FIG. 45, below.

Although an emitter assembly is described above with respect to an array of light emitters each configured to transmit optical radiation centered around a nominal wavelength, in another embodiment, an emitter assembly advantageously utilizes one or more tunable broadband light sources, including the use of filters to select the wavelength, so as to minimize wavelength-dependent pathlength differences from emitter to detector. In yet another emitter assembly embodiment, optical radiation from multiple emitters each configured to transmit optical radiation centered around a nominal wavelength is funneled to a tissue site point so as to minimize wavelength-dependent pathlength differences. This funneling may be accomplish with fiberoptics or mirrors, for example. In further embodiments, the LEDs 801 can be configured with alternative orientations with correspondingly different drivers among various other configurations of LEDs, drivers and interconnecting conductors.

Equalization

Figure 9:
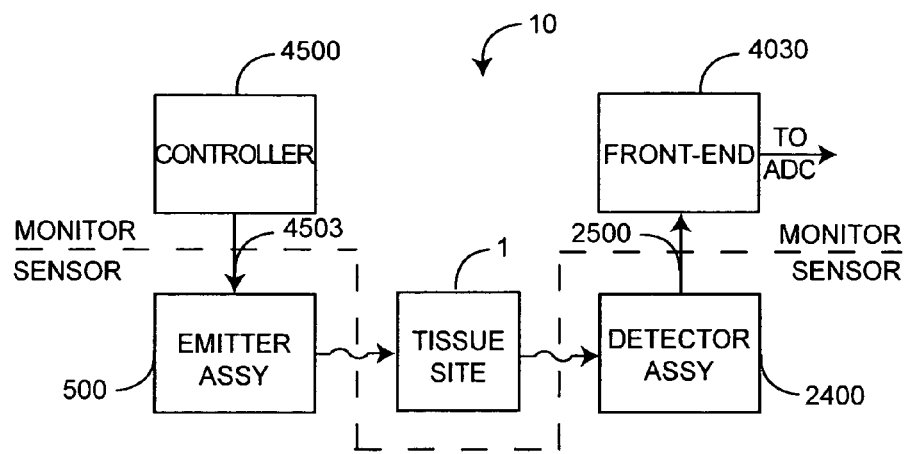
FIG. 9 is a general block diagram of equalization.
Figure 9:
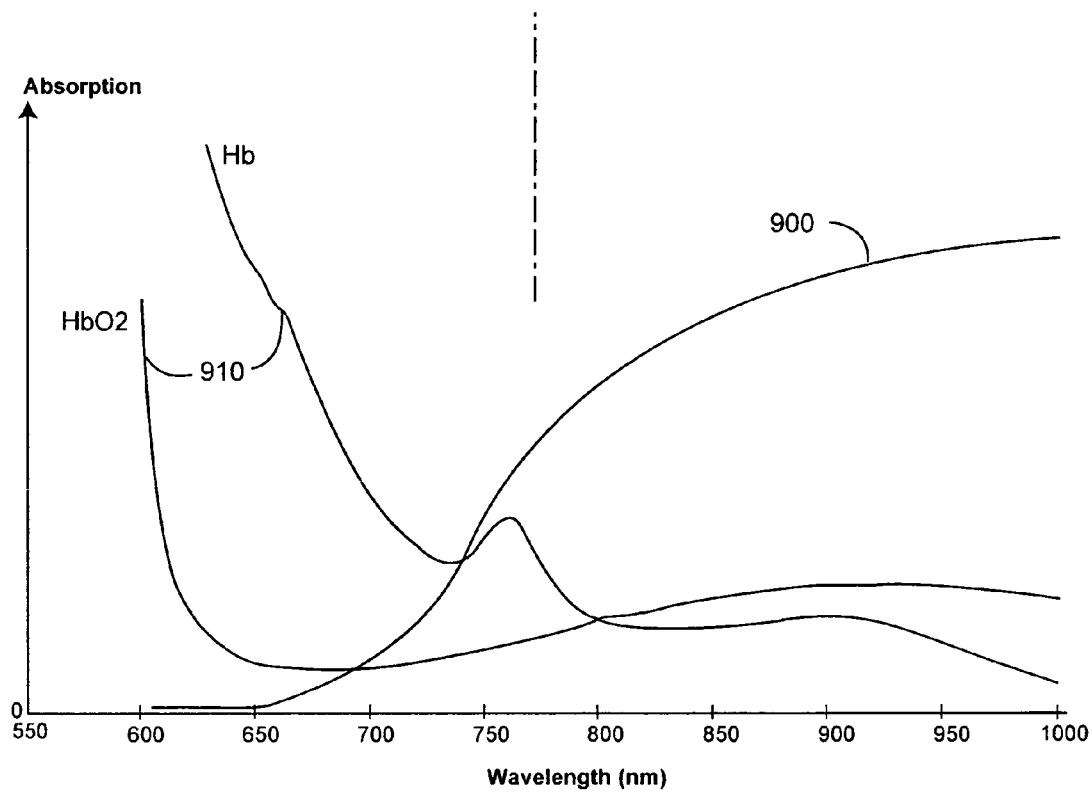

FIG. 9 illustrate a physiological parameter measurement system 10 having a controller 4500, an emitter assembly 500, a detector assembly 2400 and a front-end 4030. The emitter assembly 500 is configured to transmit optical radiation having multiple wavelengths into the tissue site 1. The detector assembly 2400 is configured to generate a sensor signal 2500 responsive to the optical radiation after tissue attenuation. The front-end 4030 conditions the sensor signal 2500 prior to analog-to-digital conversion (ADC).

FIG. 9 also generally illustrates equalization 900 in a physiological measurement system 10 operating on a tissue site 1. Equalization encompasses features incorporated into the system 10 in order to provide a sensor signal 2500 that falls well within the dynamic range of the ADC across the entire spectrum of emitter wavelengths. In particular, equalization compensates for the imbalance in tissue light absorption due to Hb and $HbO_2$ 910. Specifically, these blood constituents attenuate red wavelengths greater than IR wavelengths. Ideally, equalization 900 balances this unequal attenuation. Equalization 900 can be introduced anywhere in the system 10 from the controller 4500 to front-end 4000 and can include compensatory attenuation versus wavelength, as shown, or compensatory amplification versus or both.

Equalization can be achieved to a limited extent by adjusting drive currents from the controller 4500 and front-end 4030 amplification accordingly to wavelength so as to compensate for tissue absorption characteristics. Signal demodulation constraints, however, limit the magnitude of these adjustments. Advantageously, equalization 900 is also provided along the optical path from emitters 500 to detector 2400. Equalization embodiments are described in further detail with respect to FIGS. 10-11, below.

Figure 10A:
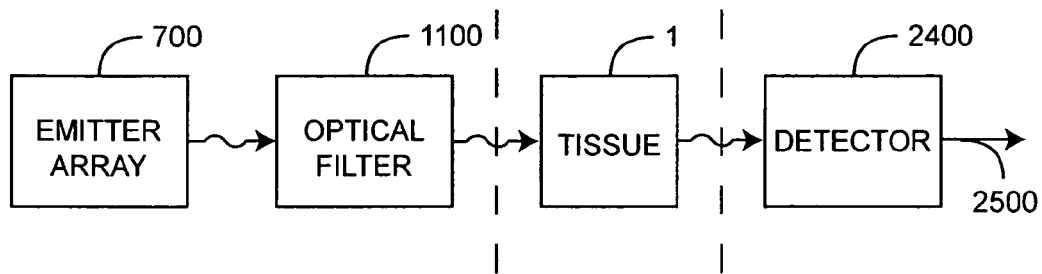
FIGS. 10A-D are block diagrams of various equalization embodiments.
Figure 10B:
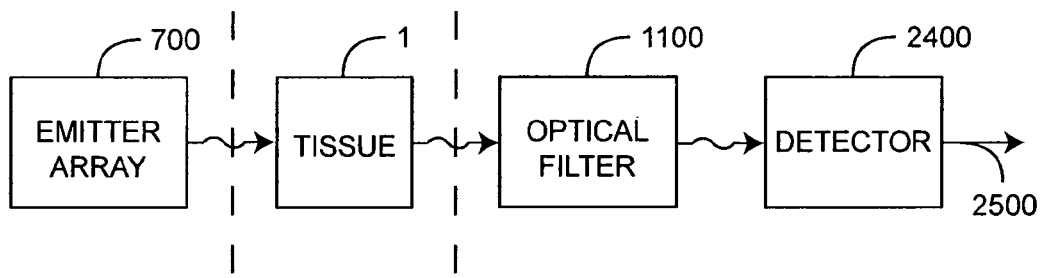

FIGS. 10A-D illustrate various equalization embodiments having an emitter array 700 adapted to transmit optical radiation into a tissue site 1 and a detector assembly 2400 adapted to generate a sensor signal 2500 responsive to the optical radiation after tissue attenuation. FIG. 10A illustrates an optical filter 1100 that attenuates at least a portion of the optical radiation before it is transmitted into a tissue site 1. In particular, the optical filter 1100 attenuates at least a portion of the IR wavelength spectrum of the optical radiation so as to approximate an equalization curve 900 (FIG. 9). FIG. 10B illustrates an optical filter 1100 that attenuates at least a portion of the optical radiation after it is attenuated by a tissue site 1, where the optical filter 1100 approximates an equalization curve 900 (FIG. 9).

Figure 10C:
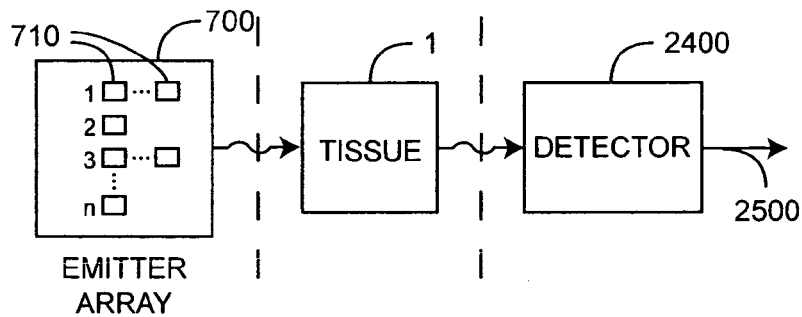
Figure 10D:
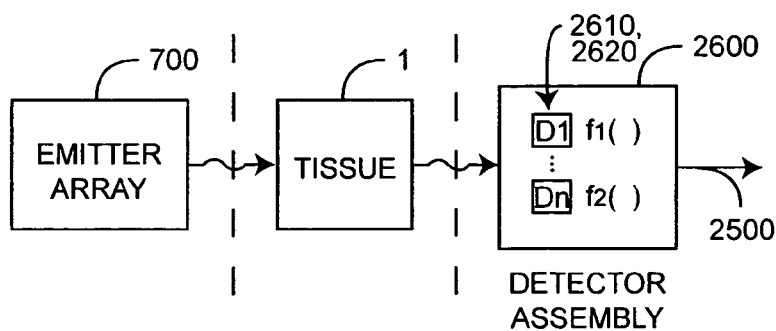

FIG. 10C illustrates an emitter array 700 where at least a portion of the emitter array generates one or more wavelengths from multiple light emitters 710 of the same wavelength. In particular, the same-wavelength light emitters 710 boost at least a portion of the red wavelength spectrum so as to approximately equalize the attenuation curves 910 (FIG. 9). FIG. 10D illustrates a detector assembly 2400 having multiple detectors 2610, 2620 selected so as to equalize the attenuation curves 910 (FIG. 9). To a limited extent, optical equalization can also be achieved by selection of particular emitter array 700 and detector 2400 components, e.g. LEDs having higher output intensities or detectors having higher sensitivities at red wavelengths. Although equalization embodiments are described above with respect to red and IR wavelengths, these equalization embodiments can be applied to equalize tissue characteristics across any portion of the optical spectrum.

Figure 11A:
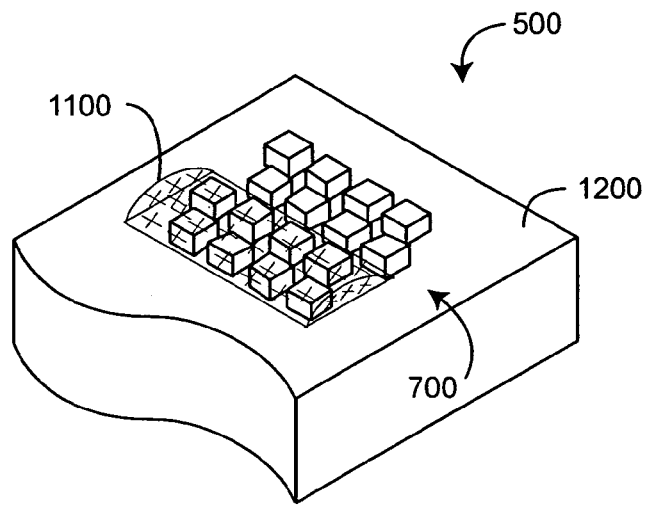
FIGS. 11A-C are perspective views of an emitter assembly incorporating various equalization embodiments.
Figure 11B:
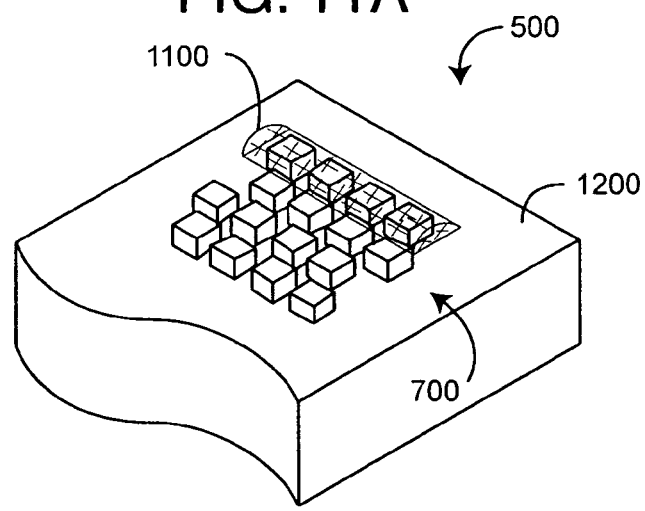
Figure 11C:
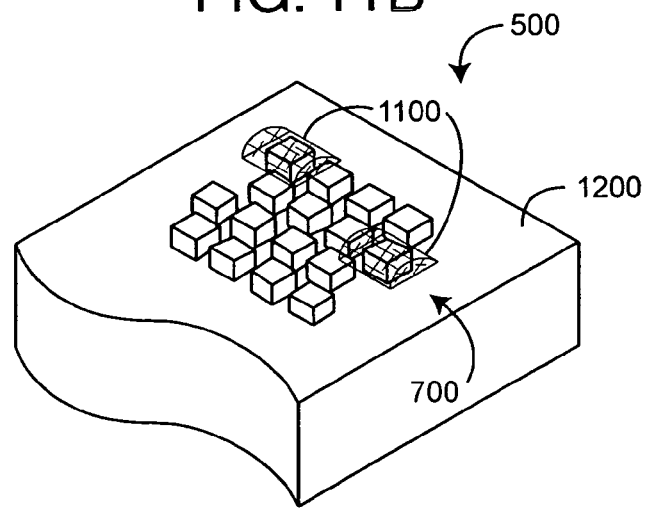

FIGS. 11A-C illustrates an optical filter 1100 for an emitter assembly 500 that advantageously provides optical equalization, as described above. LEDs within the emitter array 700 may be grouped according to output intensity or wavelength or both. Such a grouping facilitates equalization of LED intensity across the array. In particular, relatively low tissue absorption and/or relatively high output intensity LEDs can be grouped together under a relatively high attenuation optical filter. Likewise, relatively low tissue absorption and/or relatively low output intensity LEDs can be grouped together without an optical filter or under a relatively low or negligible attenuation optical filter. Further, high tissue absorption and/or low intensity LEDs can be grouped within the same row with one or more LEDs of the same wavelength being simultaneously activated, as described with respect to FIG. 10C, above. In general, there can be any number of LED groups and any number of LEDs within a group. There can also be any number of optical filters corresponding to the groups having a range of attenuation, including no optical filter and/or a "clear" filter having negligible attenuation.

As shown in FIGS. 11A-C, a filtering media may be advantageously added to an encapsulant that functions both as a cover to protect LEDs and bonding wires and as an optical filter 1100. In one embodiment, a filtering media 1100 encapsulates a select group of LEDs and a clear media 600 (FIG. 6) encapsulates the entire array 700 and the filtering media 1000 (FIG. 6). In a particular embodiment, corresponding to TABLE 1, above, five LEDs nominally emitting at 660-905 nm are encapsulated with both a filtering media 1100 and an overlying clear media 600 (FIG. 6), i.e. attenuated. In a particular embodiment, the filtering media 1100 is a 40:1 mixture of a clear encapsulant (EPO-TEK 0G147-7) and an opaque encapsulate (EPO-TEK 0G147) both available from Epoxy Technology, Inc., Billerica, Mass. Three LEDs nominally emitting at 610-630 nm are only encapsulated with the clear media 600 (FIG. 6), i.e. unattenuated. In alternative embodiments, individual LEDs may be singly or multiply encapsulated according to tissue absorption and/or output intensity. In other alternative embodiments, filtering media may be separately attachable optical filters or a combination of encapsulants and separately attachable optical filters. In a particular embodiment, the emitter assembly 500 has one or more notches along each side proximate the component end 1305 (FIG. 13) for retaining one or more clip-on optical filters.

Substrate

Figure 12:
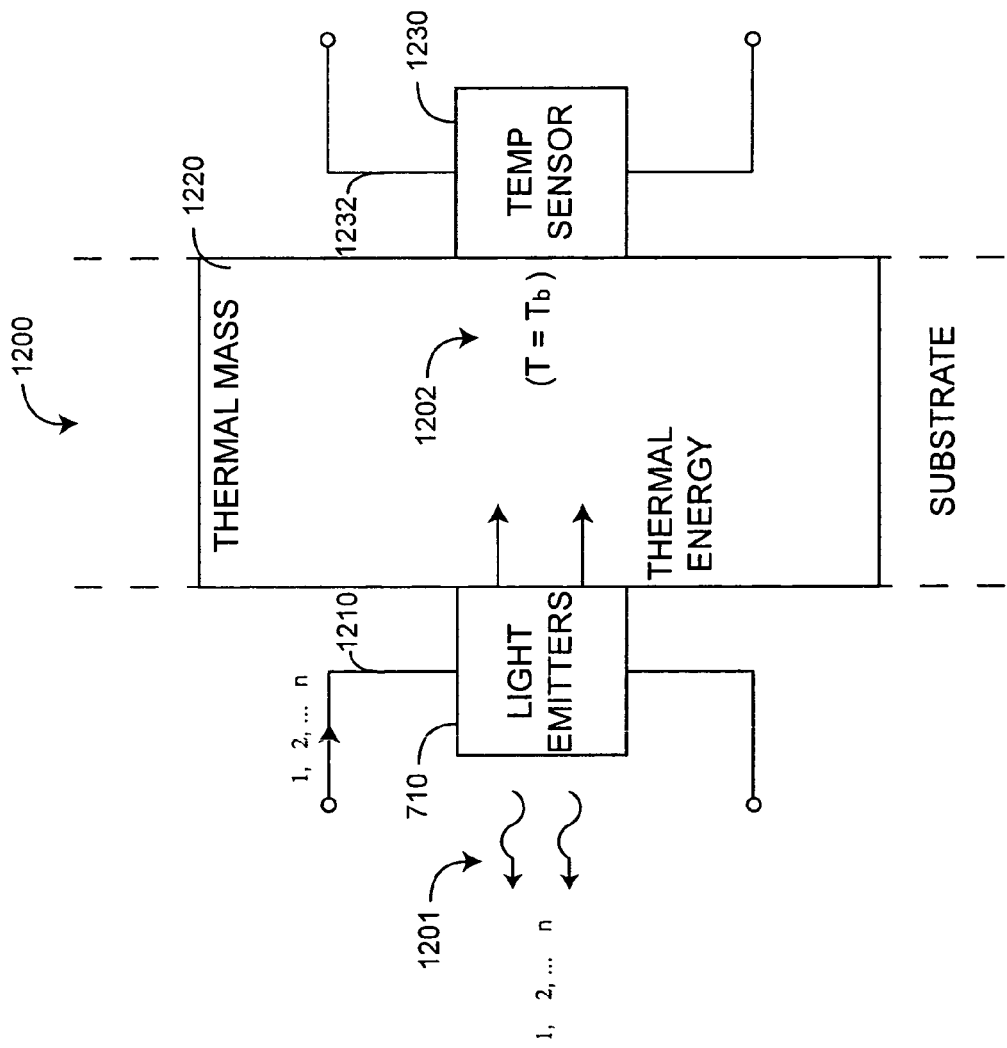
FIG. 12 is a general block diagram of an emitter substrate.

FIG. 12 illustrates light emitters 710 configured to transmit optical radiation 1201 having multiple wavelengths in response to corresponding drive currents 1210. A thermal mass 1220 is disposed proximate the emitters 710 so as to stabilize a bulk temperature 1202 for the emitters. A temperature sensor 1230 is thermally coupled to the thermal mass 1220, wherein the temperature sensor 1230 provides a temperature sensor output 1232 responsive to the bulk temperature 1202 so that the wavelengths are determinable as a function of the drive currents 1210 and the bulk temperature 1202.

In one embodiment, an operating wavelength $\lambda_a$ of each light emitter 710 is determined according to EQ. 3

$$\lambda_a = f(T_b, I_{drive}, \Sigma I_{drive}) \quad (3)$$

where $T_b$ is the bulk temperature, $I_{drive}$ is the drive current for a particular light emitter, as determined by the sensor controller 4500 (FIG. 45), described below, and $\Sigma I_{drive}$ is the total drive current for all light emitters. In another embodiment, temperature sensors are configured to measure the temperature of each light emitter 710 and an operating wavelength $\lambda_a$ of each light emitter 710 is determined according to EQ. 4

$$\lambda_a = f(T_a, I_{drive}, \Sigma I_{drive}) \quad (4)$$

where $T_a$ is the temperature of a particular light emitter, $I_{drive}$ is the drive current for that light emitter and $\Sigma I_{drive}$ is the total drive current for all light emitters.

In yet another embodiment, an operating wavelength for each light emitter is determined by measuring the junction voltage for each light emitter 710. In a further embodiment, the temperature of each light emitter 710 is controlled, such as by one or more Peltier cells coupled to each light emitter 710, and an operating wavelength for each light emitter 710 is determined as a function of the resulting controlled temperature or temperatures. In other embodiments, the operating wavelength for each light emitter 710 is determined directly, for example by attaching a charge coupled device (CCD) to each light emitter or by attaching a fiberoptic to each light emitter and coupling the fiberoptics to a wavelength measuring device, to name a few.

Figure 13:
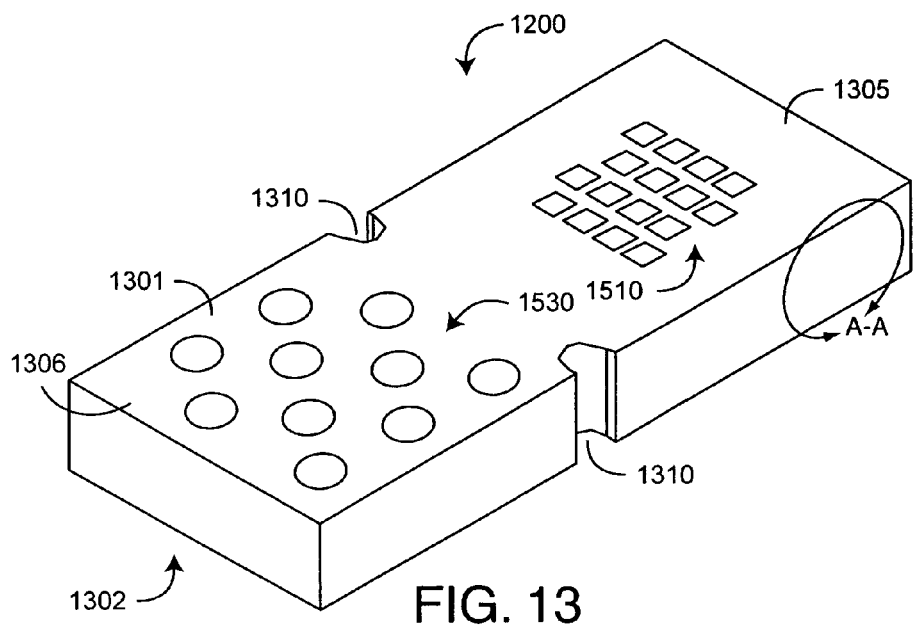
FIGS. 13-14 are top and detailed side views of an emitter substrate embodiment.
Figure 14:
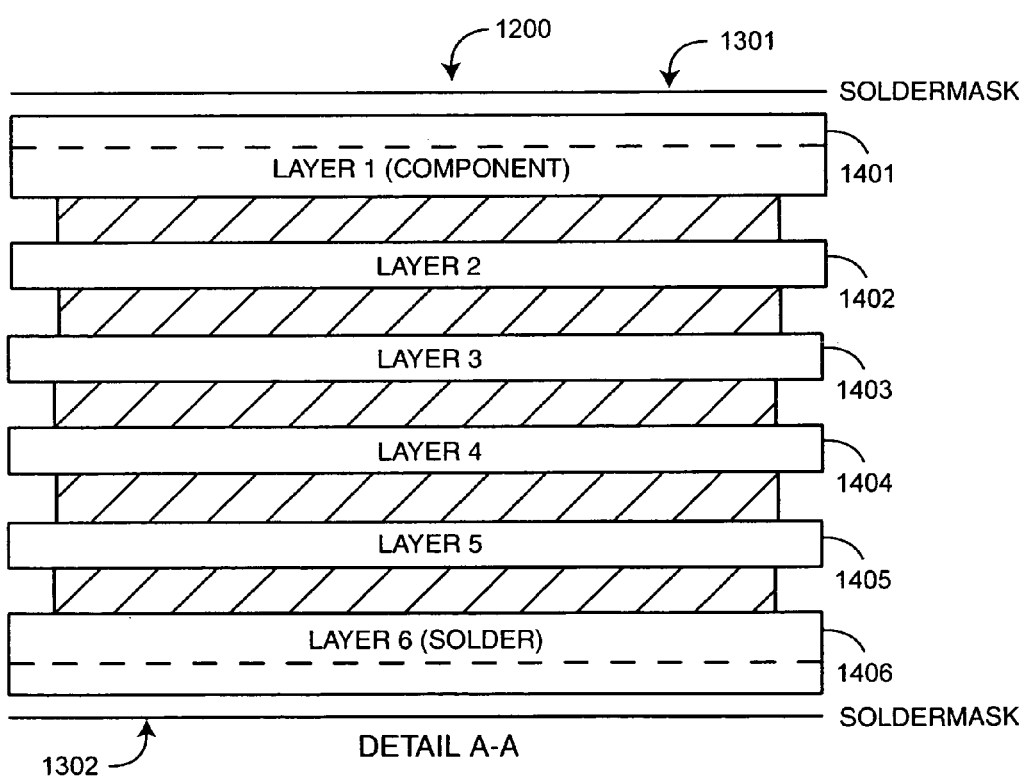
Figures 15, 16:
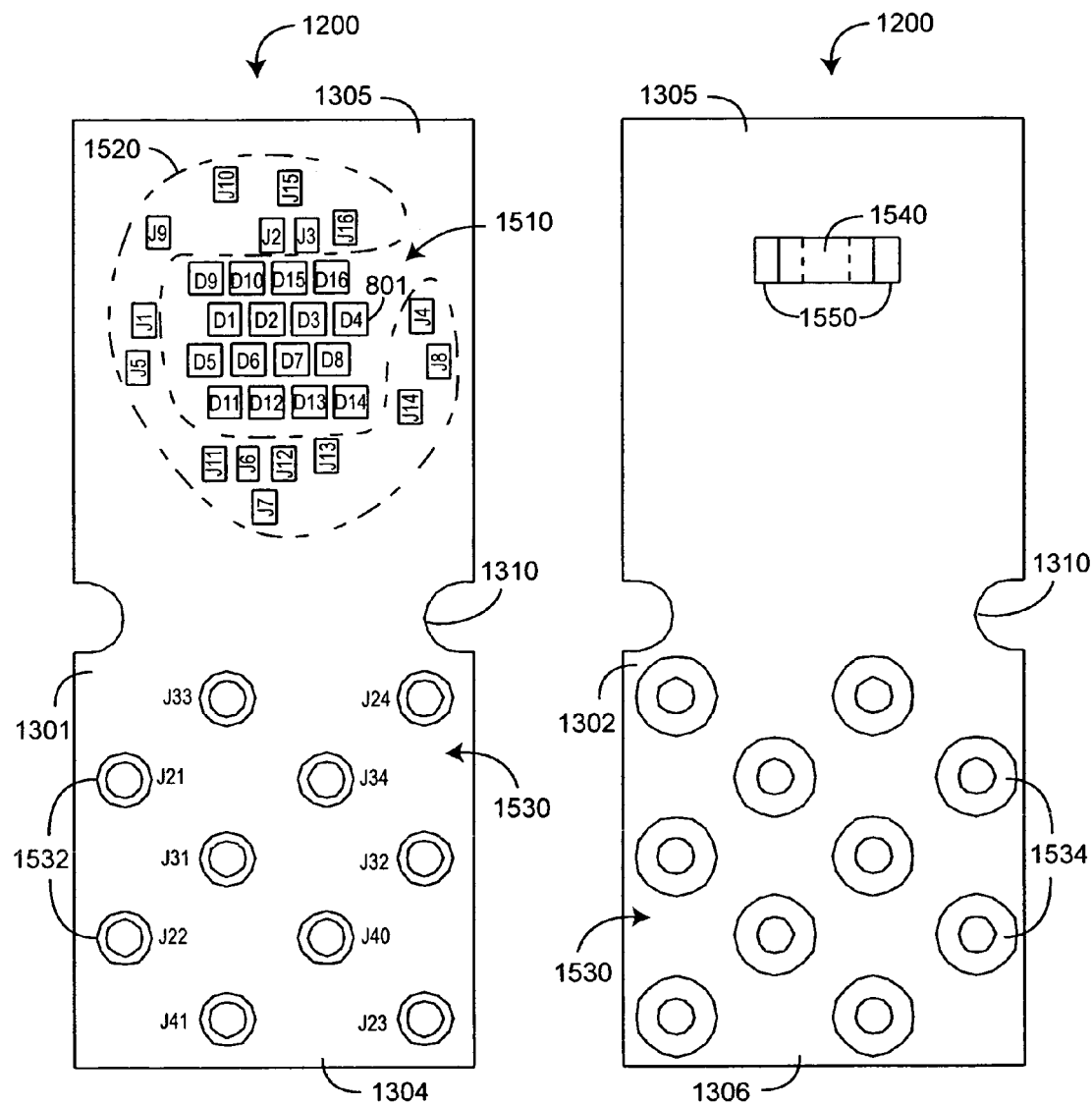
FIGS. 15-16 are top and bottom component layout views of an emitter substrate embodiment.

FIGS. 13-18 illustrate one embodiment of a substrate 1200 configured to provide thermal conductivity between an emitter array 700 (FIG. 8) and a thermistor 1540 (FIG. 16). In this manner, the resistance of the thermistor 1540 (FIG. 16) can be measured in order to determine the bulk temperature of LEDs 801 (FIG. 8) mounted on the substrate 1200. The substrate 1200 is also configured with a relatively significant thermal mass, which stabilizes and normalizes the bulk temperature so that the thermistor measurement of bulk temperature is meaningful.

FIGS. 13-14 illustrate a substrate 1200 having a component side 1301, a solder side 1302, a component end 1305 and a connector end 1306. Alignment notches 1310 are disposed between the ends 1305, 1306. The substrate 1200 further has a component layer 1401, inner layers 1402-1405 and a solder layer 1406. The inner layers 1402-1405, e.g. inner layer 1402 (FIG. 18), have substantial metallized areas 1411 that provide a thermal mass 1220 (FIG. 12) to stabilize a bulk temperature for the emitter array 700 (FIG. 12). The metallized areas 1411 also function to interconnect component pads 1510 and wire bond pads 1520 (FIG. 15) to the connector 1530.

Figure 22:
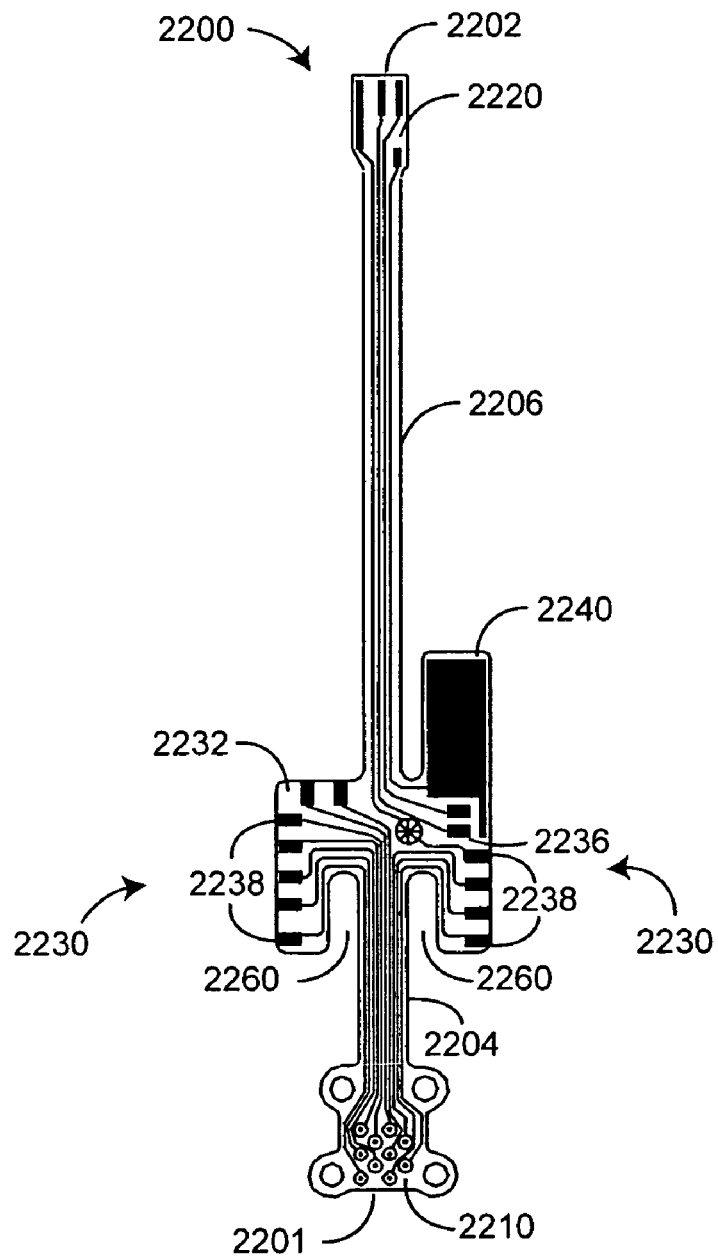
FIG. 22 is a top plan view of a flex circuit.

FIGS. 15-16 illustrate a substrate 1200 having component pads 1510 and wire bond pads 1520 at a component end 1305. The component pads 1510 mount and electrically connect a first side (anode or cathode) of the LEDs 801 (FIG. 8) to the substrate 1200. Wire bond pads 1520 electrically connect a second side (cathode or anode) of the LEDs 801 (FIG. 8) to the substrate 1200. The connector end 1306 has a connector 1530 with connector pads 1532, 1534 that mount and electrically connect the emitter assembly 500 (FIG. 23), including the substrate 1200, to the flex circuit 2200 (FIG. 22). Substrate layers 1401-1406 (FIG. 14) have traces that electrically connect the component pads 1510 and wire bond pads 1520 to the connector 1532-1534. A thermistor 1540 is mounted to thermistor pads 1550 at the component end 1305, which are also electrically connected with traces to the connector 1530. Plated thru holes electrically connect the connector pads 1532, 1534 on the component and solder sides 1301, 1302, respectively.

Figure 17:
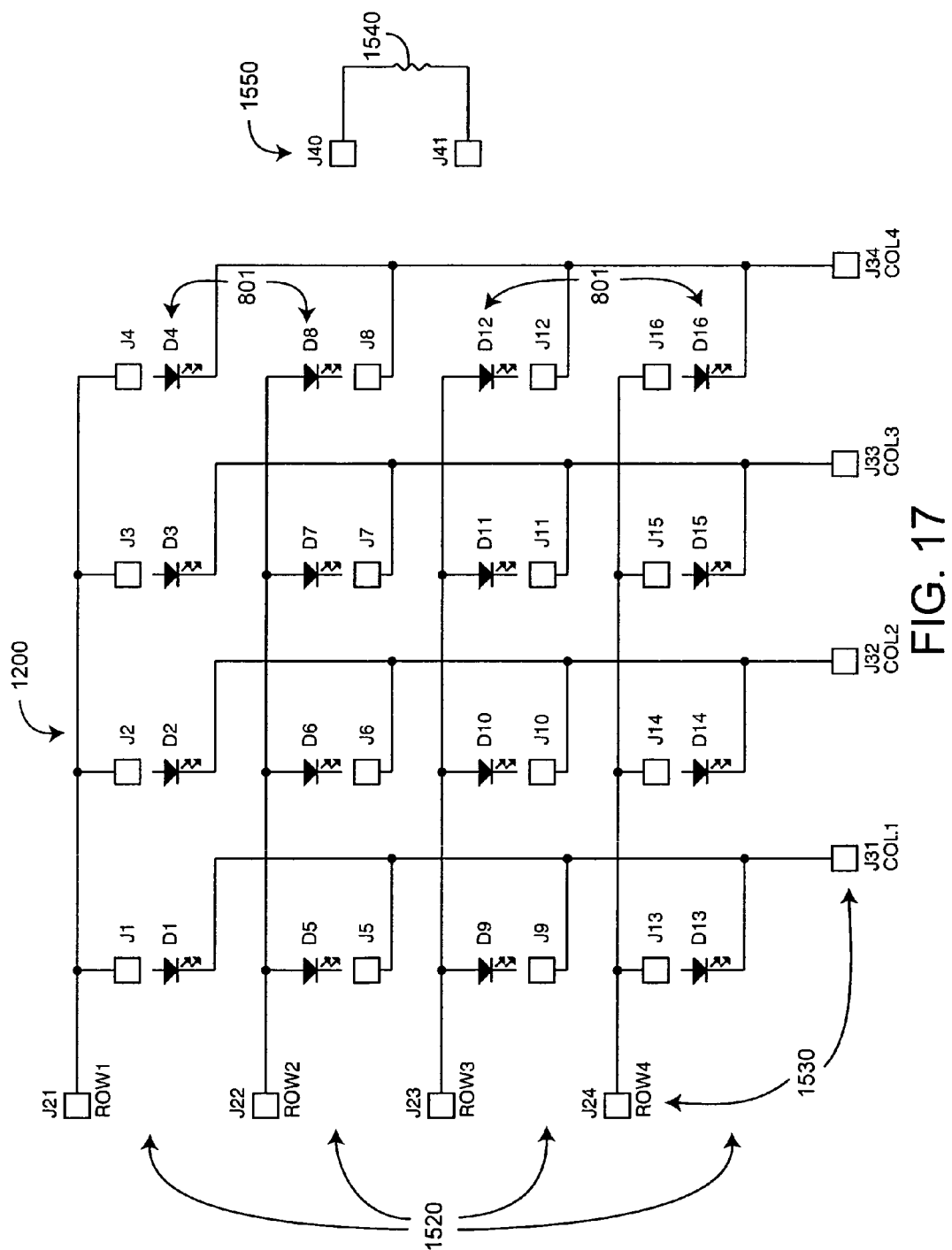
FIG. 17 is a schematic diagram of an emitter substrate embodiment.
Figure 18:
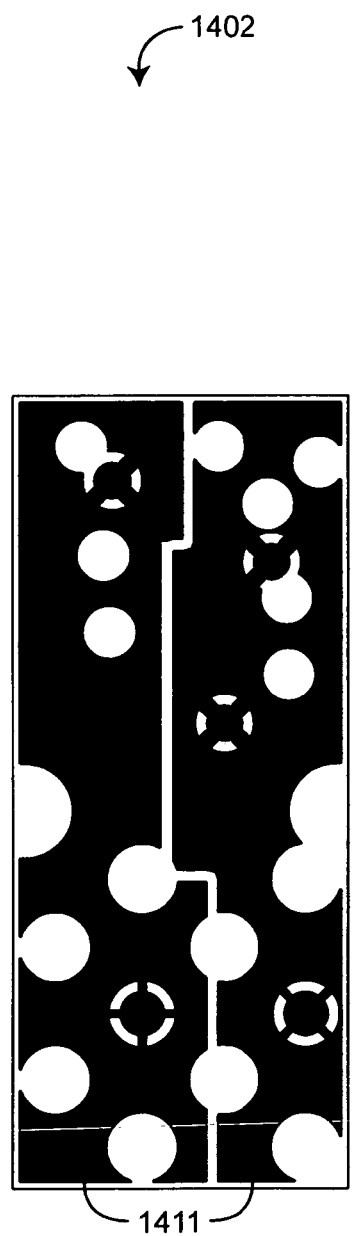
FIG. 18 is a plan view of an inner layer of an emitter substrate embodiment.

FIG. 17 illustrates the electrical layout of a substrate 1200. A portion of the LEDs 801, including D1-D4 and D13-D16 have cathodes physically and electrically connected to component pads 1510 (FIG. 15) and corresponding anodes wire bonded to wire bond pads 1520. Another portion of the LEDs 801, including D5-D8 and D9-D12, have anodes physically and electrically connected to component pads 1510 (FIG. 15) and corresponding cathodes wire bonded to wire bond pads 1520. The connector 1530 has row pinouts J21-J24, column pinouts J31-J34 and thermistor pinouts J40-J41 for the LEDs 801 and thermistor 1540.

Interconnect Assembly

Figure 19:
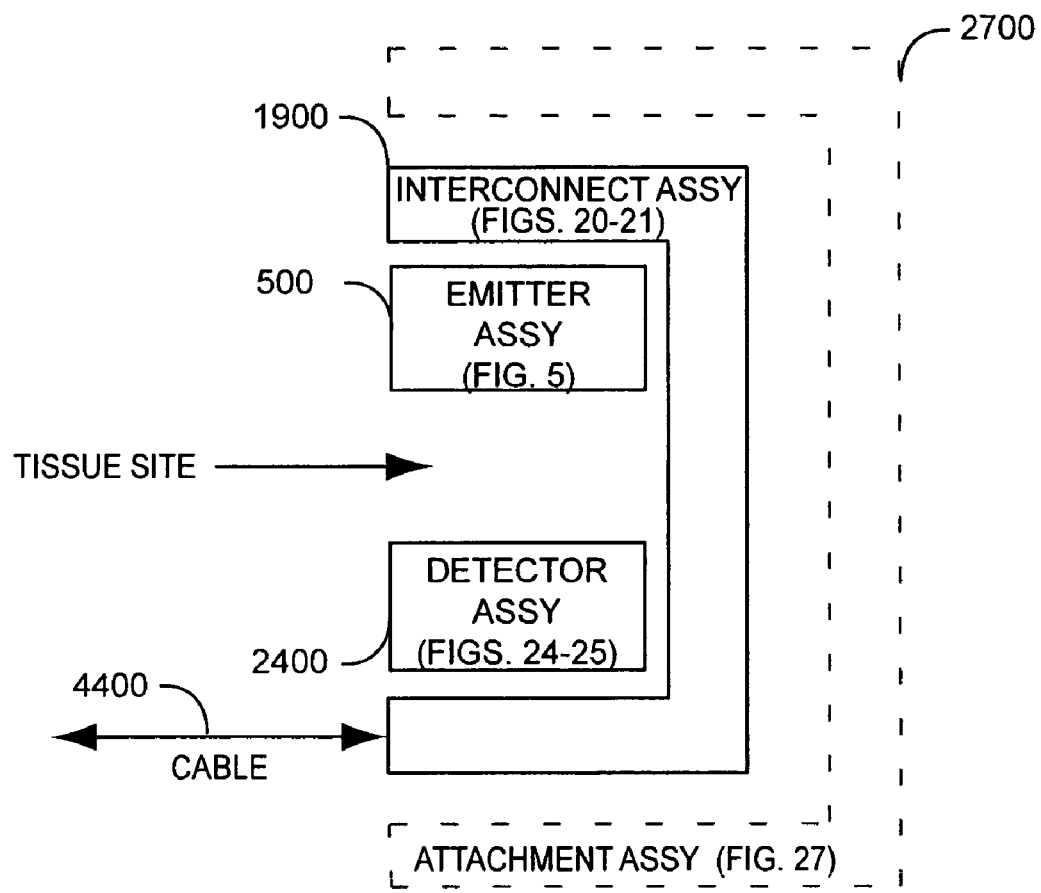
FIG. 19 is a general block diagram of an interconnect assembly in relationship to other sensor assemblies.

FIG. 19 illustrates an interconnect assembly 1900 that mounts the emitter assembly 500 and detector assembly 2400, connects to the sensor cable 4400 and provides electrical communications between the cable and each of the emitter assembly 500 and detector assembly 2400. In one embodiment, the interconnect assembly 1900 is incorporated with the attachment assembly 2700, which holds the emitter and detector assemblies to a tissue site. An interconnect assembly embodiment utilizing a flexible (flex) circuit is described with respect to FIGS. 20-24, below.

Figure 20:
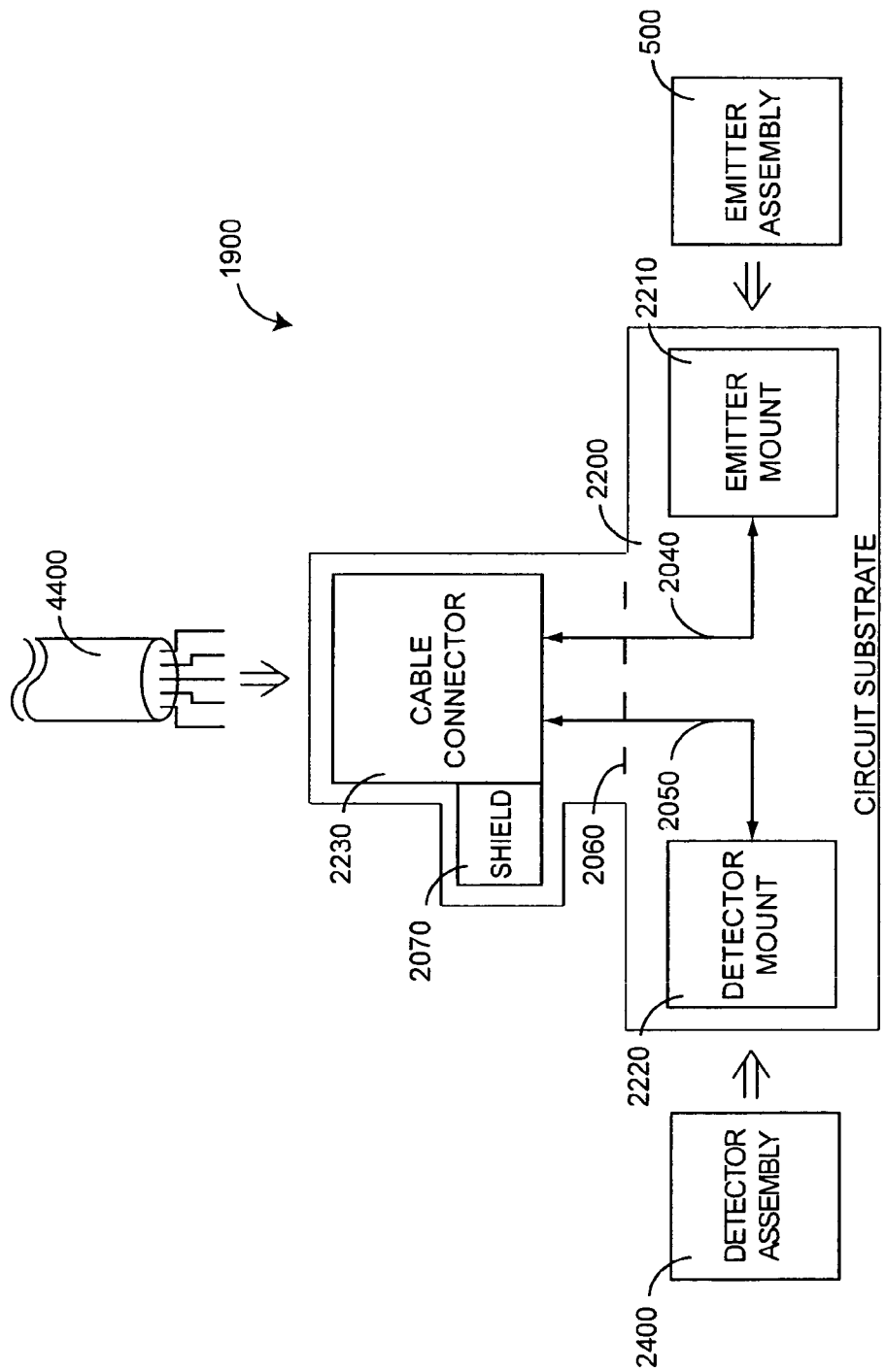
FIG. 20 is a block diagram of an interconnect assembly embodiment.

FIG. 20 illustrates an interconnect assembly 1900 embodiment having a circuit substrate 2200, an emitter mount 2210, a detector mount 2220 and a cable connector 2230. The emitter mount 2210, detector mount 2220 and cable connector 2230 are disposed on the circuit substrate 2200. The emitter mount 2210 is adapted to mount an emitter assembly 500 having multiple emitters. The detector mount 2220 is adapted to mount a detector assembly 2400 having a detector. The cable connector 2230 is adapted to attach a sensor cable 4400. A first plurality of conductors 2040 disposed on the circuit substrate 2200 electrically interconnects the emitter mount 2210 and the cable connector 2230. A second plurality of conductors 2050 disposed on the circuit substrate 2200 electrically interconnects the detector mount 2220 and the cable connector 2230. A decoupling 2060 disposed proximate the cable connector 2230 substantially mechanically isolates the cable connector 2230 from both the emitter mount 2210 and the detector mount 2220 so that sensor cable stiffness is not translated to the emitter assembly 500 or the detector assembly 2400. A shield 2070 is adapted to fold over and shield one or more wires or pairs of wires of the sensor cable 4400.

Figure 21:
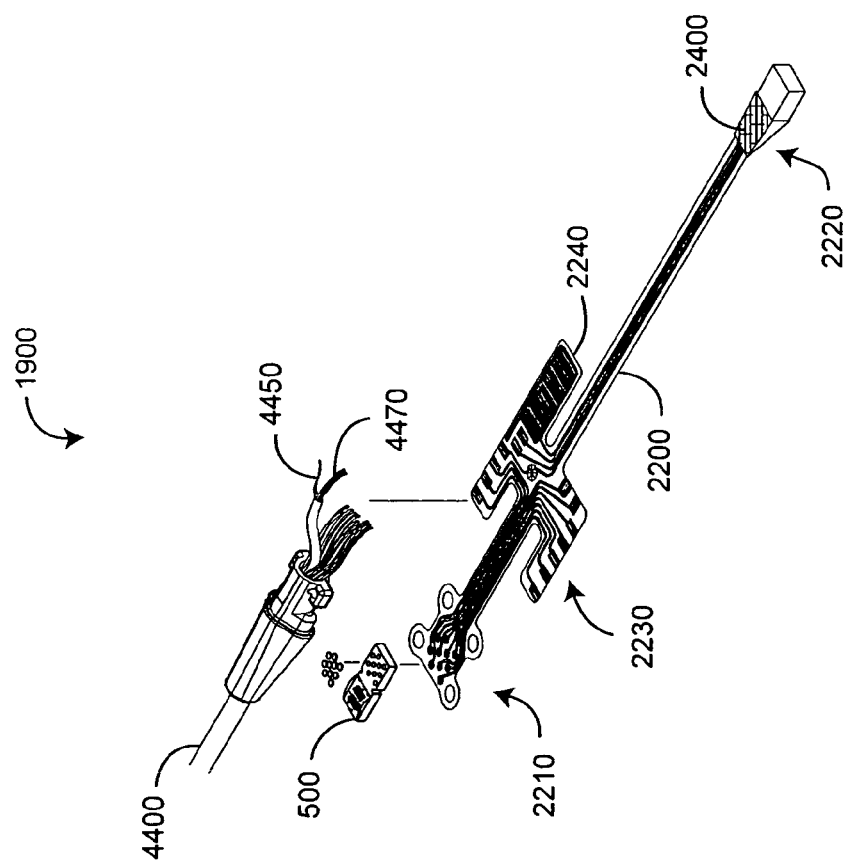
FIG. 21 is a partially-exploded perspective view of a flex circuit assembly embodiment of an interconnect assembly.

FIG. 21 illustrates a flex circuit assembly 1900 having a flex circuit 2200, an emitter assembly 500 and a detector assembly 2400, which is configured to terminate the sensor end of a sensor cable 4400. The flex circuit assembly 1900 advantageously provides a structure that electrically connects yet mechanically isolates the sensor cable 4400, the emitter assembly 500 and the detector assembly 2400. As a result, the mechanical stiffness of the sensor cable 4400 is not translated to the sensor pads 3000, 3100 (FIGS. 30-31), allowing a comfortable finger attachment for the sensor 200 (FIG. 1). In particular, the emitter assembly 500 and detector assembly 2400 are mounted to opposite ends 2201, 2202 (FIG. 22) of an elongated flex circuit 2200. The sensor cable 4400 is mounted to a cable connector 2230 extending from a middle portion of the flex circuit 2200. Detector wires 4470 are shielded at the flex circuit junction by a fold-over conductive ink flap 2240, which is connected to a cable inner shield 4450. The flex circuit 2200 is described in further detail with respect to FIG. 22. The emitter portion of the flex circuit assembly 1900 is described in further detail with respect to FIG. 23. The detector assembly 2400 is described with respect to FIG. 24. The sensor cable 4400 is described with respect to FIGS. 44A-B, below.

Figure 24:
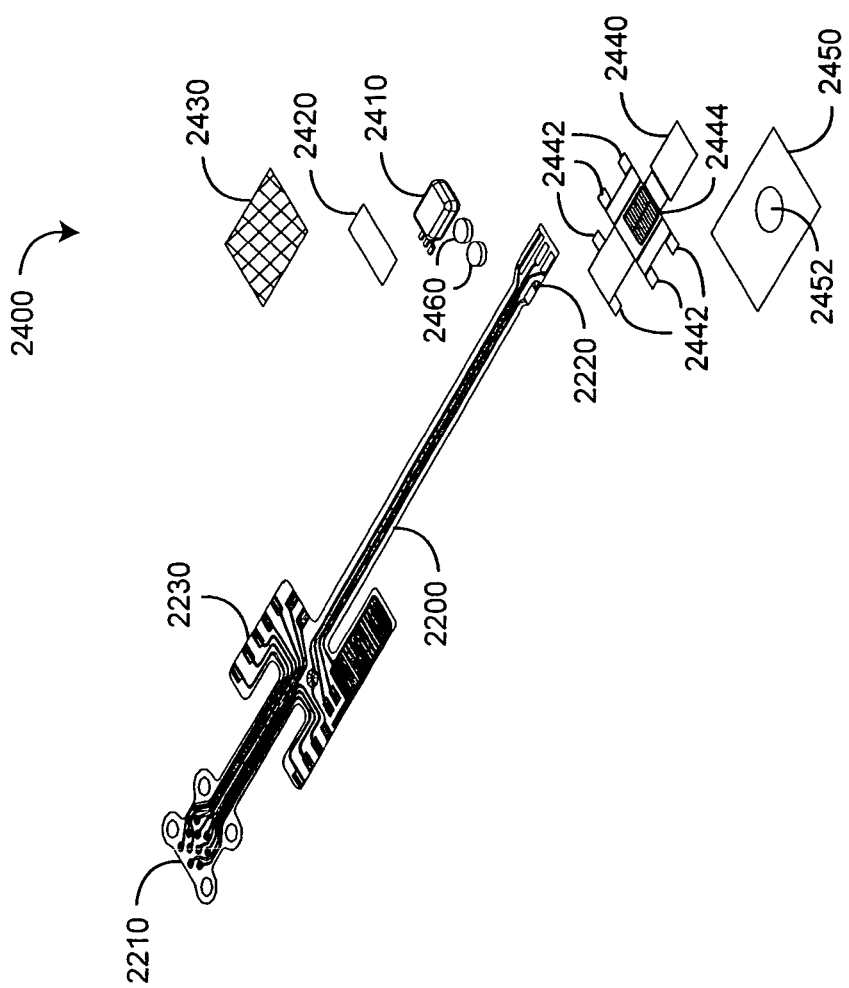
FIG. 24 is an exploded perspective view of a detector assembly embodiment.
Figures 44A, 44B:
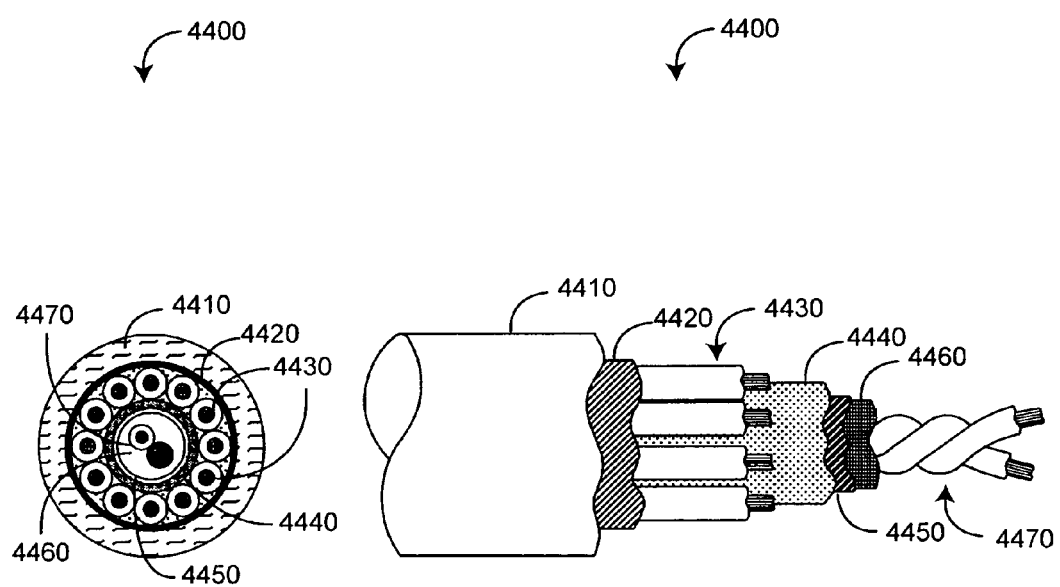
FIGS. 44A-B are cross sectional and side cut away views of a sensor cable.

FIG. 22 illustrates a sensor flex circuit 2200 having an emitter end 2201, a detector end 2202, an elongated interconnect 2204, 2206 between the ends 2201, 2202 and a cable connector 2230 extending from the interconnect 2204, 2206. The emitter end 2201 forms a "head" having emitter solder pads 2210 for attaching the emitter assembly 500 (FIG. 6) and mounting ears 2214 for attaching to the emitter pad 3000 (FIG. 30B), as described below. The detector end 2202 has detector solder pads for attaching the detector 2410 (FIG. 24). The interconnect 2204 between the emitter end 2201 and the cable connector 2230 forms a "neck," and the interconnect 2206 between the detector end 2202 and the cable connector 2230 forms a "tail." The cable connector 2230 forms "wings" that extend from the interconnect 2204, 2206 between the neck 2204 and tail 2206. A conductive ink flap 2240 connects to the cable inner shield 4450 (FIGS. 44A-B) and folds over to shield the detector wires 4470 (FIGS. 44A-B) soldered to the detector wire pads 2236. The outer wire pads 2238 connect to the remaining cable wires 4430 (FIGS. 44A-B). The flex circuit 2200 has top coverlay, top ink, inner coverlay, trace, trace base, bottom ink and bottom coverlay layers.

The flex circuit 2200 advantageously provides a connection between a multiple wire sensor cable 4400 (FIGS. 44A-B), a multiple wavelength emitter assembly 500 (FIG. 6) and a detector assembly 2400 (FIG. 24) without rendering the emitter and detector assemblies unwieldy and stiff. In particular, the wings 2230 provide a relatively large solder pad area 2232 that is narrowed at the neck 2204 and tail 2206 to mechanically isolate the cable 4400 (FIGS. 44A-B) from the remainder of the flex circuit 2200. Further, the neck 2206 is folded (see FIG. 4) for installation in the emitter pad 3000 (FIGS. 30A-H) and acts as a flexible spring to further mechanically isolate the cable 4400 (FIGS. 44A-B) from the emitter assembly 500 (FIG. 4). The tail 2206 provides an integrated connectivity path between the detector assembly 2400 (FIG. 24) mounted in the detector pad 3100 (FIGS. 31A-H) and the cable connector 2230 mounted in the opposite emitter pad 3000 (FIGS. 30A-H).

Figure 23:
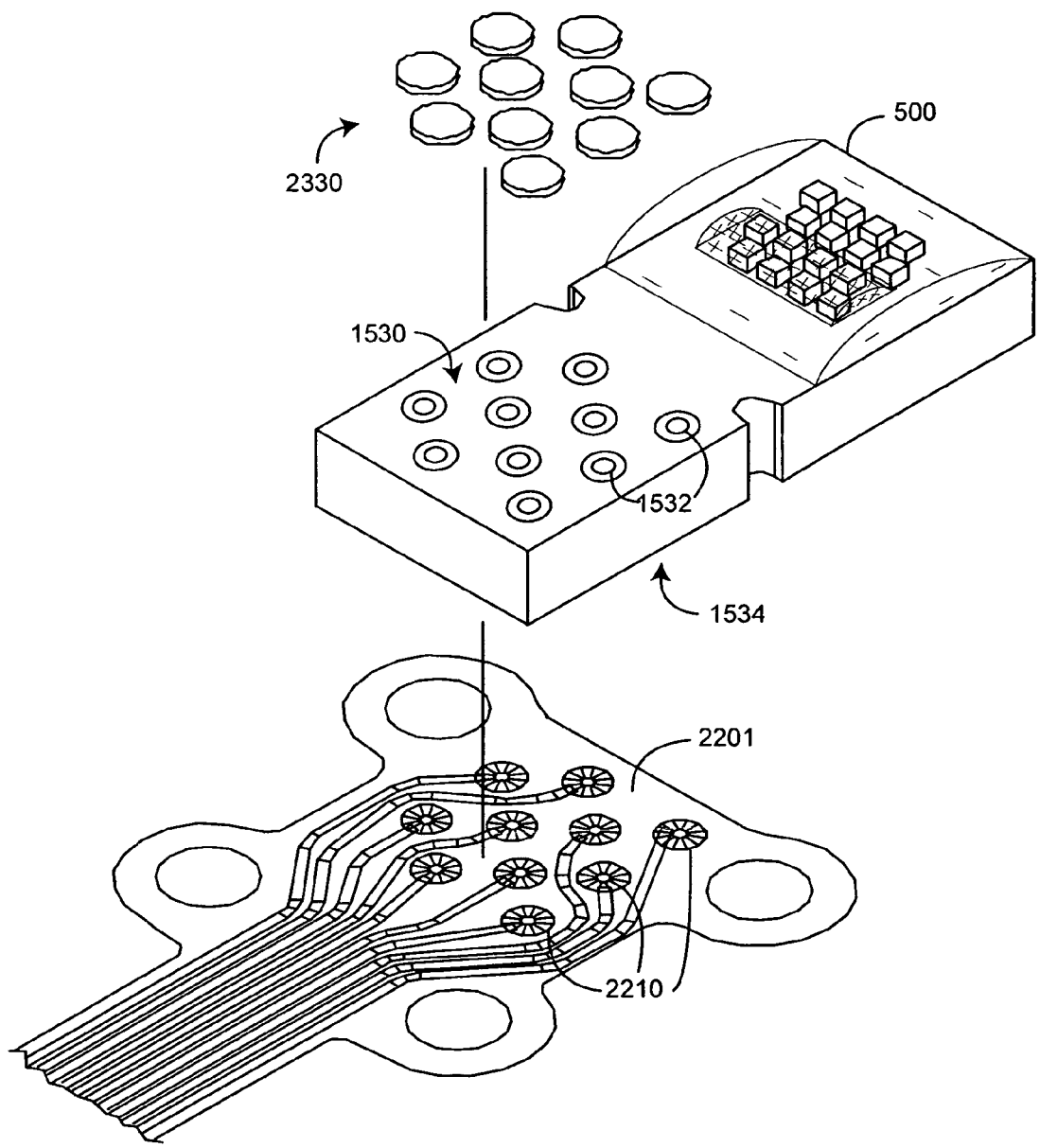
FIG. 23 is an exploded perspective view of an emitter portion of a flex circuit assembly.

FIG. 23 illustrates the emitter portion of the flex circuit assembly 1900 (FIG. 21) having the emitter assembly 500. The emitter assembly connector 1530 is attached to the emitter end 2210 of the flex circuit 2200 (FIG. 22). In particular, reflow solder 2330 connects thru hole pads 1532, 1534 of the emitter assembly 500 to corresponding emitter pads 2310 of the flex circuit 2200 (FIG. 22).

FIG. 24 illustrates a detector assembly 2400 including a detector 2410, solder pads 2420, copper mesh tape 2430, an EMI shield 2440 and foil 2450. The detector 2410 is soldered 2460 chip side down to detector solder pads 2420 of the flex circuit 2200. The detector solder joint and detector ground pads 2420 are wrapped with the Kapton tape 2470. EMI shield tabs 2442 are folded onto the detector pads 2420 and soldered. The EMI shield walls are folded around the detector 2410 and the remaining tabs 2442 are soldered to the back of the EMI shield 2440. The copper mesh tape 2430 is cut to size and the shielded detector and flex circuit solder joint are wrapped with the copper mesh tape 2430. The foil 2450 is cut to size with a predetermined aperture 2452. The foil 2450 is wrapped around shielded detector with the foil side in and the aperture 2452 is aligned with the EMI shield grid 2444.

Detector Assembly

Figure 25:
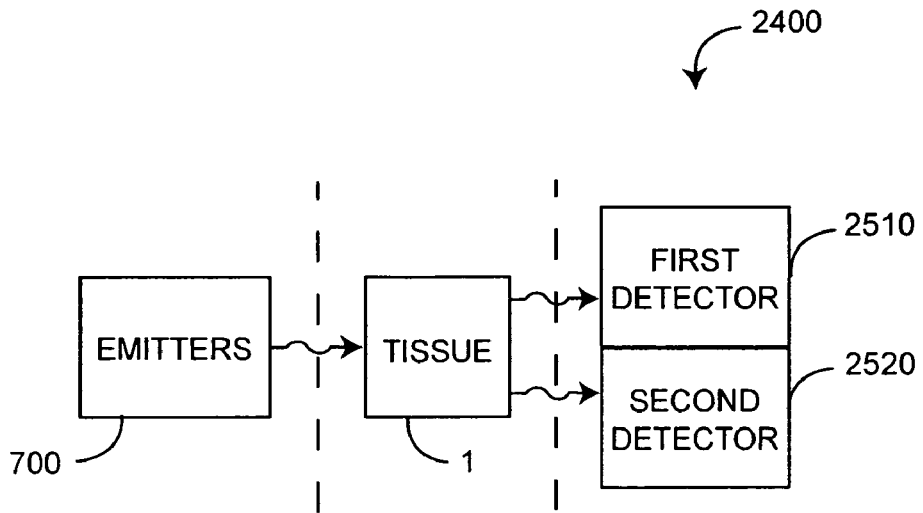
FIGS. 25-26 are block diagrams of adjacent detector and stacked detector embodiments.

FIG. 25 illustrates an alternative detector assembly 2400 embodiment having adjacent detectors. Optical radiation having multiple wavelengths generated by emitters 700 is transmitted into a tissue site 1. Optical radiation at a first set of wavelengths is detected by a first detector 2510, such as, for example, a Si detector. Optical radiation at a second set of wavelengths is detected by a second detector 2520, such as, for example, a GaAs detector.

Figure 26:
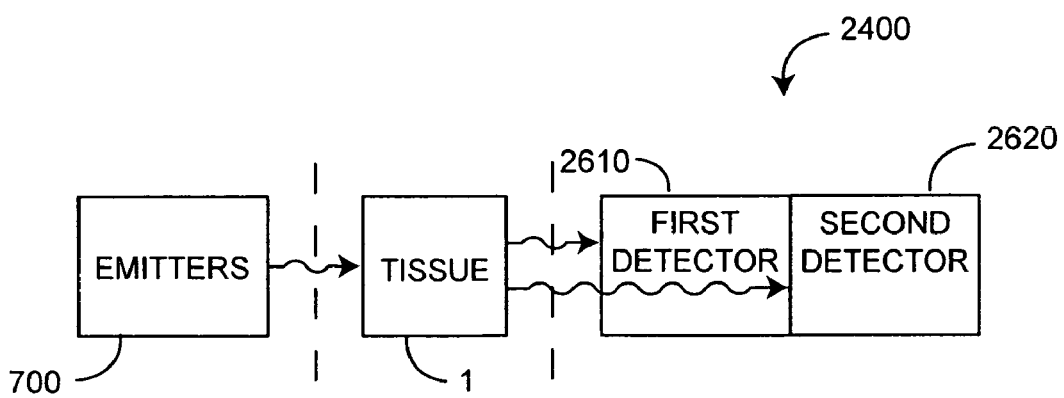

FIG. 26 illustrates another alternative detector assembly 2400 embodiment having stacked detectors coaxial along a light path. Optical radiation having multiple wavelengths generated by emitters 700 is transmitted into a tissue site 1. Optical radiation at a first set of wavelengths is detected by a first detector 2610. Optical radiation at a second set of wavelengths passes through the first detector 2610 and is detected by a second detector 2620. In a particular embodiment, a silicon (Si) detector and a gallium arsenide (GaAs) detector are used. The Si detector is placed on top of the GaAs detector so that light must pass through the Si detector before reaching the GaAs detector. The Si detector can be placed directly on top of the GaAs detector or the Si and GaAs detector can be separated by some other medium, such as a transparent medium or air. In another particular embodiment, a germanium detector is used instead of the GaAs detector. Advantageously, the stacked detector arrangement minimizes error caused by pathlength differences as compared with the adjacent detector embodiment.

Finger Clip

Figure 27:
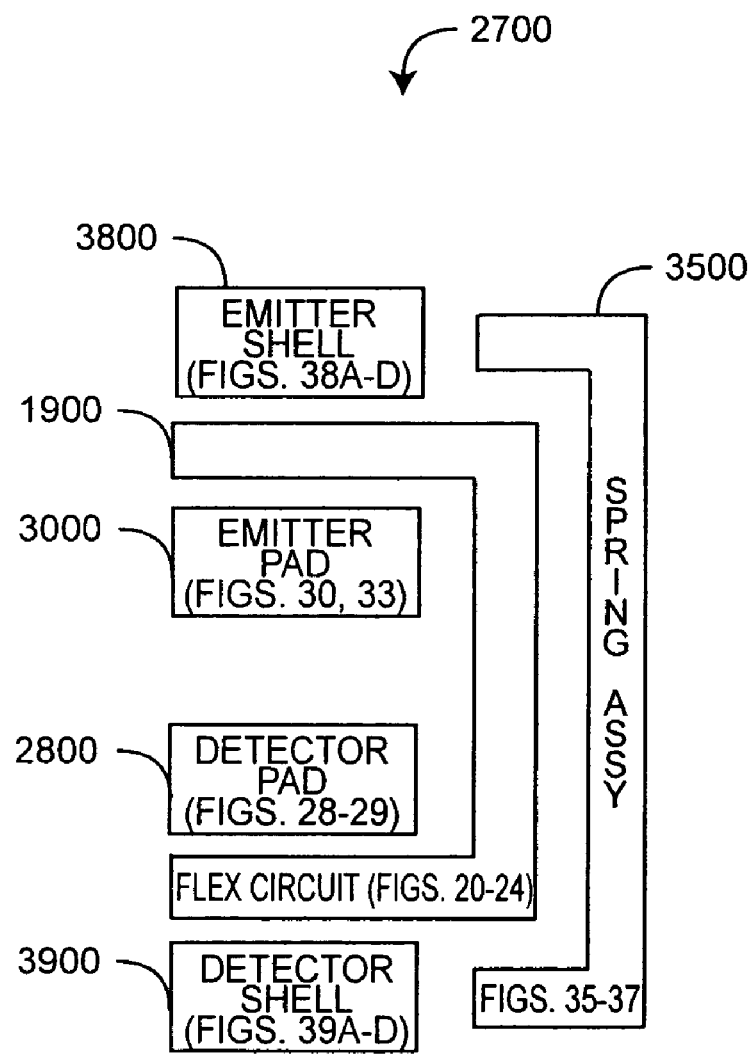
FIG. 27 is a block diagram of a finger clip embodiment of an attachment assembly.

FIG. 27 illustrates a finger clip embodiment 2700 of a physiological sensor attachment assembly. The finger clip 2700 is configured to removably attach an emitter assembly 500 (FIG. 6) and detector assembly 2400 (FIG. 24), interconnected by a flex circuit assembly 1900, to a fingertip. The finger clip 2700 has an emitter shell 3800, an emitter pad 3000, a detector pad 2800 and a detector shell 3900. The emitter shell 3800 and the detector shell 3900 are rotatably connected and urged together by the spring assembly 3500. The emitter pad 3000 is fixedly retained by the emitter shell. The emitter assembly 500 (FIG. 6) is mounted proximate the emitter pad 3000 and adapted to transmit optical radiation having a plurality of wavelengths into fingertip tissue. The detector pad 2800 is fixedly retained by the detector shell 3900. The detector assembly 3500 is mounted proximate the detector pad 2800 and adapted to receive the optical radiation after attenuation by fingertip tissue.

Figure 28:
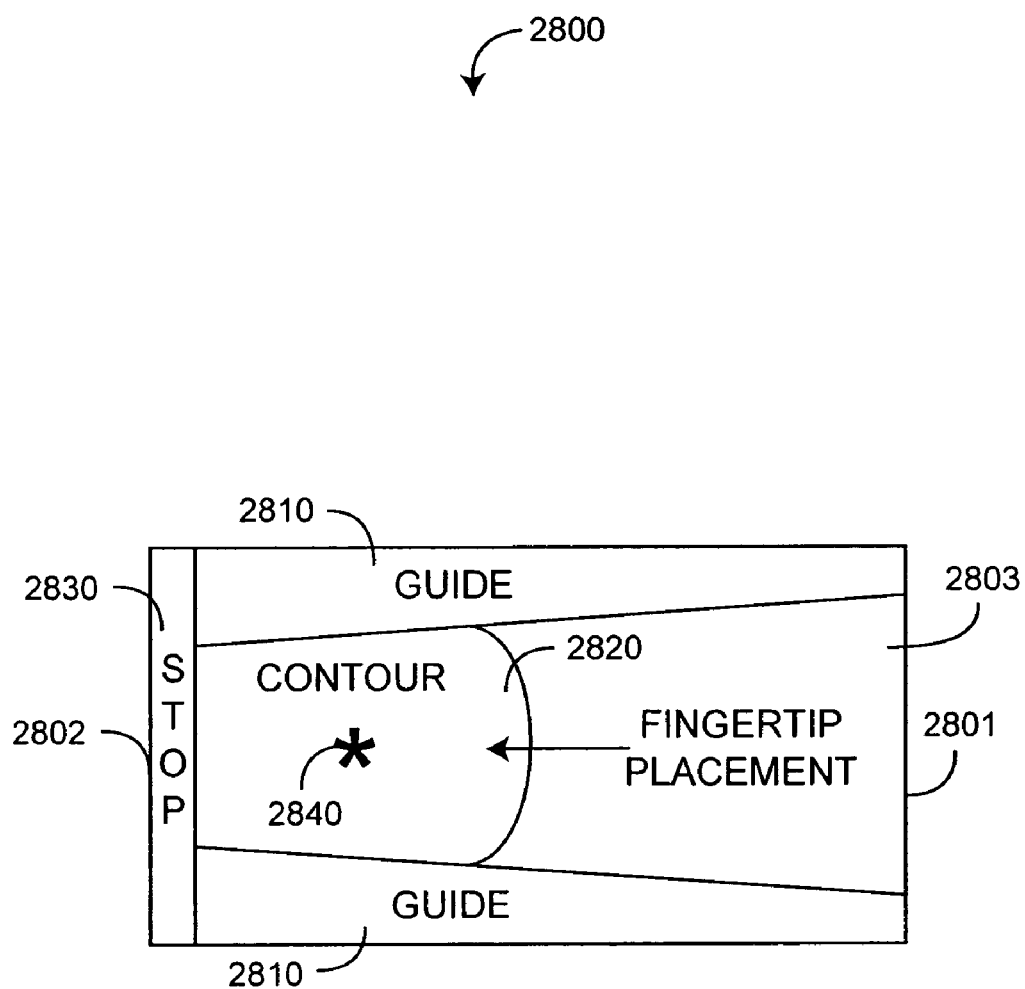
FIG. 28 is a general block diagram of a detector pad.
Figure 29A:
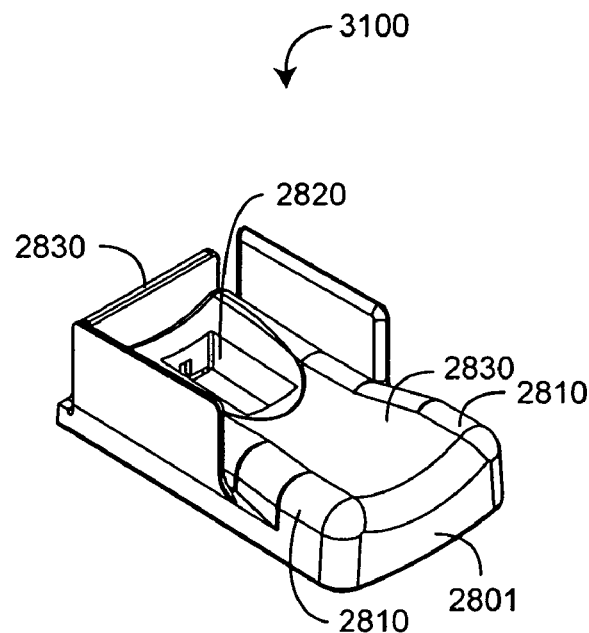
FIGS. 29A-B are perspective views of detector pad embodiments.
Figure 29B:
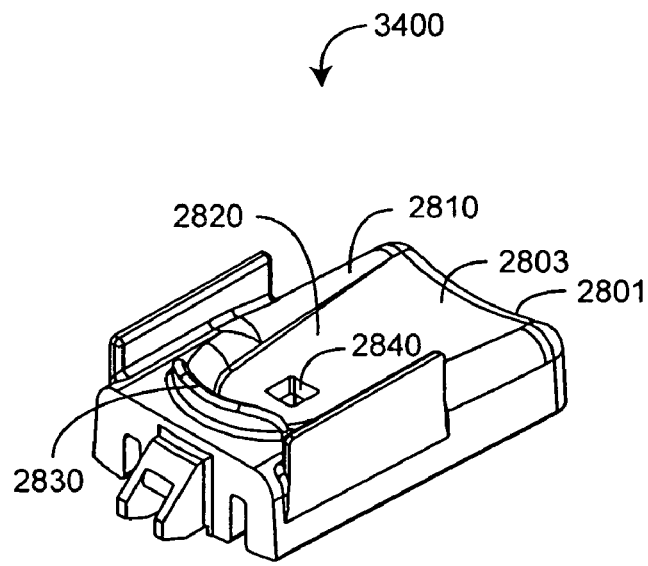
Figure 30A:
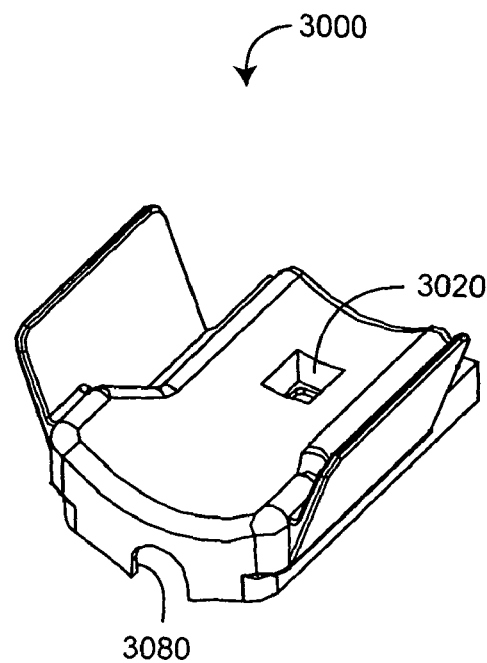
FIGS. 30A-H are perspective bottom, perspective top, bottom, back, top, side cross sectional, side, and front cross sectional views of an emitter pad embodiment.
Figure 30B:
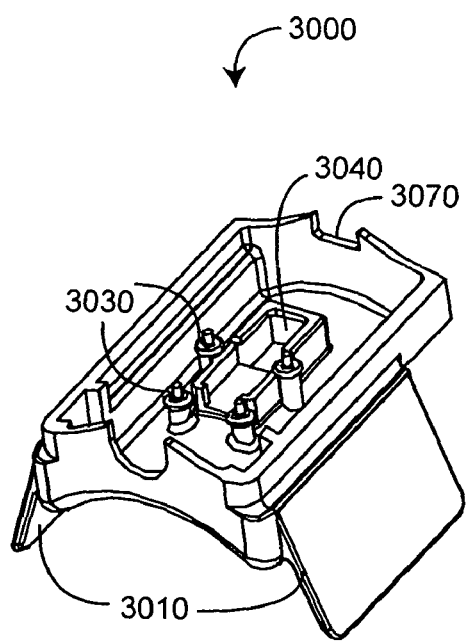
Figure 30C:
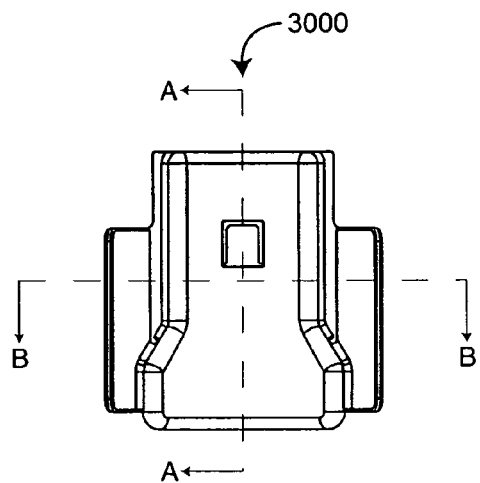
Figure 30F:
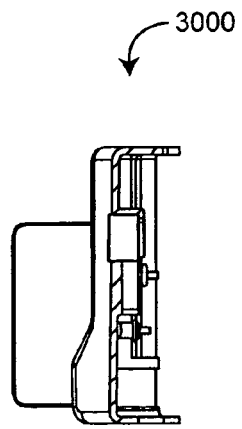
Figure 30D:
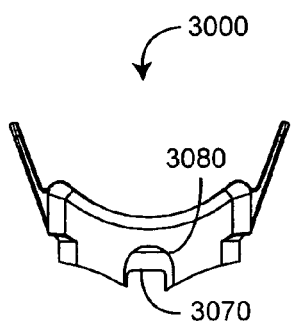
Figure 30G:
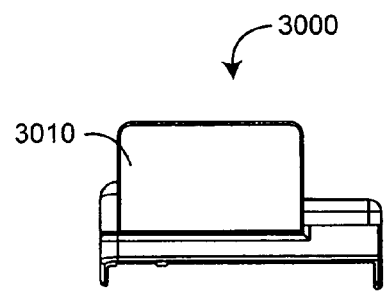
Figure 30E:
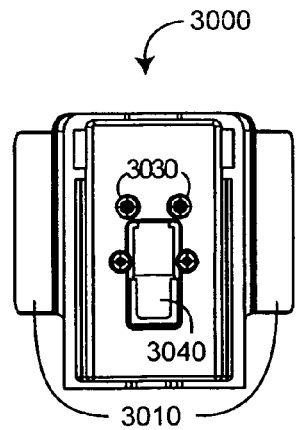
Figure 30H:
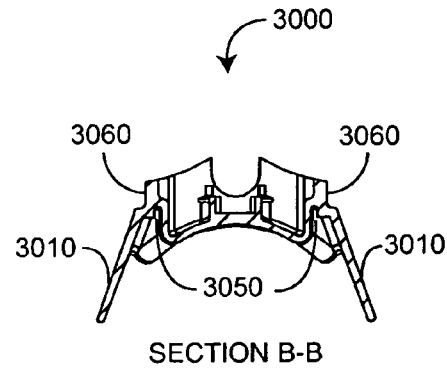
Figure 31A:
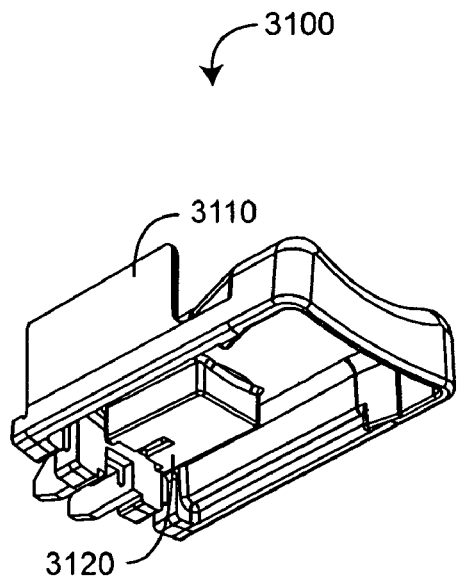
FIGS. 31A-H are perspective bottom, perspective top, top, back, bottom, side cross sectional, side, and front cross sectional views of a detector pad embodiment.
Figure 31B:
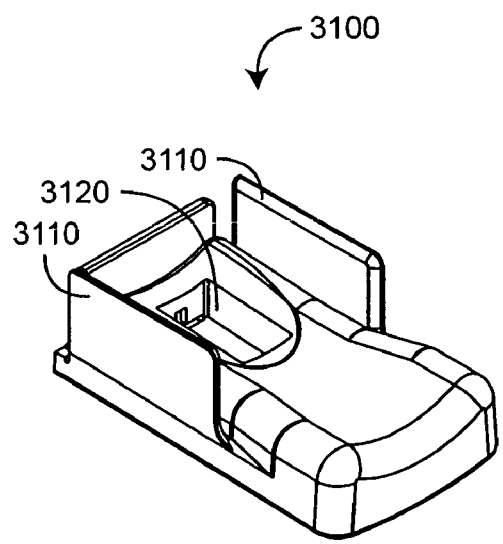
Figure 31C:
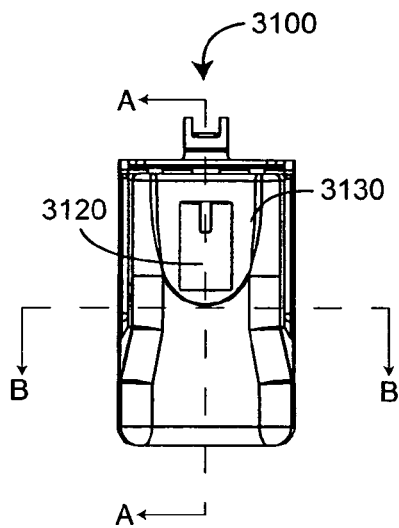
Figure 31D:
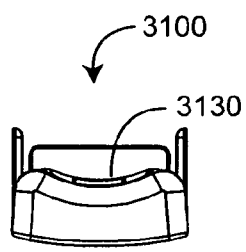
Figure 31E:
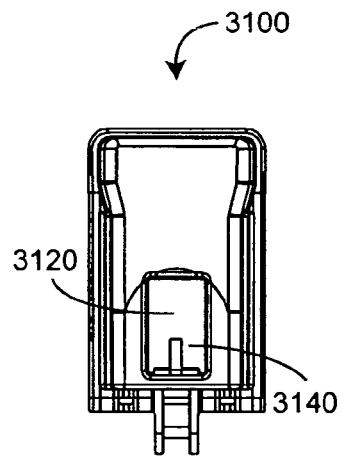
Figure 31F:
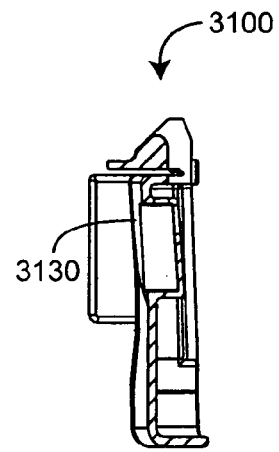
Figure 31G:
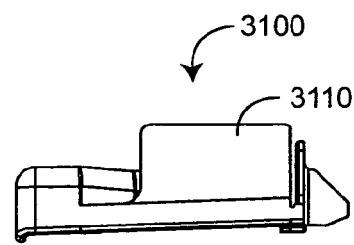
Figure 31H:
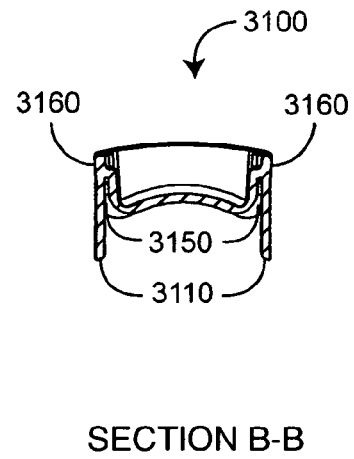
Figure 32A:
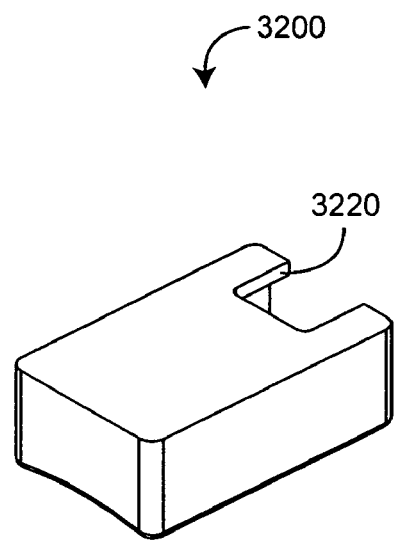
FIGS. 32A-H are perspective bottom, perspective top, top, back, bottom, side cross sectional, side, and front cross sectional views of a shoe box.
Figure 32B:
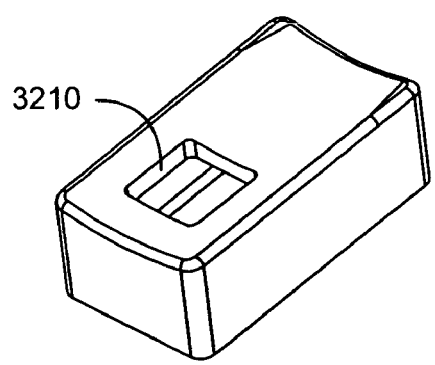
Figure 32C:
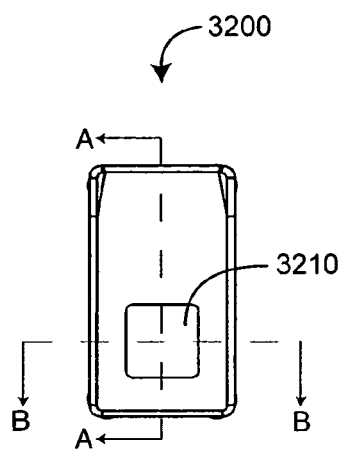
Figure 32F:
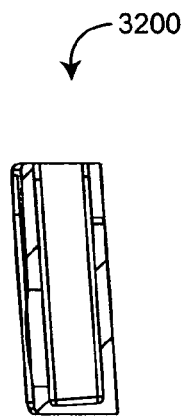
Figure 32D:
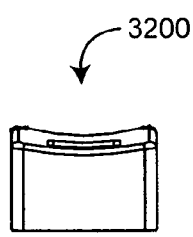
Figure 32G:
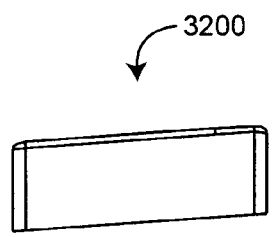
Figure 32E:
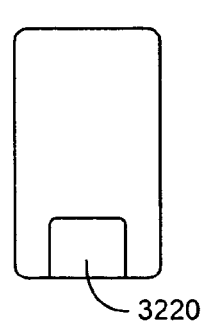
Figure 32H:
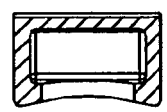
Figure 33A:
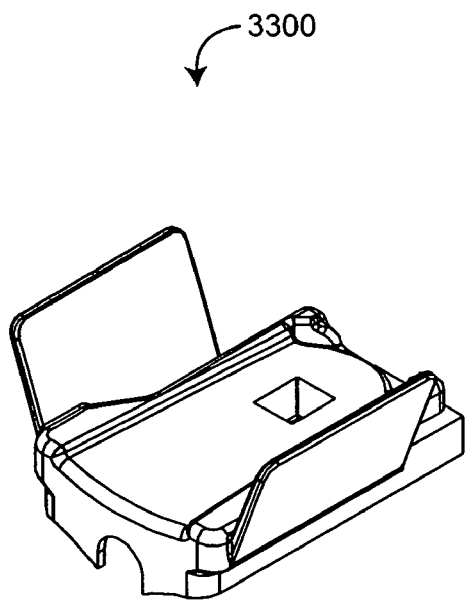
FIGS. 33A-H are perspective bottom, perspective top, top, back, bottom, side cross sectional, side, and front cross sectional views of a slim-finger emitter pad embodiment.
Figure 33B:
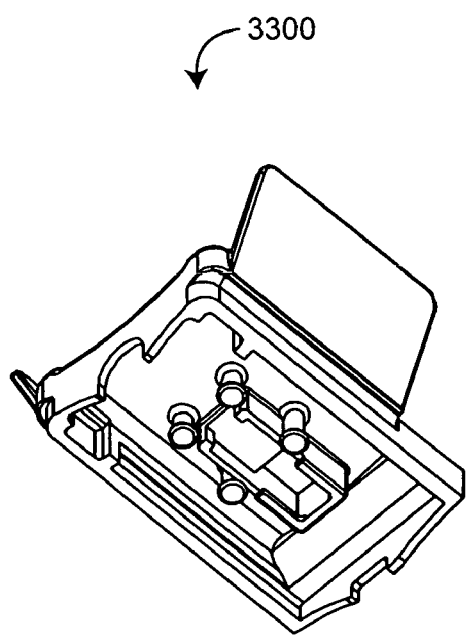
Figure 33C:
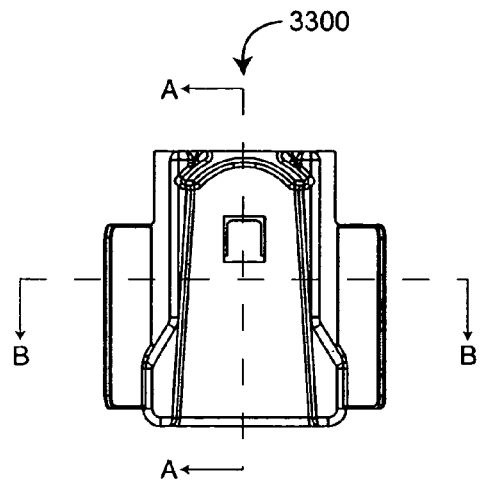
Figure 33F:
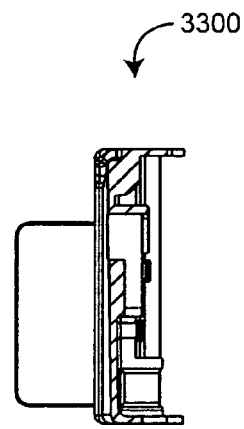
Figure 33D:
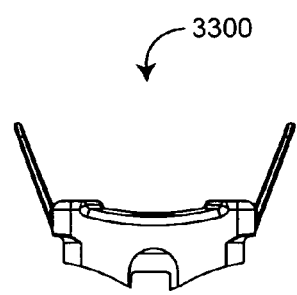
Figure 33G:
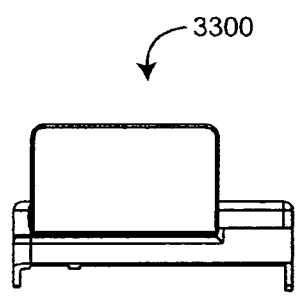
Figure 33E:
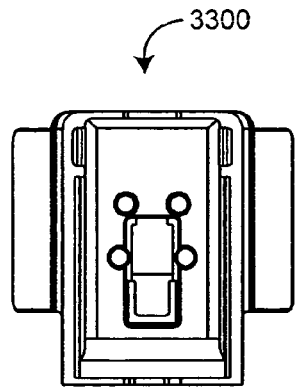
Figure 33H:
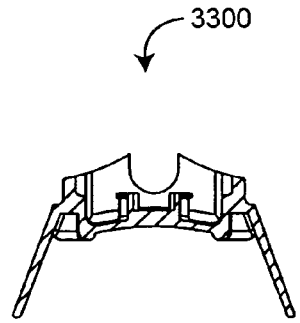
Figure 34A:
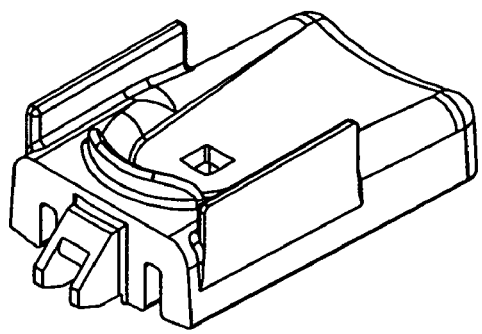
FIGS. 34A-H are perspective bottom, perspective top, top, back, bottom, side cross sectional, side, and front cross sectional views of a slim-finger detector pad embodiment.
Figure 34B:
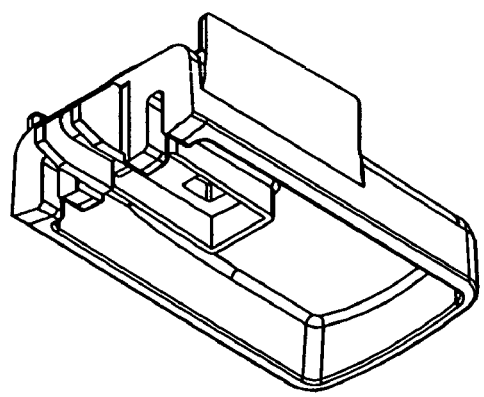
Figure 34C:
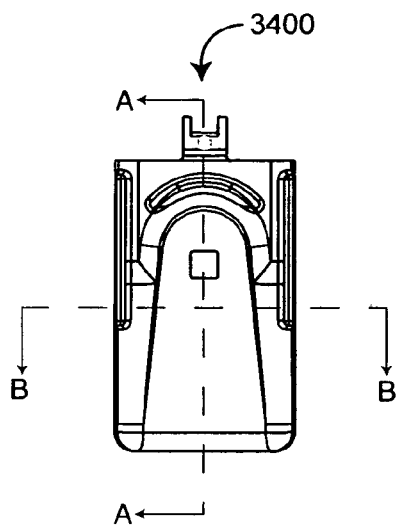
Figure 34F:
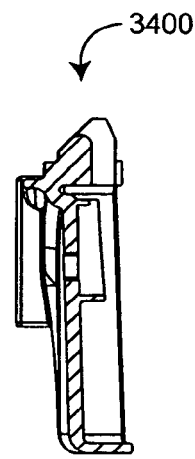
Figure 34D:
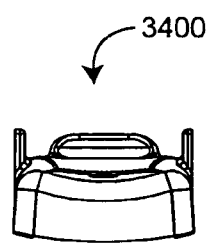
Figure 34G:
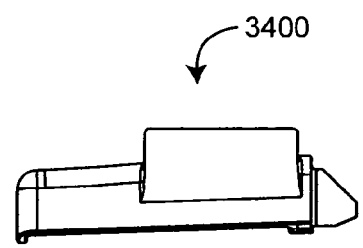
Figure 34E:
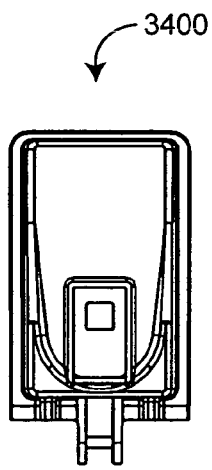
Figure 34H:
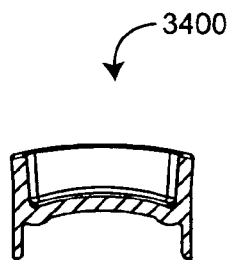

FIG. 28 illustrates a detector pad 2800 advantageously configured to position and comfortably maintain a fingertip relative to a detector assembly for accurate sensor measurements. In particular, the detector pad has fingertip positioning features including a guide 2810, a contour 2820 and a stop 2830. The guide 2810 is raised from the pad surface 2803 and narrows as the guide 2810 extends from a first end 2801 to a second end 2802 so as to increasingly conform to a fingertip as a fingertip is inserted along the pad surface 2803 from the first end 2801. The contour 2820 has an indentation defined along the pad surface 2803 generally shaped to conform to a fingertip positioned over a detector aperture 2840 located within the contour 2820. The stop 2830 is raised from the pad surface 2803 so as to block the end of a finger from inserting beyond the second end 2802. FIGS. 29A-B illustrate detector pad embodiments 3100, 3400 each having a guide 2810, a contour 2820 and a stop 2830, described in further detail with respect to FIGS. 31 and 34, respectively.

FIGS. 30A-H illustrate an emitter pad 3000 having emitter pad flaps 3010, an emitter window 3020, mounting pins 3030, an emitter assembly cavity 3040, isolation notches 3050, a flex circuit notch 3070 and a cable notch 3080. The emitter pad flaps 3010 overlap with detector pad flaps 3110 (FIGS. 31A-H) to block ambient light. The emitter window 3020 provides an optical path from the emitter array 700 (FIG. 8) to a tissue site. The mounting pins 3030 accommodate apertures in the flex circuit mounting ears 2214 (FIG. 22), and the cavity 3040 accommodates the emitter assembly 500 (FIG. 21). Isolation notches 3050 mechanically decouple the shell attachment 3060 from the remainder of the emitter pad 3000. The flex circuit notch 3070 accommodates the flex circuit tail 2206 (FIG. 22) routed to the detector pad 3100 (FIGS. 31A-H). The cable notch 3080 accommodates the sensor cable 4400 (FIGS. 44A-B). FIGS. 33A-H illustrate an alternative slim finger emitter pad 3300 embodiment.

FIGS. 31A-H illustrate a detector pad 3100 having detector pad flaps 3110, a shoe box cavity 3120 and isolation notches 3150. The detector pad flaps 3110 overlap with emitter pad flaps 3010 (FIGS. 30A-H), interleaving to block ambient light. The shoe box cavity 3120 accommodates a shoe box 3200 (FIGS. 32A-H) described below. Isolation notches 3150 mechanically decouple the attachment points 3160 from the remainder of the detector pad 3100. FIGS. 34A-H illustrate an alternative slim finger detector pad 3400 embodiment.

FIGS. 32A-H illustrate a shoe box 3200 that accommodates the detector assembly 2400 (FIG. 24). A detector window 3210 provides an optical path from a tissue site to the detector 2410 (FIG. 24). A flex circuit notch 3220 accommodates the flex circuit tail 2206 (FIG. 22) routed from the emitter pad 3000 (FIGS. 30A-H). In one embodiment, the shoe box 3200 is colored black or other substantially light absorbing color and the emitter pad 3000 and detector pad 3100 are each colored white or other substantially light reflecting color.

Figure 35A:
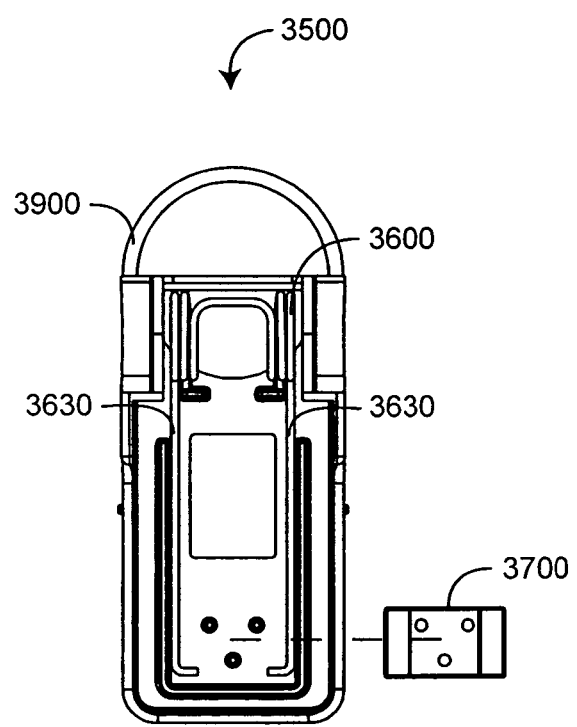
FIGS. 35A-B are plan and cross sectional views, respectively, of a spring assembly embodiment.
Figure 35B:
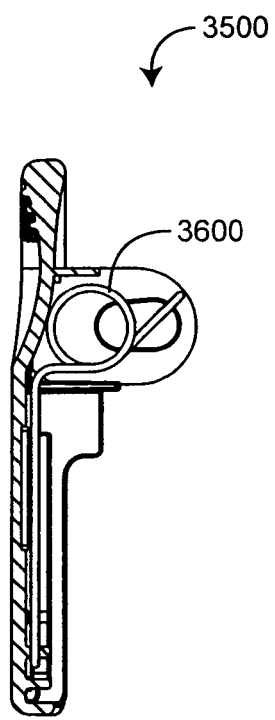

FIGS. 35-37 illustrate a spring assembly 3500 having a spring 3600 configured to urge together an emitter shell 3800 (FIG. 46) and a detector shell 3900. The detector shell is rotatably connected to the emitter shell. The spring is disposed between the shells 3800, 3900 and adapted to create a pivot point along a finger gripped between the shells that is substantially behind the fingertip. This advantageously allows the shell hinge 3810, 3910 (FIGS. 38-39) to expand so as to distribute finger clip force along the inserted finger, comfortably keeping the fingertip in position over the detector without excessive force.

Figure 36A:
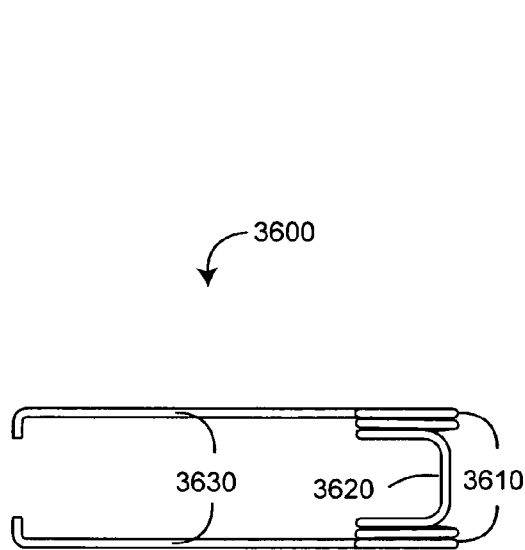
FIGS. 36A-C are top, perspective and side views of a finger clip spring.
Figure 36B:
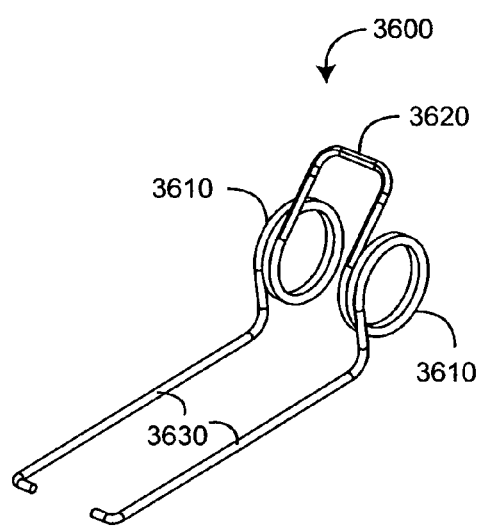
Figure 36C:
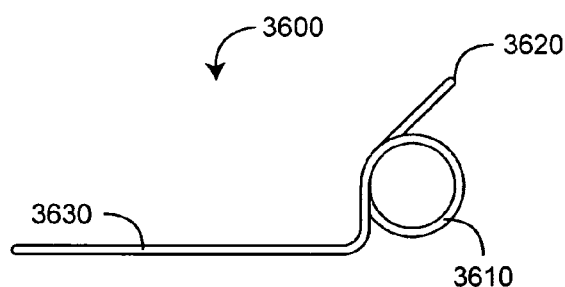
Figure 38A:
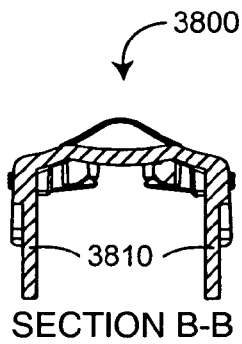
FIGS. 38A-D are front cross sectional, bottom, front and side cross sectional views of an emitter-pad shell.
Figure 38B:
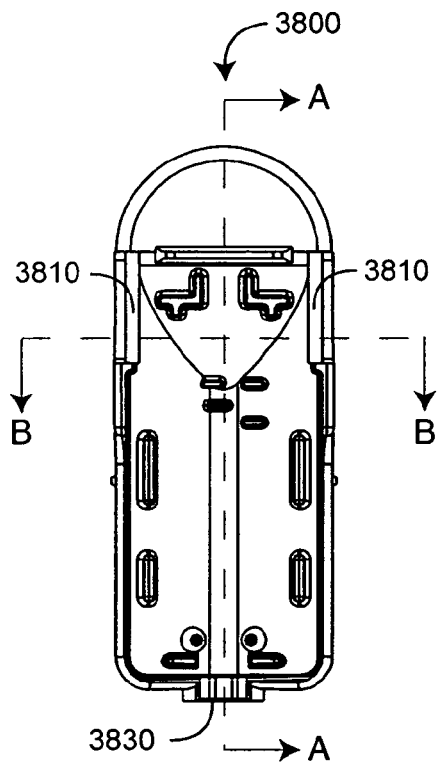
Figure 38D:
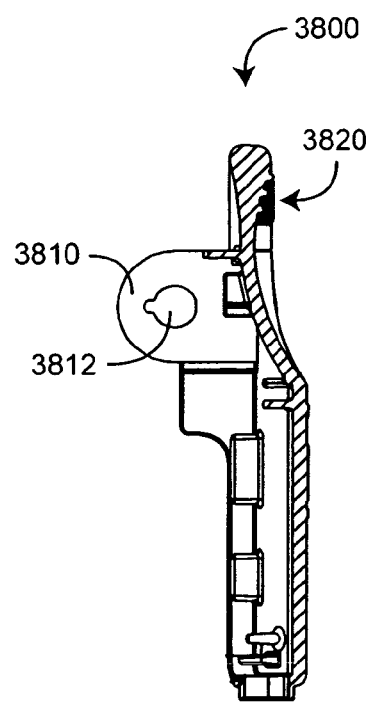
Figure 38C:
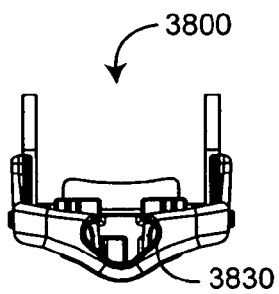
Figure 39A:
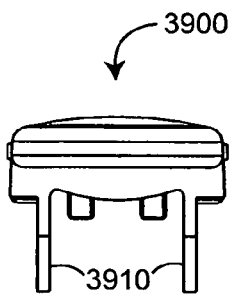
FIGS. 39A-D are back, top, front and side cross sectional views of a detector-pad shell.
Figure 39B:
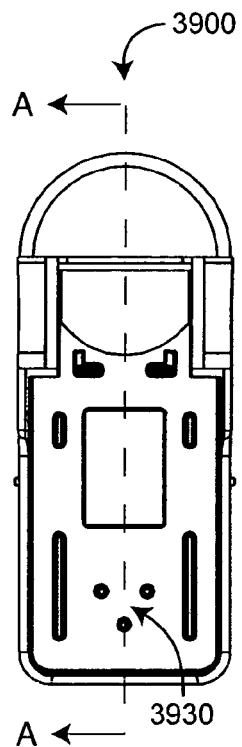
Figure 39D:
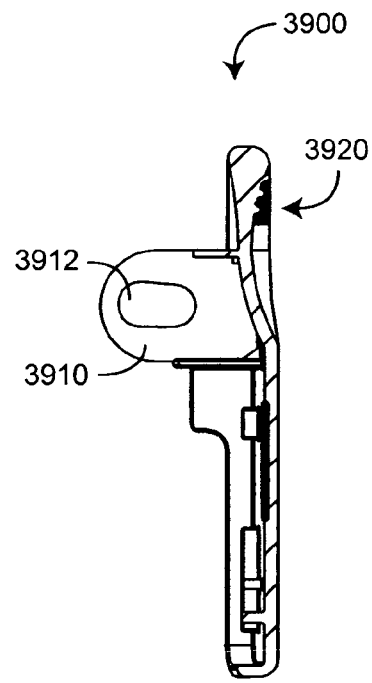
Figure 39C:
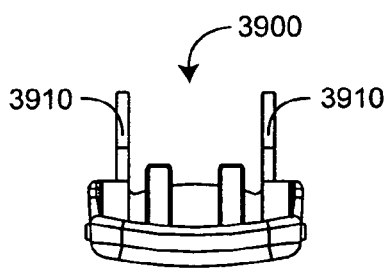

As shown in FIGS. 36A-C, the spring 3600 has coils 3610, an emitter shell leg 3620 and a detector shell leg 3630. The emitter shell leg 3620 presses against the emitter shell 3800 (FIGS. 38A-D) proximate a grip 3820 (FIGS. 38A-D). The detector shell legs 3630 extend along the detector shell 3900 (FIGS. 39A-D) to a spring plate 3700 (FIGS. 37A-D) attachment point. The coil 3610 is secured by hinge pins 410 (FIG. 46) and is configured to wind as the finger clip is opened, reducing its diameter and stress accordingly.

As shown in FIGS. 37A-D the spring plate 3700 has attachment apertures 3710, spring leg slots 3720, and a shelf 3730.

The attachment apertures 3710 accept corresponding shell posts 3930 (FIGS. 39A-D) so as to secure the spring plate 3700 to the detector shell 3900 (FIGS. 39A-D). Spring legs 3630 (FIGS. 36A-C) are slidably anchored to the detector shell 3900 (FIGS. 39A-D) by the shelf 3730, advantageously allowing the combination of spring 3600, shells 3800, 3900 and hinges 3810, 3910 to adjust to various finger sizes and shapes.

FIGS. 38-39 illustrate the emitter and detector shells 3800, 3900, respectively, having hinges 3810, 3910 and grips 3820, 3920. Hinge apertures 3812, 3912 accept hinge pins 410 (FIG. 46) so as to create a finger clip. The detector shell hinge aperture 3912 is elongated, allowing the hinge to expand to accommodate a finger.

Monitor And Sensor

Figure 40:
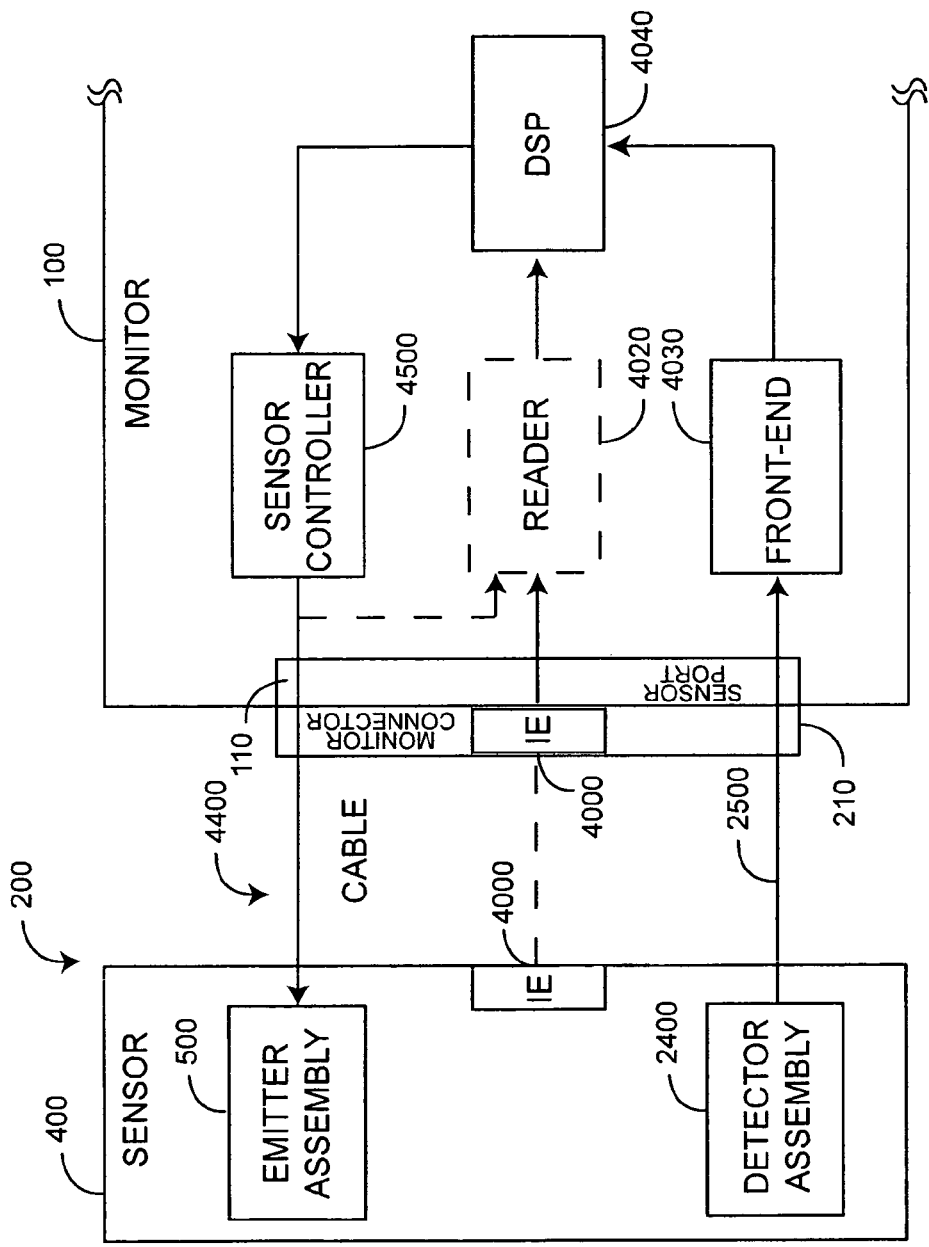
FIG. 40 is a general block diagram of a monitor and a sensor.

FIG. 40 illustrates a monitor 100 and a corresponding sensor assembly 200, as described generally with respect to FIGS. 1-3, above. The sensor assembly 200 has a sensor 400 and a sensor cable 4400. The sensor 400 houses an emitter assembly 500 having emitters responsive to drivers within a sensor controller 4500 so as to transmit optical radiation into a tissue site. The sensor 400 also houses a detector assembly 2400 that provides a sensor signal 2500 responsive to the optical radiation after tissue attenuation. The sensor signal 2500 is filtered, amplified, sampled and digitized by the front-end 4030 and input to a DSP (digital signal processor) 4040, which also commands the sensor controller 4500. The sensor cable 4400 electrically communicates drive signals from the sensor controller 4500 to the emitter assembly 500 and a sensor signal 2500 from the detector assembly 2400 to the front-end 4030. The sensor cable 4400 has a monitor connector 210 that plugs into a monitor sensor port 110.

In one embodiment, the monitor 100 also has a reader 4020 capable of obtaining information from an information element (IE) in the sensor assembly 200 and transferring that information to the DSP 4040, to another processor or component within the monitor 100, or to an external component or device that is at least temporarily in communication with the monitor 100. In an alternative embodiment, the reader function is incorporated within the DSP 4040, utilizing one or more of DSP I/O, ADC, DAC features and corresponding processing routines, as examples.

In one embodiment, the monitor connector 210 houses the information element 4000, which may be a memory device or other active or passive electrical component. In a particular embodiment, the information element 4000 is an EPROM, or other programmable memory, or an EEPROM, or other reprogrammable memory, or both. In an alternative embodiment, the information element 4000 is housed within the sensor 400, or an information element 4000 is housed within both the monitor connector 4000 and the sensor 400. In yet another embodiment, the emitter assembly 500 has an information element 4000, which is read in response to one or more drive signals from the sensor controller 4500, as described with respect to FIGS. 41-43, below. In a further embodiment, a memory information element is incorporated into the emitter array 700 (FIG. 8) and has characterization information relating to the LEDs 801 (FIG. 8). In one advantageous embodiment, trend data relating to slowly varying parameters, such as perfusion index, HbCO or METHb, to name a few, are stored in an IE memory device, such as EEPROM.

Back-to-Back LEDs

Figure 41A:
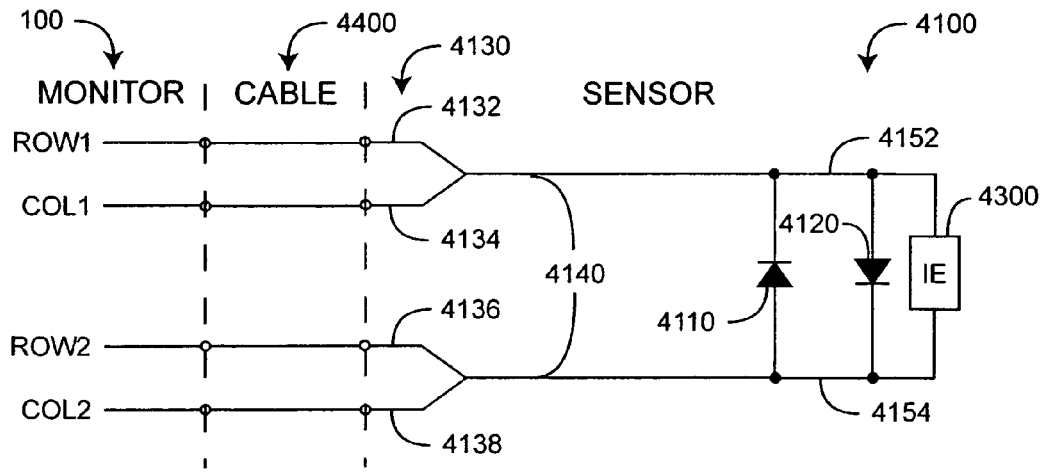
FIGS. 41A-C are schematic diagrams of grid drive embodiments for a sensor having back-to-back diodes and an information element.
Figure 41B:
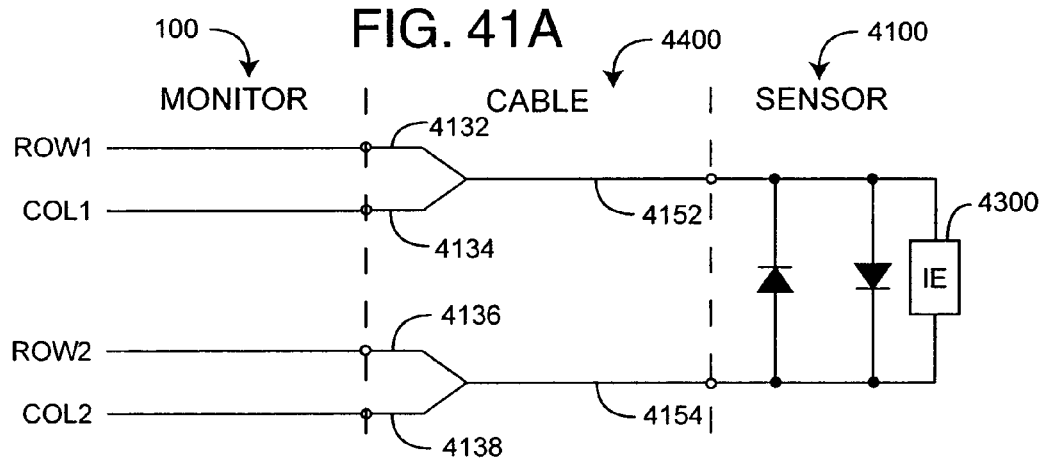
Figure 41C:
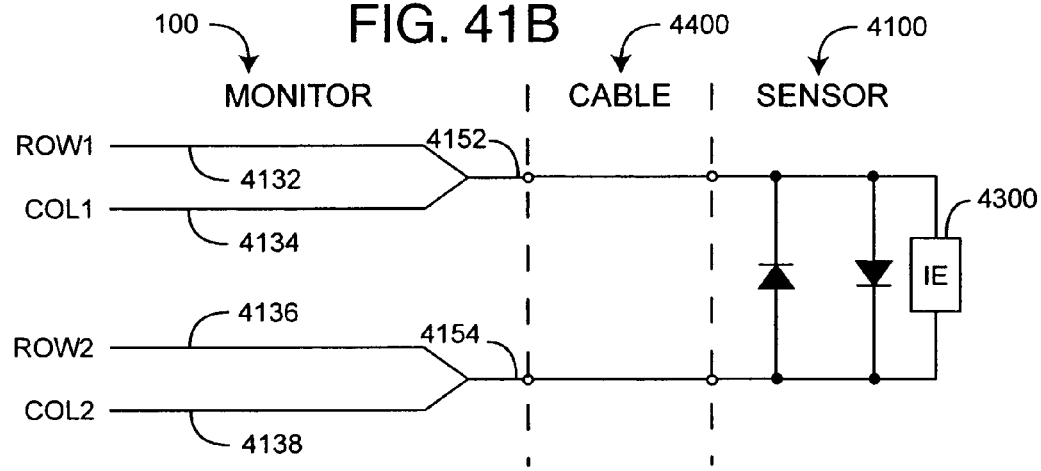
Figure 42:
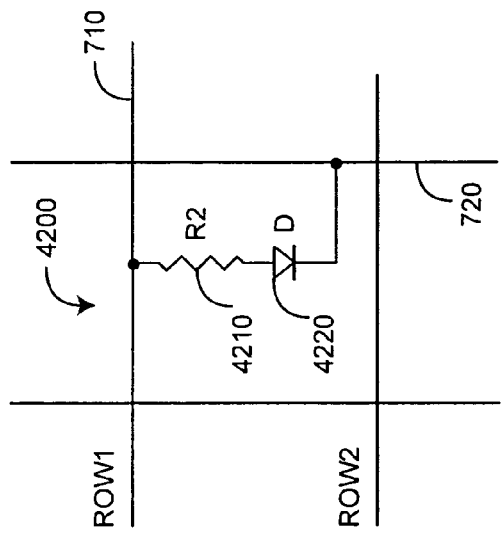
FIG. 42 is a schematic diagrams of a grid drive embodiment for an information element.

FIGS. 41-43 illustrate alternative sensor embodiments. A sensor controller 4500 configured to activate an emitter array 700 (FIG. 7) arranged in an electrical grid, is described with respect to FIG. 7, above. Advantageously, a sensor controller 4500 so configured is also capable of driving a conventional two-wavelength (red and IR) sensor 4100 having back-to-back LEDs 4110, 4120 or an information element 4300 or both.

FIG. 41A illustrates a sensor 4100 having an electrical grid 4130 configured to activate light emitting sources by addressing at least one row conductor and at least one column conductor. A first LED 4110 and a second LED 4120 are configured in a back-to-back arrangement so that a first contact 4152 is connected to a first LED 4110 cathode and a second LED 4120 anode and a second contact 4154 is connected to a first LED 4110 anode and a second LED 4120 cathode. The first contact 4152 is in communications with a first row conductor 4132 and a first column conductor 4134. The second contact is in communications with a second row conductor 4136 and a second column conductor 4138. The first LED 4110 is activated by addressing the first row conductor 4132 and the second column conductor 4138. The second LED 4120 is activated by addressing the second row conductor 4136 and the first column conductor 4134.

FIG. 41B illustrates a sensor cable 4400 embodiment capable of communicating signals between a monitor 100 and a sensor 4100. The cable 4400 has a first row input 4132, a first column input 4134, a second row input 4136 and a second column input 4138. A first output 4152 combines the first row input 4132 and the first column input 4134. A second output 4154 combines a second row input 4136 and second column input 4138.

FIG. 41C illustrates a monitor 100 capable of communicating drive signals to a sensor 4100. The monitor 4400 has a first row signal 4132, a first column signal 4134, a second row signal 4136 and a second column signal 4138. A first output signal 4152 combines the first row signal 4132 and the first column signal 4134. A second output signal 4154 combines a second row signal 4136 and second column signal 4138.

Information Elements

FIGS. 42-43 illustrate information element 4200-4300 embodiments in communications with emitter array drivers configured to activate light emitters connected in an electrical grid. The information elements are configured to provide information as DC values, AC values or a combination of DC and AC values in response corresponding DC, AC or combination DC and AC electrical grid drive signals. FIG. 42 illustrates information element embodiment 4200 advantageously driven directly by an electrical grid having rows 710 and columns 720. In particular, the information element 4200 has a series connected resistor $R_2$ 4210 and diode 4220 connected between a row line 710 and a column line 720 of an electrical grid. In this manner, the resistor $R_2$ value can be read in a similar manner that LEDs 810 (FIG. 8) are activated. The diode 4220 is oriented, e.g. anode to row and cathode to column as the LEDs so as to prevent parasitic currents from unwanted activation of LEDs 810 (FIG. 8).

Figure 43C:
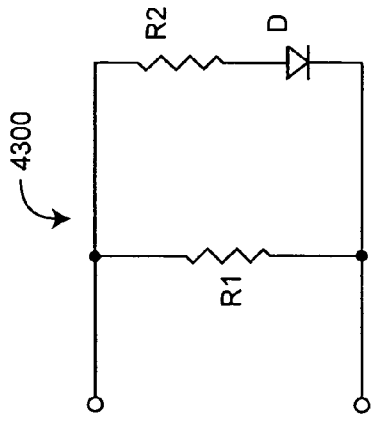
FIGS. 43A-C are schematic diagrams for grid drive readable information elements.
Figure 43B:
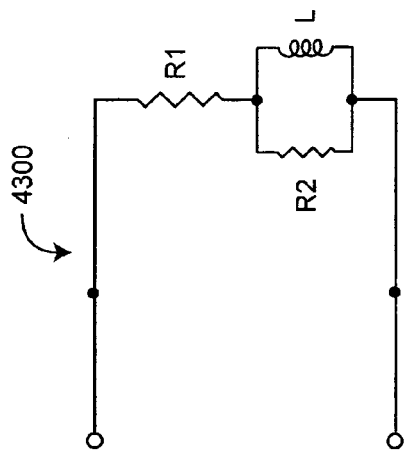
Figure 43A:
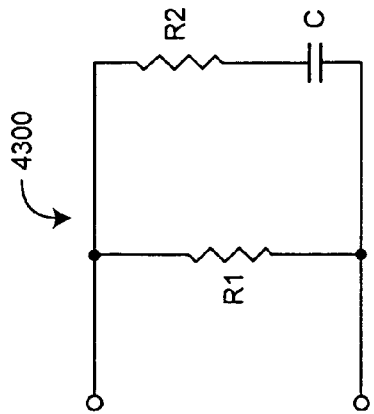

FIGS. 43A-C illustrate other embodiments where the value of $R_1$ is read with a DC grid drive current and a corresponding grid output voltage level. In other particular embodiments, the combined values of $R_1$, $R_2$ and C or, alternatively, $R_1$, $R_2$ and L are read with a varying (AC) grid drive currents and a corresponding grid output voltage waveform. As one example, a step in grid drive current is used to determine component values from the time constant of a corresponding rise in grid voltage. As another example, a sinusoidal grid drive current is used to determine component values from the magnitude or phase or both of a corresponding sinusoidal grid voltage. The component values determined by DC or AC electrical grid drive currents can represent sensor types, authorized suppliers or manufacturers, emitter wavelengths among others. Further, a diode D (FIG. 43C) can be used to provide one information element reading $R_1$ at one drive level or polarity and another information element reading, combining $R_1$ and $R_2$, at a second drive level or polarity, i.e. when the diode is forward biased.

Passive information element 4300 embodiments may include any of various combinations of resistors, capacitors or inductors connected in series and parallel, for example. Other information element 4300 embodiments connected to an electrical grid and read utilizing emitter array drivers incorporate other passive components, active components or memory components, alone or in combination, including transistor networks, PROMs, ROMs, EPROMs, EEPROMs, gate arrays and PLAs to name a few.

Sensor Cable

FIGS. 44A-B illustrate a sensor cable 4400 having an outer jacket 4410, an outer shield 4420, multiple outer wires 4430, an inner jacket 4440, an inner shield 4450, a conductive polymer 4460 and an inner twisted wire pair 4470. The outer wires 4430 are advantageously configured to compactly carry multiple drive signals to the emitter array 700 (FIG. 7). In one embodiment, there are twelve outer wires 4430 corresponding to four anode drive signals 4501 (FIG. 45), four cathode drive signals 4502 (FIG. 45), two thermistor pinouts 1450 (FIG. 15) and two spares. The inner twisted wire pair 4470 corresponds to the sensor signal 2500 (FIG. 25) and is extruded within the conductive polymer 4460 so as to reduce triboelectric noise. The shields 4420, 4450 and the twisted pair 4470 boost EMI and crosstalk immunity for the sensor signal 2500 (FIG. 25).

Controller

Figure 45:
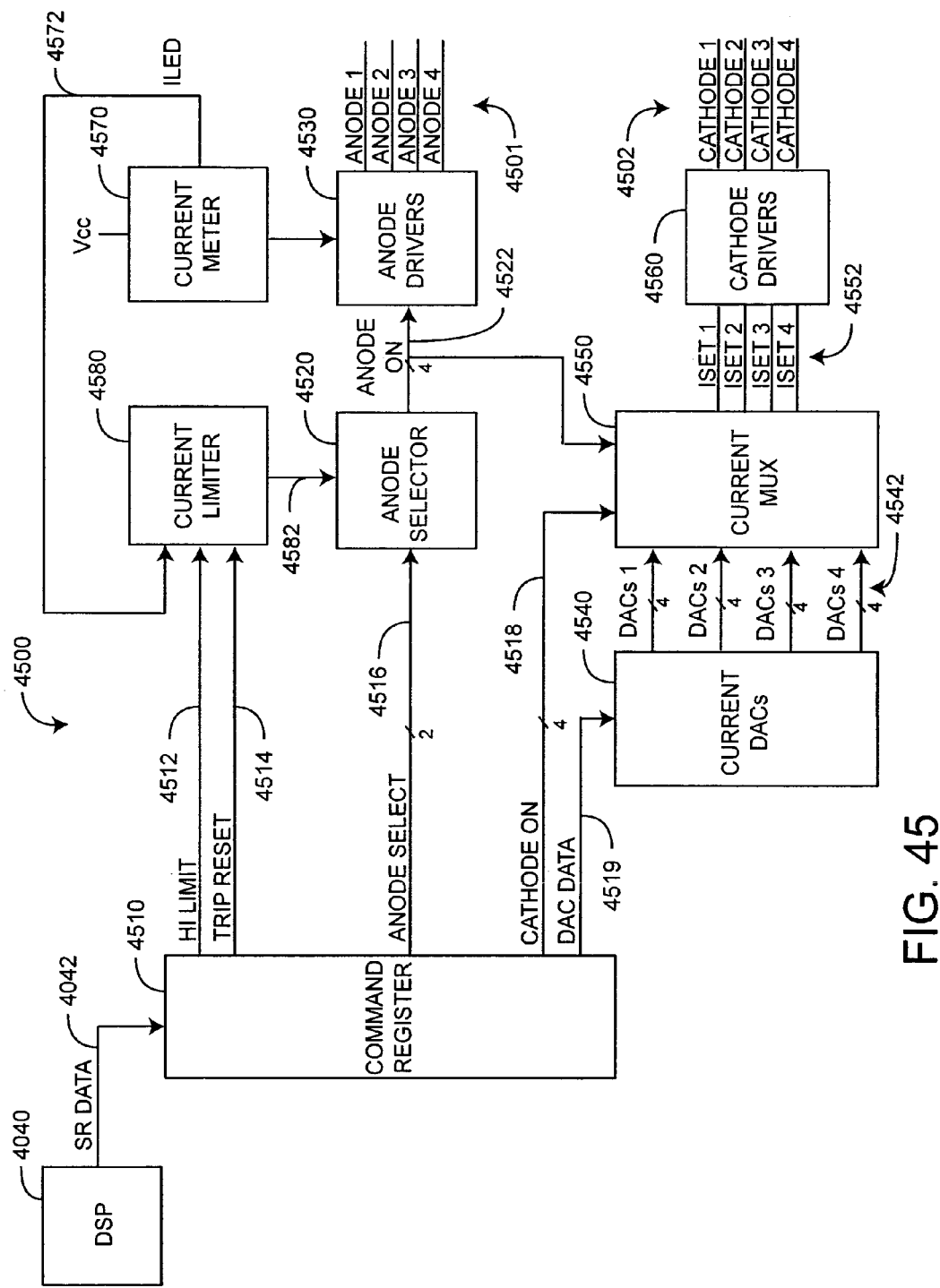
FIG. 45 is a block diagram of a sensor controller embodiment.

FIG. 45 illustrates a sensor controller 4500 located in the monitor 100 (FIG. 1) and configured to provide anode drive signals 4501 and cathode drive signals 4502 to the emitter array 700 (FIG. 7). The DSP (digital signal processor) 4040, which performs signal processing functions for the monitor, also provides commands 4042 to the sensor controller 4500. These commands determine drive signal 4501, 4502 levels and timing. The sensor controller 4500 has a command register 4510, an anode selector 4520, anode drivers 4530, current DACs (digital-to-analog converters) 4540, a current multiplexer 4550, cathode drivers 4560, a current meter 4570 and a current limiter 4580. The command register 4510 provides control signals responsive to the DSP commands 4042. In one embodiment, the command register 4510 is a shift register that loads serial command data 4042 from the DSP 4040 and synchronously sets output bits that select or enable various functions within the sensor controller 4500, as described below.

As shown in FIG. 45, the anode selector 4520 is responsive to anode select 4516 inputs from the command register 4510 that determine which emitter array row 810 (FIG. 8) is active. Accordingly, the anode selector 4520 sets one of the anode on 4522 outputs to the anode drivers 4530, which pulls up to Vcc one of the anode outputs 4501 to the emitter array 700 (FIG. 8).

Also shown in FIG. 45, the current DACs 4540 are responsive to command register data 4519 that determines the currents through each emitter array column 820 (FIG. 8). In one embodiment, there are four, 12-bit DACs associated with each emitter array column 820 (FIG. 8), sixteen DACs in total. That is, there are four DAC outputs 4542 associated with each emitter array column 820 (FIG. 8) corresponding to the currents associated with each row 810 (FIG. 8) along that column 820 (FIG. 8). In a particular embodiment, all sixteen DACs 4540 are organized as a single shift register, and the command register 4510 serially clocks DAC data 4519 into the DACs 4540. A current multiplexer 4550 is responsive to cathode on 4518 inputs from the command register 4510 and anode on 4522 inputs from the anode selector 4520 so as to convert the appropriate DAC outputs 4542 to current set 4552 inputs to the cathode drivers 4560. The cathode drivers 4560 are responsive to the current set 4552 inputs to pull down to ground one to four of the cathode outputs 4502 to the emitter array 700 (FIG. 8).

The current meter 4570 outputs a current measure 4572 that indicates the total LED current driving the emitter array 700 (FIG. 8). The current limiter 4580 is responsive to the current measure 4572 and limits specified by the command register 4510 so as to prevent excessive power dissipation by the emitter array 700 (FIG. 8). The current limiter 4580 provides an enable 4582 output to the anode selector 4520. A Hi Limit 4512 input specifies the higher of two preset current limits. The current limiter 4580 latches the enable 4582 output in an off condition when the current limit is exceeded, disabling the anode selector 4520. A trip reset 4514 input resets the enable 4582 output to re-enable the anode selector 4520.

Sensor Assembly

Figure 46:
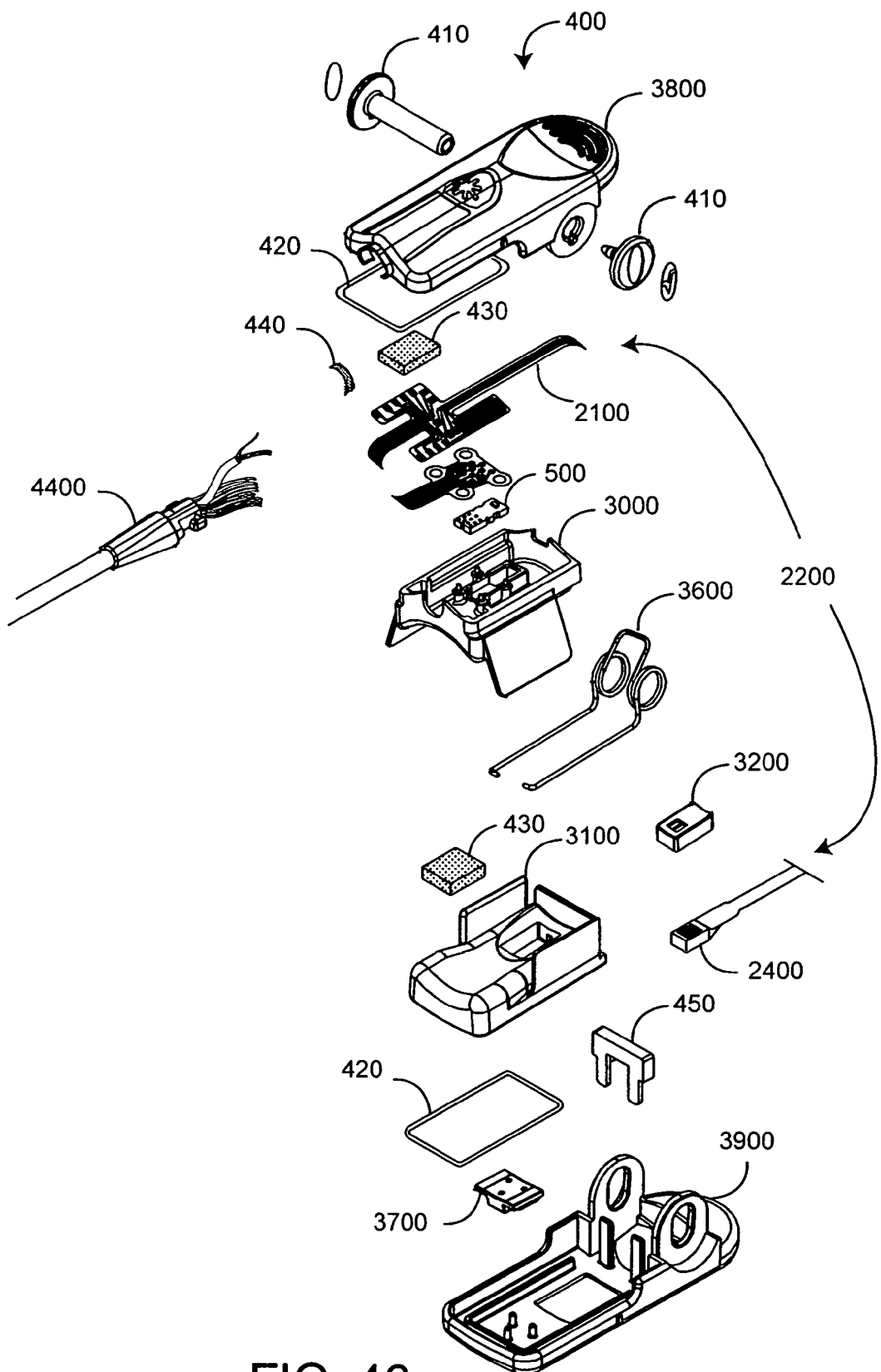
FIG. 46 is a detailed exploded perspective view of a multiple wavelength sensor embodiment.

As shown in FIG. 46, the sensor 400 has an emitter shell 3800, an emitter pad 3000, a flex circuit assembly 2200, a detector pad 3100 and a detector shell 3900. A sensor cable 4400 attaches to the flex circuit assembly 2200, which includes a flex circuit 2100, an emitter assembly 500 and a detector assembly 2400. The portion of the flex circuit assembly 2200 having the sensor cable 4400 attachment and emitter assembly 500 is housed by the emitter shell 3800 and emitter pad 3000. The portion of the flex circuit assembly 2200 having the detector assembly 2400 is housed by the detector shell 3900 and detector pad 3100. In particular, the detector assembly 2400 inserts into a shoe 3200, and the shoe 3200 inserts into the detector pad 3100. The emitter shell 3800 and detector shell 3900 are fastened by and rotate about hinge pins 410, which insert through coils of a spring 3600. The spring 3600 is held to the detector shell 3900 with a spring plate 3700. A finger stop 450 attaches to the detector shell. In one embodiment, a silicon adhesive 420 is used to attach the pads 3000, 3100 to the shells 3800, 3900, a silicon potting compound 430 is used to secure the emitter and detector assemblies 500, 2400 within the pads 3000, 3100, and a cyanoacrylic adhesive 440 secures the sensor cable 4400 to the emitter shell 3800.

A multiple wavelength sensor has been disclosed in detail in connection with various embodiments. These embodiments are disclosed by way of examples only and are not to limit the scope of the claims that follow. One of ordinary skill in art will appreciate many variations and modifications.

What is claimed is:

1. A physiological sensor comprising:
    an electrical grid configured to activate a plurality of light emitting sources by addressing at least one of a plurality of row conductors and at least one of a plurality of column conductors,
    a first LED and a second LED configured in a back-to-back arrangement so that a first contact is connected to a first LED cathode and a second LED anode and a second contact is connected to a first LED anode and a second LED cathode,
    wherein the first contact is in communications with a first one of the row conductors and a first one of the column conductors,
    wherein the second contact is in communications with a second one of the row conductors and a second one of the column conductors,
    wherein the first LED is activated by addressing the first row conductor and the second column conductor, and wherein the second LED is activated by addressing the second row conductor and the first column conductor.

2. The physiological sensor according to claim 1 further comprising an information element disposed between the first contact and the second contact.

3. The physiological sensor according to claim 2 wherein the information element is adapted to provide information in response to a DC electrical grid drive.

4. The physiological sensor according to claim 2 wherein the information element is adapted to provide information in response to an AC electrical grid drive.

5. The physiological sensor according to claim 2 wherein the information element is adapted to provide information in response to a combination of an AC electrical grid drive and a DC electrical grid drive.

6. The physiological sensor according to claim 2 wherein the information element comprises a passive information element.

7. The physiological sensor according to claim 2 wherein the information element comprises an active information element.

8. The physiological sensor according to claim 2 wherein the information element comprises a memory information element.

9. An electrical grid drive method comprising:
providing a physiological monitor having an electrical grid drive comprising a first and second row drive line and a first and second column drive line;
communicating at least a portion of the electrical grid drive to a physiological sensor; and
adapting the electrical grid drive to activate back-to-back configured LEDs, wherein the adapting comprises combining the first row and second column drive lines to activate a first LED and combining the second row and first column drive lines to activate a second LED.

10. The electrical grid drive method according to claim 9 wherein the combining comprises connecting at least some of the row and column drive lines in a cable, the cable adapted to provide communication between the monitor and the physiological sensor.

11. The electrical grid drive method according to claim 9 wherein the combining comprises connecting at least some of the row and column drive lines in the physiological sensor having the back-to-back configured LEDs.

* * * * *

UNITED STATES PATENT AND TRADEMARK OFFICE
CERTIFICATE OF CORRECTION

| | |
|---|---|
| PATENT NO. | : 8,050,728 B2 |
| APPLICATION NO. | : 11/366997 |
| DATED | : November 1, 2011 |
| INVENTOR(S) | : Ammar Al-Ali et al. |

It is certified that error appears in the above-identified patent and that said Letters Patent is hereby corrected as shown below:

In column 2, line 3, change " $I_\lambda = I_{0,\lambda} e^{-d_\lambda \cdot \mu_{a,\lambda}}$ " to -- $I_\lambda = I_{0,\lambda} e^{-d_\lambda \cdot \mu_{a,\lambda}}$ --.

Signed and Sealed this
Nineteenth Day of June, 2012

David J. Kappos
*Director of the United States Patent and Trademark Office*